US012685780B2

(12) United States Patent
Mochizuki et al.

(10) Patent No.: US 12,685,780 B2
(45) Date of Patent: Jul. 21, 2026

(54) IMMUNE INDUCER CONTAINING POLYNUCLEOTIDE-PEPTIDE CONJUGATE AND PHARMACEUTICAL COMPOSITION CONTAINING SAME

(71) Applicants: The University of Kitakyushu, Kitakyushu (JP); Daiichi Sankyo Company, Limited, Tokyo (JP)

(72) Inventors: Shinichi Mochizuki, Fukuoka (JP); Makoto Koizumi, Tokyo (JP); Koji Morita, Tokyo (JP)

(73) Assignees: The University of Kitakyushu, Kitakyushu (JP); Daiichi Sankyo Company, Limited, Tokyo (JP)

( * ) Notice: Subject to any disclaimer, the term of this patent is extended or adjusted under 35 U.S.C. 154(b) by 822 days.

(21) Appl. No.: 17/907,531

(22) PCT Filed: Mar. 26, 2021

(86) PCT No.: PCT/JP2021/012787
§ 371 (c)(1),
(2) Date: Sep. 27, 2022

(87) PCT Pub. No.: WO2021/193900
PCT Pub. Date: Sep. 30, 2021

(65) Prior Publication Data

US 2023/0144876 A1 May 11, 2023

(30) Foreign Application Priority Data

Mar. 27, 2020 (JP) ................................. 2020-057249

(51) Int. Cl.

| | |
|---|---|
| ***A61K 47/65*** | (2017.01) |
| ***A61K 31/7088*** | (2006.01) |
| ***A61K 39/00*** | (2006.01) |
| ***A61K 39/39*** | (2006.01) |
| ***C07K 7/06*** | (2006.01) |
| ***C12N 15/117*** | (2010.01) |

(52) U.S. Cl.
CPC .......... *A61K 47/65* (2017.08); *A61K 31/7088* (2013.01); *A61K 39/001156* (2018.08); *A61K 39/001192* (2018.08); *A61K 39/39* (2013.01); *C07K 7/06* (2013.01); *C12N 15/117* (2013.01); *A61K 2039/55561* (2013.01)

(58) Field of Classification Search
CPC .................... A61K 47/65; A61K 39/39; A61K 2039/55561; C07K 7/06; C12N 15/117
See application file for complete search history.

(56) References Cited

U.S. PATENT DOCUMENTS

| | | | |
|---|---|---|---|
| 10,195,270 | B2 | 2/2019 | Sakurai et al. |
| 11,793,874 | B2 | 10/2023 | Mochizuki et al. |
| 12,220,460 | B2 * | 2/2025 | Mochizuki ........... A61K 47/549 |
| 2006/0084149 | A1 | 4/2006 | Kimura et al. |
| 2008/0146488 | A1 | 6/2008 | Wettstein et al. |
| 2014/0051637 | A1 | 2/2014 | Suzumura et al. |
| 2015/0191730 | A1 | 7/2015 | Levy et al. |
| 2016/0000906 | A1 | 1/2016 | Diamond |
| 2016/0186178 | A1 | 6/2016 | Radovic-Moreno et al. |
| 2016/0208260 | A1 | 7/2016 | Ishii et al. |
| 2017/0007695 | A1 | 1/2017 | Sakurai et al. |
| 2017/0035864 | A1 | 2/2017 | Theriault |
| 2021/0106678 | A1 | 4/2021 | Mochizuki et al. |
| 2022/0031839 | A1 | 2/2022 | Mochizuki et al. |

FOREIGN PATENT DOCUMENTS

| | | | |
|---|---|---|---|
| CN | 101563104 | A | 10/2009 |
| EP | 1 142 591 | A1 | 10/2001 |
| EP | 3 858 383 | A1 | 8/2021 |
| JP | 2007-70307 | A | 3/2007 |
| JP | 2008509072 | A | 3/2008 |
| JP | 2010-174107 | A | 8/2010 |
| JP | 2017500313 | A | 1/2017 |
| TW | 201639583 | A | 11/2016 |
| WO | 200134207 | A1 | 5/2001 |
| WO | 2002072152 | A1 | 9/2002 |
| WO | 2008047852 | A1 | 4/2008 |
| WO | 2012147805 | A1 | 11/2012 |
| WO | 2015089114 | A1 | 6/2015 |
| WO | 2015118789 | A1 | 8/2015 |
| WO | 2016152767 | A1 | 9/2016 |
| WO | 2017217531 | A1 | 12/2017 |
| WO | 2020/067400 | A1 | 4/2020 |

OTHER PUBLICATIONS

Daftarian et al. 2005 (Novel conjugates of epitope fusion peptides with CpG-ODN display enhanced immunogenicity and HIV recognition; Vacine 23: 3453-3468) (Year: 2005).*

Tung et al. 2000 (Preparation and Applications of Peptide-Oligonucleotide Conjugates; Bioconjugate Chemistry 11(5): 605-618). (Year: 2000).*

(Continued)

*Primary Examiner* — Mary Maille Lyons
(74) *Attorney, Agent, or Firm* — Christensen O'Connor Johnson Kindness PLLC

(57) ABSTRACT

The present invention provides an immunity-inducing agent comprising a polynucleotide-peptide conjugate or a pharmaceutically acceptable salt thereof as an active component, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

26 Claims, 41 Drawing Sheets

Specification includes a Sequence Listing.

(56) References Cited

OTHER PUBLICATIONS

Kramer et al. 2017 (Intracellular Cleavable CpG Oligodeoxynucleotide-Antigen Conjugate Ehnances Anti-tumor Immunity; Molecular Therapy 25(1): 62-70) (Year: 2017).*
Palshof et al. 2024 (Non-preventable cases of breast, prostate, lung and colorectal cancer in 2050 in an elimination scenario of modifiable risk factors; Nature 14:8577 (Year: 2024).*
Israelsen et al. 2020 (Preventing Allergies in Infants: What Foods to Introduce and When; Utah State Extension; pp. 1-6) (Year: 2020).*
Bolcato et al. 2023 (Healthcare-acquired Sars-Cov2 infection: A viable legal category; International Journal of Risk & Safety in Medicine 34: 129-134) (Year: 2023).*
Extended European Search Report mailed Jul. 12, 2024, issued in corresponding Application No. EP 21776683.1, filed Mar. 26, 2021, 10 pages.
Irie, H., et al., "Immune Responses and Antitumor Effect through Delivering to Antigen Presenting Cells by Optimized Conjugates Consisting of CpG-DNA and Antigenic Peptide," Bioconjugate Chemistry, vol. 31, No. 11, Nov. 5, 2020, pp. 2585-2595.
Daftarian et al., "Novel conjugates of epitope fusion peptides with CpG-ODN display enhanced immunogenicity and HIV recognition," Vaccine (2005), vol. 23, No. 26, pp. 3453-3468.
Kramer, K., et al., "Comparative Study of 5'- and 3'-Linked CpG-Antigen Conjugates for the Induction of Cellular Immune Responses," ACS Omega, vol. 2, No. 1, Jan. 25, 2017, pp. 227-235.
Yamamoto, S., et al., "The discovery of immunostimulatory DNA sequence," in Raz, E. (eds) Immunostimulatory DNA Sequences. Springer, Berlin, 2000, 22:11-19.
Krieg, A.R., "CpG Motifs in Bacterial DNA and Their Immune Effects," Annu Rev Immunol. 2002; vol. 20, 709-760.
Wagner, H., "Bacterial CpG DNA Activates Immune Cells to Signal Infectious Danger," Adv Immunol. 1999, vol. 73, 329-368.
Khan, S., et al., "Distinct Uptake Mechanisms but Similar Intracellular Processing of Two Different Toll-like Receptor Ligand-Peptide Conjugates in Dendritic Cells," J Biol Chem., Jul. 20, 2007, 282(29), 21145-21159.
Kramer, K., et al., "Intracellular Cleavable CpG Oligodeoxynucleotide-Antigen Conjugate Enhances Anti-tumor Immunity," Molecular Therapy, Jan. 4, 2017, 25(1), pp. 62-70.
Shirota, H. and Klinman D.M., "TLR-9 Agonist Immunostimulatory Sequence Adjuvants Linked to Cancer Antigens," Methods Mol. Biol. 2014, 1139, 337-344.
Irie, H., et al., "Immune Responses and Antitumor Effect through Delivering to Antigen Presenting Cells by Optimized Conjugates Consisting of CPG-DNA and Antigenic Peptide," Bioconjugate Chem., 2020, 31, pp. 2585-2595.
Motohiko, S., et al., "Immunotherapy with CpG DNA conjugated with T-cell epitope peptide of an allergenic Cry j 2 protein is useful for control of allergic conditions in mice," International Immunopharmacology, Jan. 2007, vol. 7, Issue 1, pp. 46-54.
Rapin, N., et al., "Immunogenetics," Dec. 2008, 60(12), pp. 759-765.
Kupihar, Z., et al., "Synthesis and Application of a Novel, Crystalline Phosphoramidite Monomer with Thiol Terminus, Suitable for the Synthesis of DNA Conjugates," Bioorganic & Medicinal Chemistry, Sep. 7, 2001, vol. 9, pp. 1241-1247.
Kramer, K., et al., "Comparative Study of 5'- and 3'-Linked CpG-Antigen Conjugates for the Induction of Cellular Immune Responses," ACS Omega, Jan. 25, 2017, 2(1), pp. 227-235.
International Search Report mailed Apr. 21, 2021 issued in corresponding Application No. PCT/JP2021/012787, filed Mar. 26, 2021, 3 pages.
International Search Report mailed Nov. 19, 2019, issued in related International Application No. PCT/JP2019/038090, filed Sep. 27, 2019, 12 pages.
International Search Report mailed May 1, 2018, issued in related International Application No. PCT/JP2018/011201, filed Mar. 20, 2018, 6 pages.
Extended European Search Report mailed Aug. 24, 2022, issued in related European Application No. 19865489.9, filed Sep. 27, 2019, 2018, 14 pages.
Office Action mailed Aug. 23, 2022, issued in related Japanese Application No. 2019-509625, filed Mar. 20, 2018, 7 pages.
Kapadia C.H., et al. "Extending antigen release from particulate vaccines results in enhanced antitumor immune response," Journal of Controlled Release 2018, vol. 269, pp. 393-404.
Maurer, T. et al., "CpG-DNA aided cross-presentation of soluble antigens by dendritic cells", European Journal of Immunology 32(8): 2356-2364, Aug. 2, 2022.
Miyoshi, K., et al., "Polysaccharide-Polynucleotide Complexes. Part 32. Structural Analysis of the Curdlan/Poly (Cytidylic Acid) Complex With Semiempirical Molecular Orbital Calculations," Biomacromolecules 6: 1540-1546, 2005.
Mizu, M., et al.,"A Polysaccharide Carrier for Immunostimulatory CpG DNAs To Enhance Cytokine Secretion," Journal of the American Chemical Society 126:8372-8373, 2004.
Mizu, M., et al., "Protection of Polynucleotides Against Nuclease-Mediated Hydrolysis by Complexation With Schizophyllan," Biomaterials 25(15):3109-3116, 2004.
Mochizuki, S., et al., "Complex Consisting of t}-Glucan and Antigenic Peptides With Cleavage Site for Glutathione and Aminopeptidases Induces Potent Cytotoxic T Lymphocytes," Bioconjugate Chemistry 28:2246-2253, Jul. 2017.
Mochizuki, S., and K. Sakurai, "Dectin-1 Targeting Delivery of TNF-a Antisense ODNs Complexed With B-1,3-Glucan Protects Mice From LPS-Induced Hepatitis," Journal of Controlled Release 151: 155-161, 2011.
Mochizuki, S., et al., "Immunization With Antigenic Peptides Complexed With β-Glucan Induces Potent Cytotoxic T-Lymphocyte Activity in Combination With CpG-ODNs," Journal of Controlled Release 220:495-502, Dec. 2015.
Sakurai, K. and S. Shinkai, "Molecular Recognition of Adenine, Cytosine, and Uracil in a Single-Stranded RNA by a Natural Polysaccharide: Schizophyllan," Journal of the American Chemical Society 122:4520-4521, 2000.
Sakurai, K., et al., "Polysaccharide-Polynucleotide Complexes.2. Complementary Polynucleotide Mimic Behavior of the Natural Polysaccharide Schizophyllan in the Macromolecular Complex With Single-Stranded RNA and DNA," Biomacromolecules 2:641-650, 2001.
Shimada, N., et al., "Synthesis and In Vitro Characterization of Antigen-Conjugated Polysaccharide as a CpG DNA Carrier," Bioconjugate Chemistry 17:1136-1140, 2006.
Shirota, H. et al., "Regulation of Murine Airway Eosinophilia and Th2 Cells by Antigen-Conjugated CpG Oligodeoxynucleotides as a Novel Antigen-Specific Immunomodulator", The Journal of Immunology, 164:5575-5582, Jan. 1, 2000.
Taniguchi, M., et al., "Microbial DNAs (CpG DNA) and TLR9," Standard Immunology, 2nd ed., p. 333, Section 5, 2002.
Tighe, H., et al., "Conjugation of Immunostimulatory DNA to the Short Ragweed Allergen Amb a 1 Enhances Its Immunogenicity and Reduces Its Allergenicity," Journal of Allergy and Clinical Immunology 106(1 Pt 1):124-134, Jul. 2000.
Aurisicchio, L. et al., "A novel minigene scaffold for therapeutic cancer vaccines," OncoImmunology 3, e27529-1-e27529-13; Jan. 2014.
Maurer, T. et al., "CpG-DNA aided cross-presentation of soluble antigens by dendritic cells", European Journal of Immunology 32(8): 2356-2364, Aug. 2, 2002.
First Chinese Office Action mailed on Feb. 19, 2025, issued in Chinese App No. 202180024931.3; 18 pages.
Office Action mailed Jun. 11, 2025, issued in U.S. Appl. No. 17/280,605, filed Mar. 26, 2021, 39 pages.
Hayashi, M., et al., "Resistance to influenza A virus infection by antigen-conjugated CpG oligonucleotides, a novel antigen-specific in1munomodulator," Biochemical and Biophysical Research Communications 329 (2005), 230-236.

* cited by examiner

| | Retention time (min.) | Height (µV) | Area (µVsec) | %Area |
|---|---|---|---|---|
| 1 | 10.162 | 4868 | 87542 | 2.65 |
| 2 | 14.067 | 20318 | 93708 | 2.84 |
| 3 | 14.197 | 415039 | 3041653 | 92.17 |
| 4 | 14.375 | 14131 | 77234 | 2.34 |

CSVYDFFVWL (10 aa)

CpG30(S)a-mTRP2pep9 (Compound 1)
(peptide; 200 ng, CpG; 1.7 μg/head)

PBS

CpG30(S)a-mTRP2pep10 (Compound 5)

(peptide; 200 ng, CpG; 1.7 μg/head)

PBS

PBS

CpG30(S)a-mTRP2pep9
(Compound 1)

CpG20(S)a-mTRP2pep9
(Compound 2)

| | | |
|---|---|---|
| peptide; | 200 ng | 200 ng |
| CpG; | 1.7 μg | 1.2 μg |

PBS

CpG30(S)a-hGP100pep10
(Compound 6)

peptide; 200 ng

CpG; 1.7 μg

CpG30(S)a-hGP100pep9
(Compound 3)

200 ng 1.7 μg

PBS

CpG30a-S-S-CMTRP2-9
(peptide; 1000 ng, CpG; 8.5 μg/head)

CpG30a-S-S-CMTRP2-9
(peptide; 200 ng, CpG; 1.7 μg/head)

CpG30a-S-S-TRP2-14
(peptide; 200 ng, CpG; 1.7 μg/head)

CpG30a-S-S-TRP2-12
(peptide; 200 ng, CpG; 1.7 μg/head)

PBS

CpG30(S)a-mTRP2pep9
(peptide; 200 ng, CpG; 1.7 μg/head)

ISS1018-mTRP2pep9
(peptide; 200 ng, CpG; 1.2 μg/head)

ODN2006-mTRP2pep9
(peptide; 200 ng, CpG; 1.4 μg/head)

ODN1826-mTRP2pep9
(peptide; 200 ng, CpG; 1.1 μg/head)

CpG30(S)a2-OVApep8
(peptide; 20 ng, CpG; 0.2 μg/head)

PBS

CpG30(S)a-mTRP2pep9
(peptide; 200 ng, CpG; 1.7 μg/head)

CpG30(S)a-mTRP2pep9
(peptide; 200 ng, CpG; 1.7 μg/head)
2 times admistration

CpG30(S)a2-mTRP2pep9
(peptide; 200 ng, CpG; 1.7 μg)

CpG30(S)a2-Pen-mTRP2pep8
(peptide; 200 ng, CpG; 1.7 μg)

IMMUNE INDUCER CONTAINING POLYNUCLEOTIDE-PEPTIDE CONJUGATE AND PHARMACEUTICAL COMPOSITION CONTAINING SAME

TECHNICAL FIELD

The present invention relates to an immunity-inducing agent comprising a polynucleotide-peptide conjugate as an active component, a pharmaceutical composition comprising the same, and the like.

BACKGROUND ART

It is known that a family of Toll-like receptors (TLRs), present on antigen-presenting cells such as dendritic cells, macrophages and B cells, can respond to various pathogens, induce cytokine production, and induce acquired immunity through, for example, promotion of differentiation of naïve T cells into Th1 cells, and activation of killer T cells. Pathogens recognized by the series of TLRs are composed of a wide variety of constituents. One of those constituents is a DNA having a CpG motif (CpG DNA), which acts as a ligand for TLR9. CpG motifs are nucleotide sequences basically composed of six nucleotides, in which cytosine (C) and guanine (G) are situated side-by-side at the center and flanked by two purine nucleotides and two pyrimidine nucleotides, and are represented by -PuPu-CG-PyPy- (Pu represents a purine nucleotide, and Py represents a pyrimidine nucleotide) (in humans, GTCGTT is also known to have ligand activity against TLR9), which nucleotide sequences are rare in mammals, and abundant in bacteria. In mammals, most of rare CpG motifs are methylated. Unmethylated CpG motifs, which are rarely observed in mammals, have potent immunostimulatory activity (vid., e.g., NPLs 1 to 3). CpG DNA incorporated into cells by endocytosis is recognized by TLR9 present in the phagosome-like endoplasmic reticulum, and can induce production of Th1 cytokines such as interferon-γ (IFN-γ) and interleukin-2 (IL-2) and induce strong Th1 responses. Th1 responses suppress Th2-dominated allergic responses, and also have potent antitumor activity through cellular immunity by activating macrophages or cytotoxic T lymphocytes (CTL).

CpG DNA is expected to be used not only for infection prevention but also as an adjuvant for allergic and neoplastic diseases. For example, the following reports have been available regarding conjugates in which CpG DNA is covalently bonded to an antigen.

NPL 4 discloses that conjugates of CpG DNA and 18- to 24-mer peptides derived from ovalbumin (OVA) antigen enhanced uptake in dendritic cells and antigen presentation.

NPLs 5 and 6 disclose that conjugates of CpG DNA and OVA antigen protein induced in vitro activation of T cells. Also, NPL 5 discloses that those conjugates induced in vivo antigen-specific cytotoxic activity.

NPL 7 discloses a method for preparing a conjugate of a CpG oligonucleotide and tumor-associated protein or cells.

PTL 1 discloses an immunity-inducing agent comprising, as an active component, a conjugate of a single-chain polynucleotide or polynucleotide derivative comprising a CpG motif, and an antigenic peptide, and also discloses that said immunity-inducing agent has high antigen-specific immunity induction activity.

CITATION LIST

Patent Literature

PTL 1: PCT/JP 2019/038090

Non Patent Literatures

NPL 1: Bacterial CpG DNA Activates Immune Cells to Signal Infectious Danger. H. Wagner, *Adv. Immunol.,* 73, 329-368 (1999).

NPL 2: CpG Motifs in Bacterial DNA and Their Immune Effects. M. Krieg, *Annu. Rev. Immunol.,* 20, 709-760 (2002).

NPL 3: The discovery of immunostimulatory DNA sequence. S. Yamamoto, T. Yamamoto, and T. Tokunaga, *Springer Seminars in Immunopathology,* 22, 11-19 (2000).

NPL 4: Distinct Uptake Mechanisms but Similar Intracellular Processing of Two Different Toll-like Receptor Ligand-Peptide Conjugates in Dendritic Cells. Khan S. et al., J. Biol. Chem. 282, 21145-21159 (2007).

NPL 5: Intracellular Cleavable CpG Oligodeoxynucleotide-Antigen Conjugate Enhances Anti-tumor Immunity. Kramer K., et al., *Mol. Ther.,* 25, 62-70 (2017).

NPL 6: Comparative Study of 5'- and 3'-Linked CpG-Antigen Conjugates for the Induction of Cellular Immune Responses. Kramer K., et al., *ACS Omega,* 2(1), 227-235 (2017).

NPL 7: TLR-9 Agonist Immunostimulatory Sequence Adjuvants Linked to Cancer Antigens. Shirota H. and Klinman D. M., *Methods Mol. Biol.,* 1139, 337-344 (2014).

SUMMARY OF INVENTION

Technical Problem

As disclosed in PTL 1, the present inventors demonstrated as a result of the studies using OVA-derived antigenic peptides that CpG DNA-peptide conjugates have high cytotoxic T lymphocyte (CTL)-inducing ability. In contrast, the inventors found that among similar CpG DNA-peptide conjugates prepared with other antigenic peptides, some may not have adequate CTL-inducing ability. An object of the present invention resides in providing immunity-inducing agents and the like capable of inducing CTL activity, which can be prepared with a wider variety of antigenic peptides.

Solution to Problem

The present inventors have studied peptides which do not show adequate CTL-inducing ability when made into CpG DNA-peptide conjugates, and as a result, found that when an amino acid such as cysteine is added to the N-terminus of a peptide for the purpose of conjugation, the peptide which is inherently able to bind to MHC molecules (i.e., MHC-binding peptide) becomes no longer able to bind to MHC molecules. The inventors also found that a CpG DNA-peptide conjugate having high CTL-inducing ability can be prepared by using not a peptide modified by adding an amino acid such as cysteine directly to the N-terminus of an MHC-binding peptide, but a peptide modified by substituting one or more contiguous N-terminal amino acids containing no anchor residues with an amino acid such as cysteine. The inventors have conducted further intensive studies and completed the present invention.

More specifically, the present invention includes the following embodiments.

[1] An immunity-inducing agent comprising a polynucleotide-peptide conjugate or a pharmaceutically acceptable salt thereof as an active component, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

[2] The immunity-inducing agent as set forth in [1], wherein one or both of the covalent bond between the spacer and the polynucleotide or polynucleotide derivative, and the covalent bond between the spacer and the peptide are a covalent bond or bonds cleavable in biological environment.

[3] The immunity-inducing agent as set forth in [1] or [2], wherein the amino acid having a reactive functional group which allows for the formation of a covalent bond with the spacer is cysteine or an analogue thereof having a thiol group.

[4] The immunity-inducing agent as set forth in any one of [1] to [3], wherein the covalent bond between the spacer and the peptide is a disulfide bond.

[5] The immunity-inducing agent as set forth in any one of [1] to [4], wherein the MHC-binding peptide is an MHC-1-binding peptide.

[6] The immunity-inducing agent as set forth in [5], wherein the MHC-1-binding peptide is an HLA-A-binding peptide or an HLA-B-binding peptide.

[7] The immunity-inducing agent as set forth in [5] or [6], wherein the MHC-1-binding peptide has an amino acid length of not less than 8 and not more than 11.

[8] The immunity-inducing agent as set forth in any one of [1] to [4], wherein the MHC-binding peptide is an MHC-2-binding peptide.

[9] The immunity-inducing agent as set forth in any one of [1] to [8], wherein the polynucleotide or polynucleotide derivative is a polydeoxyribonucleotide (DNA) or DNA derivative comprising two or more CpG motifs.

[10] The immunity-inducing agent as set forth in any one of [1] to [9], wherein the polynucleotide or polynucleotide derivative has a nucleotide length of not less than 15 and not more than 40.

[11] The immunity-inducing agent as set forth in [10], wherein the polynucleotide or polynucleotide derivative has a nucleotide length of not less than 20 and not more than 30.

[12] The immunity-inducing agent as set forth in any one of [1] to [11], wherein the polynucleotide or polynucleotide derivative is a polynucleotide derivative in which phosphodiester bonds are at least partially substituted with phosphorothioate bonds.

[13] The immunity-inducing agent as set forth in [12], wherein, in the polynucleotide derivative in which phosphodiester bonds are at least partially substituted with phosphorothioate bonds, not less than 50% of the phosphodiester bonds are substituted with phosphorothioate bonds.

[14] The immunity-inducing agent as set forth in [13], wherein, in the polynucleotide derivative in which phosphodiester bonds are at least partially substituted with phosphorothioate bonds, not less than 90% of the phosphodiester bonds are substituted with phosphorothioate bonds.

[15] The immunity-inducing agent as set forth in any one of [1] to [14], wherein the spacer comprises repeating units represented by the following formula:

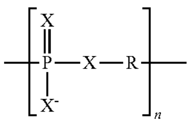

wherein

X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

[16] The immunity-inducing agent as set forth in any one of [1] to [15], wherein the spacer has a structure represented by any of the following formulas.

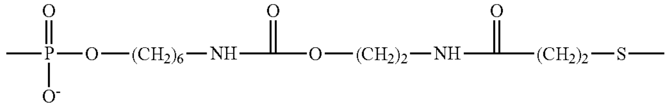

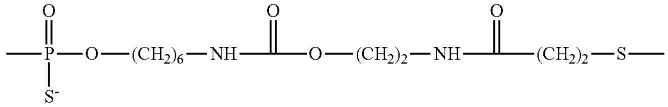

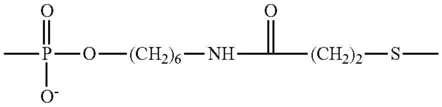

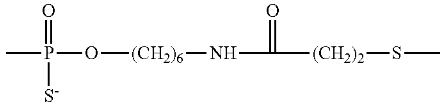

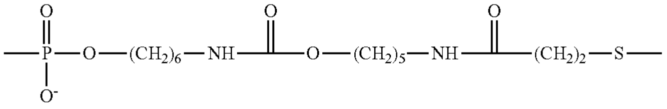

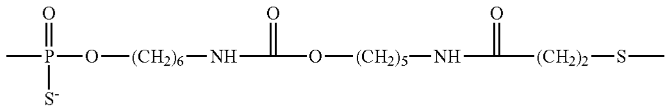

-continued

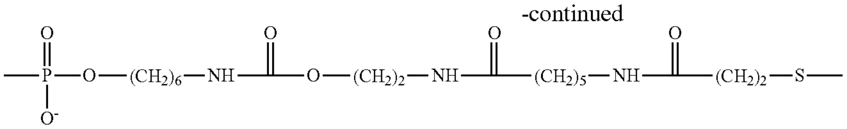

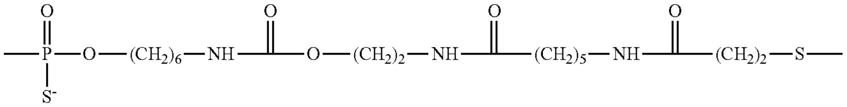

[17] The immunity-inducing agent as set forth in any one of [1] to [14], wherein the spacer has a structure represented by any of the following formulas.

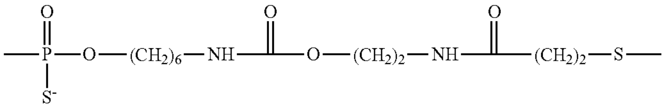

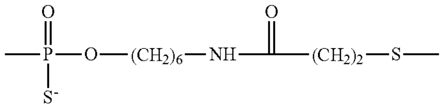

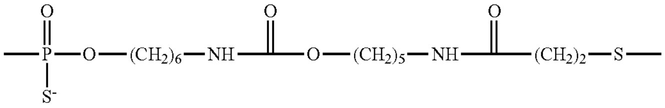

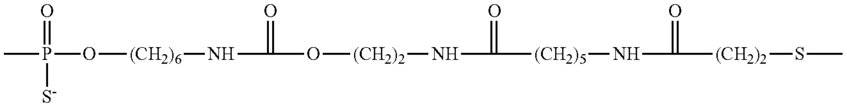

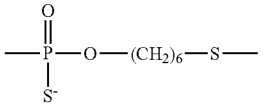

[18] The immunity-inducing agent comprising a polynucleotide-peptide conjugate or a pharmaceutically acceptable salt thereof as an active component, as set forth in [1],
- wherein one or both of the covalent bond between the spacer and the polynucleotide or polynucleotide derivative, and the covalent bond between the spacer and the peptide are a covalent bond or bonds cleavable in biological environment,
- wherein the polynucleotide or polynucleotide derivative is a polydeoxyribonucleotide (DNA) or DNA derivative comprising two or more CpG motifs,
- wherein the polynucleotide or polynucleotide derivative is a polynucleotide derivative in which phosphodiester bonds are at least partially substituted with phosphorothioate bonds.

[19] The immunity-inducing agent comprising a polynucleotide-peptide conjugate or a pharmaceutically acceptable salt thereof as an active component, as set forth in [1],
- wherein the amino acid having a reactive functional group which allows for the formation of a covalent bond with the spacer is cysteine or an analogue thereof having a thiol group,
- wherein the covalent bond between the spacer and the peptide is a disulfide bond,
- wherein the MHC-binding peptide is an MHC-1-binding peptide,
- wherein the MHC-1-binding peptide is an HLA-A-binding peptide or an HLA-B-binding peptide,
- wherein the MHC-1-binding peptide has an amino acid length of not less than 8 and not more than 11,
- wherein the polynucleotide or polynucleotide derivative is a polydeoxyribonucleotide (DNA) or DNA derivative comprising two or more CpG motifs,
- wherein the polynucleotide or polynucleotide derivative has a nucleotide length of not less than 20 and not more than 30,
- wherein, in the polynucleotide derivative in which phosphodiester bonds are at least partially substituted with phosphorothioate bonds, not less than 90% of the phosphodiester bonds are substituted with phosphorothioate bonds,
- wherein the spacer has a structure represented by any of the following formulas.

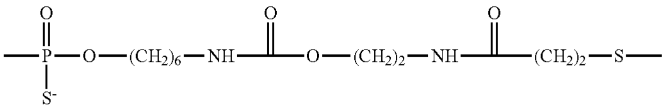

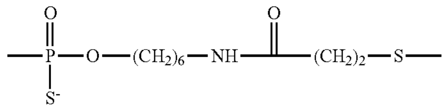

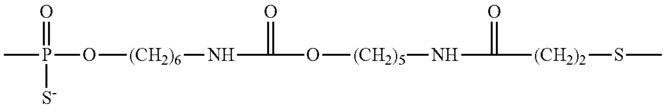

-continued

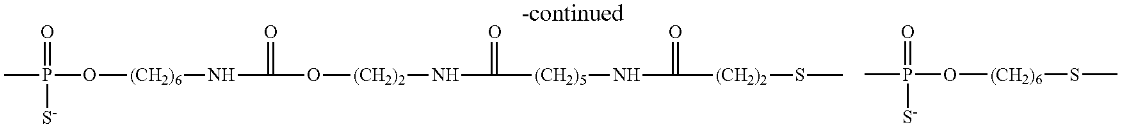

[20] The immunity-inducing agent as set forth in any one of [1] to [19], further comprising a substance having immunostimulatory activity as an adjuvant.

[21] A pharmaceutical composition comprising the immunity-inducing agent as set forth in any one of [1] to [20].

[22] The pharmaceutical composition as set forth in [21], for the treatment or prevention of infections, tumors, or allergic diseases.

[23] The pharmaceutical composition as set forth in [21], for the treatment or prevention of tumors.

[24] A method for treating or preventing infections, tumors, or allergic diseases, the method comprising administering the immunity-inducing agent as set forth in any one of [1] to [20] to a patient.

[25] A method for treating or preventing tumors, the method comprising administering the immunity-inducing agent as set forth in any one of [1] to [20] to a patient.

[26] The immunity-inducing agent as set forth in any one of [1] to [20], for use in the treatment or prevention of infections, tumors, or allergic diseases.

[27] The immunity-inducing agent as set forth in any one of [1] to [20], for use in the treatment or prevention of tumors.

[28] Use of the immunity-inducing agent as set forth in any one of [1] to [20] for the manufacture of a medicament for the treatment or prevention of infections, tumors, or allergic diseases.

[29] Use of the immunity-inducing agent as set forth in any one of [1] to [20] for the manufacture of a medicament for the treatment or prevention of tumors.

[30] A polynucleotide-peptide conjugate or a pharmaceutically acceptable salt thereof, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

[31] The polynucleotide-peptide conjugate or a pharmaceutically acceptable salt thereof as set forth in [30], wherein one or both of the covalent bond between the spacer and the polynucleotide or polynucleotide derivative, and the covalent bond between the spacer and the peptide are a covalent bond or bonds cleavable in biological environment, wherein the polynucleotide or polynucleotide derivative is a polydeoxyribonucleotide (DNA) or DNA derivative comprising two or more CpG motifs, wherein the polynucleotide or polynucleotide derivative is a polynucleotide derivative in which phosphodiester bonds are at least partially substituted with phosphorothioate bonds.

[32] The polynucleotide-peptide conjugate or a pharmaceutically acceptable salt thereof as set forth in [30], wherein the amino acid having a reactive functional group which allows for the formation of a covalent bond with the spacer is cysteine or an analogue thereof having a thiol group, wherein the covalent bond between the spacer and the peptide is a disulfide bond, wherein the MHC-binding peptide is an MHC-1-binding peptide, wherein the MHC-1-binding peptide is an HLA-A-binding peptide or an HLA-B-binding peptide, wherein the MHC-1-binding peptide has an amino acid length of not less than 8 and not more than 11, wherein the polynucleotide or polynucleotide derivative is a polydeoxyribonucleotide (DNA) or DNA derivative comprising two or more CpG motifs, wherein the polynucleotide or polynucleotide derivative has a nucleotide length of not less than 20 and not more than 30, wherein, in the polynucleotide derivative in which phosphodiester bonds are at least partially substituted with phosphorothioate bonds, not less than 90% of the phosphodiester bonds are substituted with phosphorothioate bonds, wherein the spacer has a structure represented by any of the following formulas.

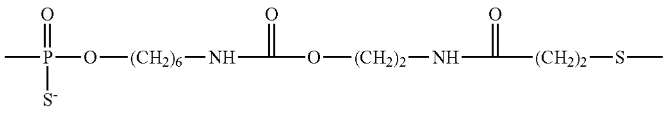

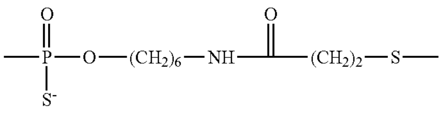

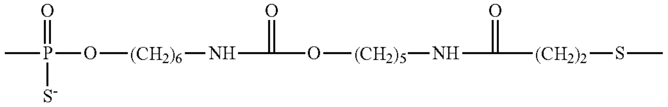

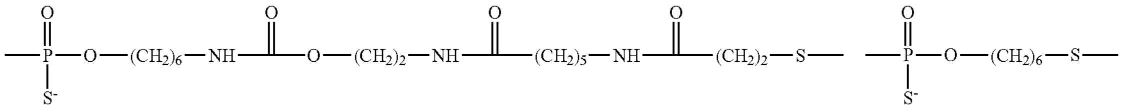

Further, the present invention provides [A1] to [A19] as mentioned below.

[A1] A polynucleotide-peptide conjugate or a pharmaceutically acceptable salt thereof, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

[A2] The polynucleotide-peptide conjugate or a pharmaceutically acceptable salt thereof as set forth in [A1], wherein one or both of the covalent bond between the spacer and the polynucleotide or polynucleotide derivative, and the covalent bond between the spacer and the peptide are a covalent bond or bonds cleavable in biological environment.

[A3] The polynucleotide-peptide conjugate or a pharmaceutically acceptable salt thereof as set forth in [A1] or [A2], wherein the amino acid having a reactive functional group which allows for the formation of a covalent bond with the spacer is cysteine or an analogue thereof having a thiol group.

[A4] The polynucleotide-peptide conjugate or a pharmaceutically acceptable salt thereof as set forth in any one of [A1] to [A3], wherein the covalent bond between the spacer and the peptide is a disulfide bond.

[A5] The polynucleotide-peptide conjugate or a pharmaceutically acceptable salt thereof as set forth in any one of [A1] to [A4], wherein the MHC-binding peptide is an MHC-1-binding peptide.

[A6] The polynucleotide-peptide conjugate or a pharmaceutically acceptable salt thereof as set forth in [A5], wherein the MHC-1-binding peptide is an HLA-A-binding peptide or an HLA-B-binding peptide.

[A7] The polynucleotide-peptide conjugate or a pharmaceutically acceptable salt thereof as set forth in [A5] or [A6], wherein the MHC-1-binding peptide has an amino acid length of not less than 8 and not more than 11.

[A8] The polynucleotide-peptide conjugate or a pharmaceutically acceptable salt thereof as set forth in any one of [A1] to [A4], wherein the MHC-binding peptide is an MHC-2-binding peptide.

[A9] The polynucleotide-peptide conjugate or a pharmaceutically acceptable salt thereof as set forth in any one of [A1] to [A8], wherein the polynucleotide or polynucleotide derivative is a polydeoxyribonucleotide (DNA) or DNA derivative comprising two or more CpG motifs.

[A10] The polynucleotide-peptide conjugate or a pharmaceutically acceptable salt thereof as set forth in any one of [A1] to [A9], wherein the polynucleotide or polynucleotide derivative has a nucleotide length of not less than 15 and not more than 40.

[A11] The polynucleotide-peptide conjugate or a pharmaceutically acceptable salt thereof as set forth in [A10], wherein the polynucleotide or polynucleotide derivative has a nucleotide length of not less than 20 and not more than 30.

[A12] The polynucleotide-peptide conjugate or a pharmaceutically acceptable salt thereof as set forth in any one of [A1] to [A11], wherein the polynucleotide or polynucleotide derivative is a polynucleotide derivative in which phosphodiester bonds are at least partially substituted with phosphorothioate bonds.

[A13] The polynucleotide-peptide conjugate or a pharmaceutically acceptable salt thereof as set forth in [A12], wherein, in the polynucleotide derivative in which phosphodiester bonds are at least partially substituted with phosphorothioate bonds, not less than 50% of the phosphodiester bonds are substituted with phosphorothioate bonds.

[A14] The polynucleotide-peptide conjugate or a pharmaceutically acceptable salt thereof as set forth in [A13], wherein, in the polynucleotide derivative in which phosphodiester bonds are at least partially substituted with phosphorothioate bonds, not less than 90% of the phosphodiester bonds are substituted with phosphorothioate bonds.

[A15] The polynucleotide-peptide conjugate or a pharmaceutically acceptable salt thereof as set forth in any one of [A1] to [A14], wherein the spacer comprises repeating units represented by the following formula:

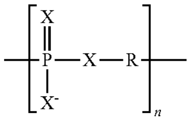

wherein

X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

[A16] The polynucleotide-peptide conjugate or a pharmaceutically acceptable salt thereof as set forth in any one of [A1] to [A15], wherein the spacer has a structure represented by any of the following formulas.

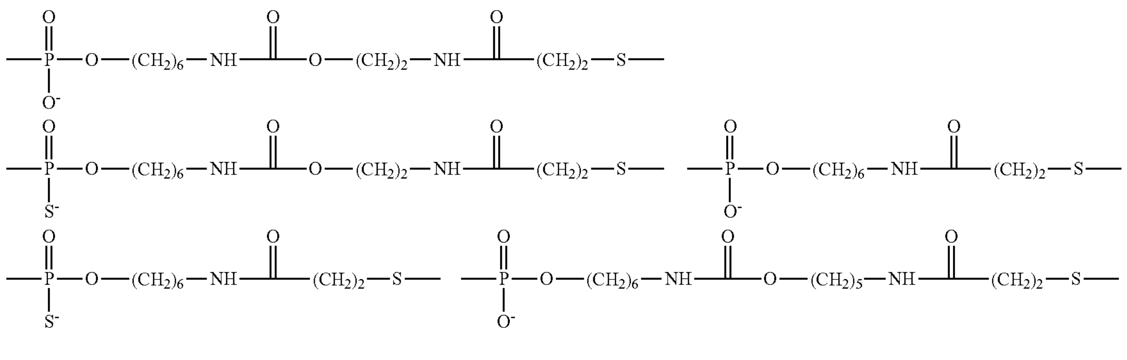

-continued

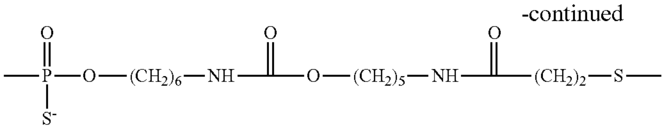

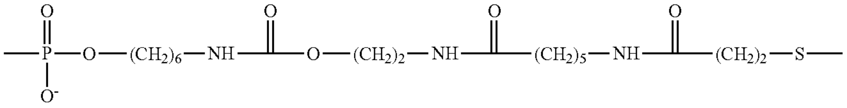

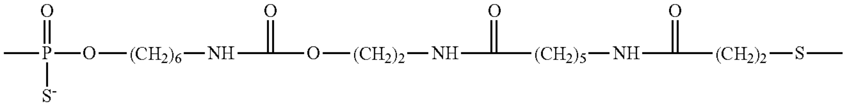

[A17] The polynucleotide-peptide conjugate or a pharmaceutically acceptable salt thereof as set forth in any one of [A1] to [A14], wherein the spacer has a structure represented by any of the following formulas.

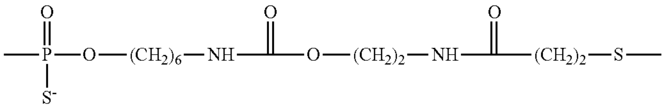

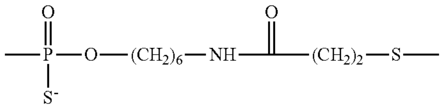

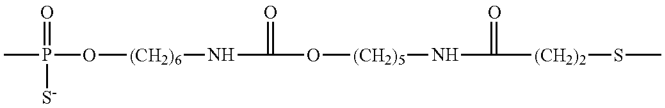

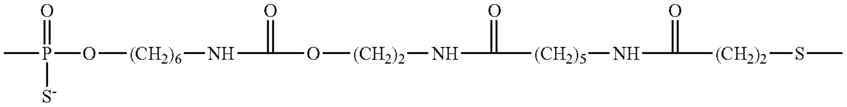

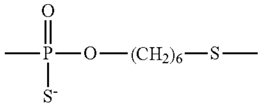

[A18] The polynucleotide-peptide conjugate or a pharmaceutically acceptable salt thereof as set forth in [A1], wherein one or both of the covalent bond between the spacer and the polynucleotide or polynucleotide derivative, and the covalent bond between the spacer and the peptide are a covalent bond or bonds cleavable in biological environment, wherein the polynucleotide or polynucleotide derivative is a polydeoxyribonucleotide (DNA) or DNA derivative comprising two or more CpG motifs, wherein the polynucleotide or polynucleotide derivative is a polynucleotide derivative in which phosphodiester bonds are at least partially substituted with phosphorothioate bonds.

[A19] The polynucleotide-peptide conjugate or a pharmaceutically acceptable salt thereof as set forth in [A1], wherein the amino acid having a reactive functional group which allows for the formation of a covalent bond with the spacer is cysteine or an analogue thereof having a thiol group, wherein the covalent bond between the spacer and the peptide is a disulfide bond, wherein the MHC-binding peptide is an MHC-1-binding peptide, wherein the MHC-1-binding peptide is an HLA-A-binding peptide or an HLA-B-binding peptide, wherein the MHC-1-binding peptide has an amino acid length of not less than 8 and not more than 11, wherein the polynucleotide or polynucleotide derivative is a polydeoxyribonucleotide (DNA) or DNA derivative comprising two or more CpG motifs, wherein the polynucleotide or polynucleotide derivative has a nucleotide length of not less than 20 and not more than 30, wherein, in the polynucleotide derivative in which phosphodiester bonds are at least partially substituted with phosphorothioate bonds, not less than 90% of the phosphodiester bonds are substituted with phosphorothioate bonds, wherein the spacer has a structure represented by any of the following formulas.

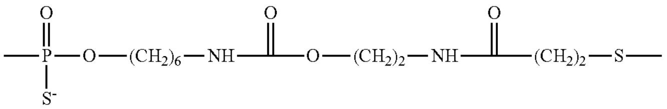

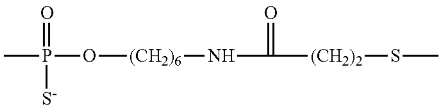

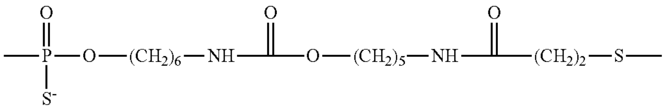

-continued

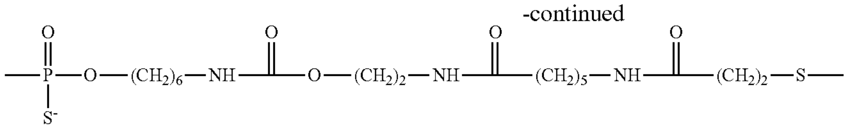

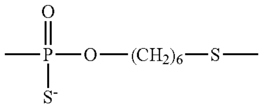

Further, the present invention provides [A20] and [A21] as mentioned below.

[A20] A method for producing an immunity-inducing agent comprising a polynucleotide-peptide conjugate or a pharmaceutically acceptable salt thereof as an active component, the method comprising:

(1) preparing a single-chain polynucleotide or polynucleotide derivative comprising a CpG motif;

(2) preparing a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues; and (3) coupling the polynucleotide or polynucleotide derivative prepared in (1) and the peptide prepared in (2) via a spacer, wherein the spacer is covalently bonded at one end thereof to the polynucleotide or polynucleotide derivative and covalently bonded at the other end thereof to the peptide.

[A21] The method as set forth in [A20], wherein the immunity-inducing agent is the immunity-inducing agent as set forth in any one of [1] to [20], [26], and [27].

Further, the present invention provides [A22] and [A23] as mentioned below.

[A22] A method for producing a polynucleotide-peptide conjugate or a pharmaceutically acceptable salt thereof, the method comprising:

(1) preparing a single-chain polynucleotide or polynucleotide derivative comprising a CpG motif;

(2) preparing a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues; and (3) coupling the polynucleotide or polynucleotide derivative prepared in (1) and the peptide prepared in (2) via a spacer, wherein the spacer is covalently bonded at one end thereof to the polynucleotide or polynucleotide derivative and covalently bonded at the other end thereof to the peptide.

[A23] The method as set forth in [A22], wherein the polynucleotide-peptide conjugate or the pharmaceutically acceptable salt thereof is the polynucleotide-peptide conjugate or the pharmaceutically acceptable salt thereof as set forth in any one of [A1] to [A19].

Further, the present invention provides [a1] to [a19] as mentioned below.

[a1] An immunity-inducing agent comprising a polynucleotide-peptide conjugate or a pharmaceutically acceptable salt thereof as an active component, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

[a2] The immunity-inducing agent as set forth in [a1], wherein one or both of the covalent bond between the spacer and the polynucleotide or polynucleotide derivative, and the covalent bond between the spacer and the peptide are a covalent bond or bonds cleavable in biological environment.

[a3] The immunity-inducing agent as set forth in [a1] or [a2], wherein the amino acid having a reactive functional group which allows for the formation of a covalent bond with the spacer is cysteine or an analogue thereof having a thiol group.

[a4] The immunity-inducing agent as set forth in any one of [a1] to [a3], wherein the covalent bond between the spacer and the peptide is a disulfide bond.

[a5] The immunity-inducing agent as set forth in any one of [a1] to [a4], wherein the MHC-binding peptide is an MHC-1-binding peptide.

[a6] The immunity-inducing agent as set forth in [a5], wherein the MHC-1-binding peptide is an HLA-A-binding peptide or an HLA-B-binding peptide.

[a7] The immunity-inducing agent as set forth in [a5] or [a6], wherein the MHC-1-binding peptide has an amino acid length of not less than 8 and not more than 11.

[a8] The immunity-inducing agent as set forth in any one of [a1] to [a4], wherein the MHC-binding peptide is an MHC-2-binding peptide.

[a9] The immunity-inducing agent as set forth in any one of [a1] to [a8], wherein the polynucleotide or polynucleotide derivative is a polydeoxyribonucleotide (DNA) or DNA derivative comprising two or more CpG motifs.

[a10] The immunity-inducing agent as set forth in any one of [a1] to [a9], wherein the polynucleotide or polynucleotide derivative has a nucleotide length of not less than 15 and not more than 40.

[a11] The immunity-inducing agent as set forth in [a10], wherein the polynucleotide or polynucleotide derivative has a nucleotide length of not less than 20 and not more than 30.

[a12] The immunity-inducing agent as set forth in any one of [a1] to [a11], wherein the polynucleotide or polynucleotide derivative is a polynucleotide derivative in which phosphodiester bonds are at least partially substituted with phosphorothioate bonds.

[a13] The immunity-inducing agent as set forth in [a12], wherein, in the polynucleotide derivative in which phosphodiester bonds are at least partially substituted with phosphorothioate bonds, not less than 50% of the phosphodiester bonds are substituted with phosphorothioate bonds.

[a14] The immunity-inducing agent as set forth in [a13], wherein, in the polynucleotide derivative in which phosphodiester bonds are at least partially substituted with phosphorothioate bonds, not less than 90% of the phosphodiester bonds are substituted with phosphorothioate bonds.

[a15] The immunity-inducing agent as set forth in any one of [a1] to [a14], wherein the spacer comprises repeating units represented by the following formula:

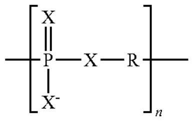

wherein

X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

[a16] The immunity-inducing agent as set forth in any one of [a1] to [a15], wherein the spacer has a structure represented by any of the following formulas.

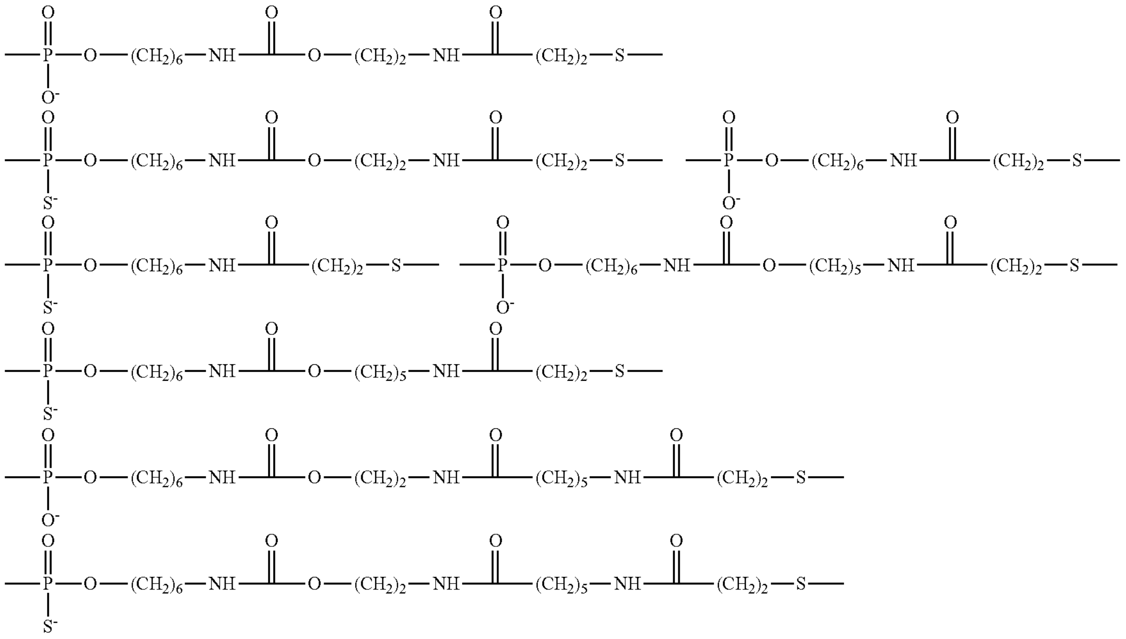

[a17] The immunity-inducing agent as set forth in any one of [a1] to [a16], further comprising a substance having immunostimulatory activity as an adjuvant.

[a18] A pharmaceutical composition comprising the immunity-inducing agent as set forth in any one of [a1] to [a17].

[a19] The pharmaceutical composition as set forth in [a18], for the treatment of tumors.

Advantageous Effects of Invention

According to the present invention, a wide variety of antigenic peptides can be used to prepare immunity-inducing agents capable of inducing CTL activity.

DESCRIPTION OF EMBODIMENTS

Figure 1:
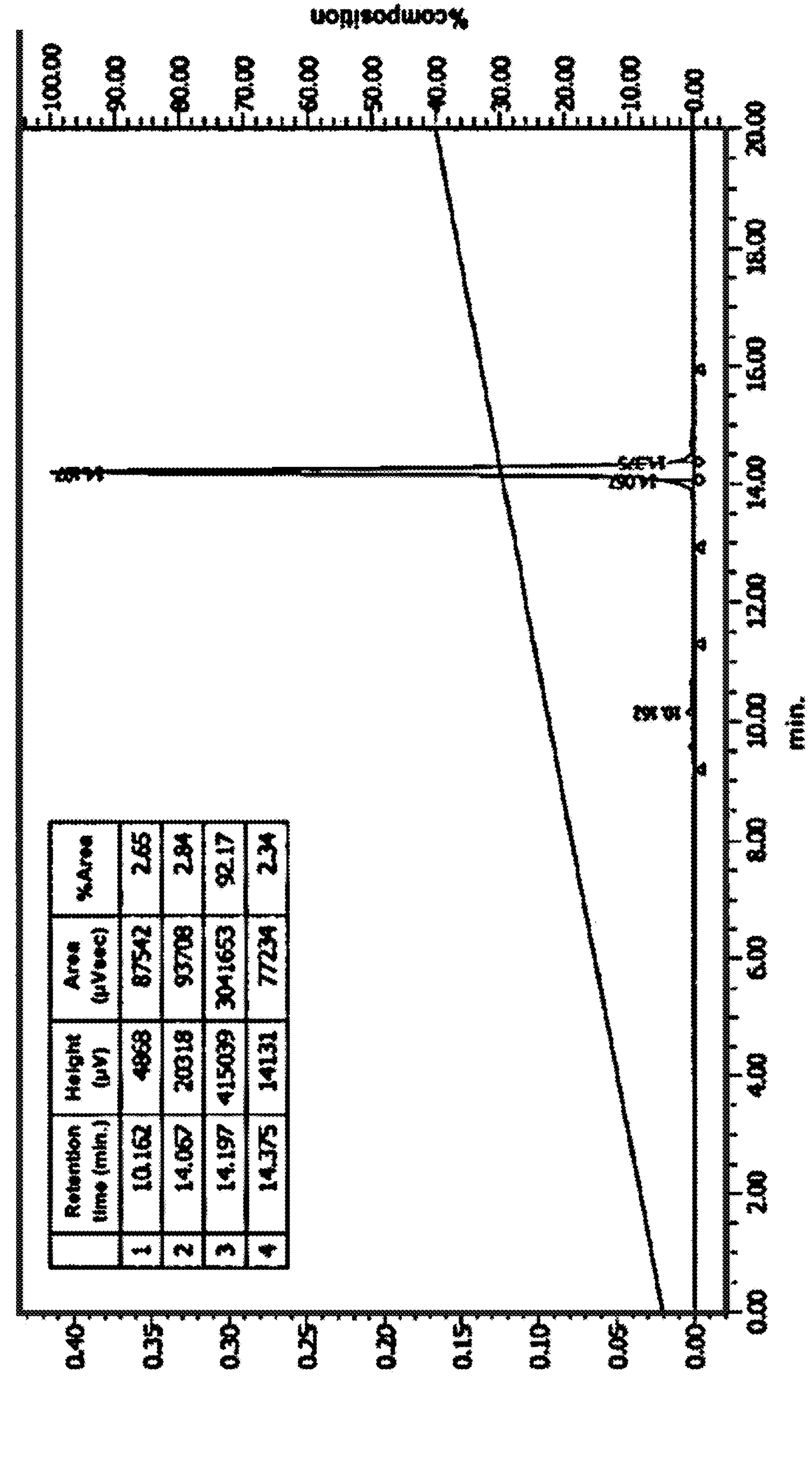
FIG. 1 depicts the chromatogram obtained by the HPLC analysis of CpG30(S)a-mTRP2pep9 (Compound 1) performed in Example 1.

The present invention provides an immunity-inducing agent comprising a polynucleotide-peptide conjugate or a pharmaceutically acceptable salt thereof as an active component (hereinafter also referred to as "the immunity-inducing agent of the present [this] invention").

In the immunity-inducing agent of the present invention, the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide.

As the "single-chain polynucleotide or polynucleotide derivative comprising a CpG motif", any polynucleotide or polynucleotide derivative having any nucleotide sequence consisting of any numbers of nucleotides can be used without particular limitation, as long as it comprises one or two or more (preferably two or more, e.g., 2, 3, 4, 5 or 6) CpG motifs. Specific examples of CpG motifs include AGCGTT, GACGTT, GACGTC, GTCGTT, and the like. Two or more CpG motifs having different sequences may be contained in the polynucleotide. The number of CpG motifs contained in the polynucleotide is not particularly limited, but preferably one to six CpG motifs, more preferably two to four CpG motifs, are contained in the polynucleotide. The polynucleotide or polynucleotide derivative is preferably a polydeoxyribonucleotide (DNA) or a phosphorothioate-modified DNA derivative comprising two or more CpG motifs, but may be partially composed of an RNA or an RNA derivative. When an RNA or an RNA derivative is contained, the content of the RNA or RNA derivative is preferably not more than 20% (specifically not more than 20, 19, 18, 17, 16, 15, 14, 13, 12, 11, 10, 9, 8, 7, 6, 5, 4, 3, 2 or 1%) in terms of percentage of the number of nucleotides.

The number of nucleotides contained in the polynucleotide or polynucleotide derivative is in the range of preferably from 15 to 40 (specifically 15, 16, 17, 18, 19, 20, 21, 22, 23, 24, 25, 26, 27, 28, 29, 30, 31, 32, 33, 34, 35, 36, 37, 38, 39 or 40), more preferably from 20 to 30 (specifically 20, 21, 22, 23, 24, 25, 26, 27, 28, 29 or 30). Specific examples of the nucleotide sequences of preferred polynucleotides or polynucleotide derivatives include those listed in Table 1 below. In Table 1, the underlined sequences represent CpG motifs.

TABLE 1

| | DNA (5'→3') containing a CpG motif (s) | SEQ ID NO. |
|---|---|---|
| K3 | ATCGACTCTCGAGCGTTCTC | 1 |
| K3-20 (b) | GAGCGTTCTCGAGCGTTCTC | 2 |
| K3-21 | CGAGCGTTCTCGAGCGTTCTC | 3 |
| K3-24 | TCTCGAGCGTTCTCGAGCGTTCTC | 4 |
| K3-27 | GACTCTCGAGCGTTCTCGAGCGTTCTC | 5 |
| K3-30 (a) | GAGCGTTCTCATCGACTCTCGAGCGTTCTC | 6 |
| K3-30 (b) | ATCGACTCTCGAGCGTTCTCGAGCGTTCTC | 7 |
| K3-40 | ATCGACTCTCGAGCGTTCTCATCGACTCTCGAGCGTTCTC | 8 |
| K3-30 (c) | CTCAGCGTTCTCAGCGTTCTCAGCGTTCTC | 9 |
| K3-30 (d) | TTTAGCGTTTTTAGCGTTTTTAGCGTTTTT | 10 |
| K3-30 (e) | TTAGCGTTTAGCGTTTAGCGTTTAGCGTTT | 11 |
| K3-30 (f) | TTAGCGTTCAGCGTTCAGCGTTCAGCGTTT | 12 |
| K3-26 (a) | TCAGCGTTTCAGCGTTTCAGCGTTTC | 13 |
| K3-26 (b) | TTAGCGTTTTAGCGTTTTAGCGTTTT | 14 |
| ODN1668 | TCCATGACGTTCCTGATGCT | 15 |
| ODN1668-30 | TGACGTTCCTTCCATGACGTTCCTGATGCT | 16 |
| ODN1668-40 | TCCATGACGTTCCTGATGCTTCCATGACGTTCCTGATGCT | 17 |
| ODN1826 | TCCATGACGTTCCTGACGTT | 18 |
| ODN1826-30 | TGACGTTCCTTCCATGACGTTCCTGACGTT | 19 |
| ODN1826-40 | TCCATGACGTTCCTGACGTTTCCATGACGTTCCTGACGTT | 20 |
| ODN2006 | TCGTCGTTTTGTCGTTTTGTCGTT | 21 |
| ODN2006-30 | GTCGTTTCGTCGTTTTGTCGTTTTGTCGTT | 22 |
| ODN2006-40 | TCGTCGTTTTGTCGTTTCGTCGTTTTGTCGTTTTGTCGTT | 23 |

TABLE 1-continued

| | DNA (5'→3') containing a CpG motif (s) | SEQ ID NO. |
|---|---|---|
| ODN684 | TCGACGTTCGTCGTTCGTCGTTC | 24 |
| ODN684-30 | TCGTCGTTCGACGTTCGTCGTTCGTCGTTC | 25 |
| ODN684-40 | GTTCGTCGTTTCGTCGTTCGACGTTCGTCGTTCGTCGTTC | 26 |
| ODN D-SL01 | TCGCGACGTTCGCCCGACGTTCGGTA | 27 |
| ODN D-SL01-35 | TCGCGACGTTCGCGACGTTCGCCCGACGTTCGGTA | 28 |
| C-CpG_1 | TCGAACGTTCGAACGTTCGAACGTTCGAAT | 29 |
| 1018ISS | TGACTGTGAACGTTCGAGATGA | 43 |
| 1018ISS 30 | TGAACGTTCGACTGTGAACGTTCGAGATGA | 44 |
| 1018ISS_40 | TGAACGTTCGTGAACGTTCGACTGTGAACGTTCGAGATGA | 45 |

Since the polynucleotide is susceptible to degradation by nuclease in the living body, a polynucleotide derivative may be used instead of the polynucleotide with the aim of enhancing stability in the living body. The polynucleotide derivative can have any given modification known in the art as a modification for increasing nuclease resistance to enhance stability in the living body. Examples of the polynucleotide derivative include those derivatives in which the hydroxyl groups at the 2' position of a ribonucleotide are completely or partially substituted with fluorine or methoxy groups, those derivatives in which the phosphodiester bonds in a polyribonucleotide (RNA) or a polydeoxyribonucleotide (DNA) are completely or partially substituted with phosphorothioate bonds, and the like. In the case of those derivatives in which the phosphodiester bonds in a polynucleotide or polynucleotide derivative are partially substituted with phosphorothioate bonds, it is preferred that not less than 50% (specifically not less than 50, 60, 70, 80 or 90%) of the phosphodiester bonds should be substituted with phosphorothioate bonds, and it is more preferred that not less than 90% (specifically not less than 90, 91, 92, 93, 94, 95, 96, 97, 98 or 99%) of the phosphodiester bonds should be substituted with phosphorothioate bonds. The phosphodiester bonds may be substantially completely substituted with phosphorothioate bonds. The phosphodiester bonds may be completely substituted with phosphorothioate bonds. The locations of phosphodiester bonds to be substituted with phosphorothioate bonds are not particularly limited. Two or more consecutive phosphodiester bonds may be substituted, or phosphodiester bonds may be substituted so as to ensure that phosphorothioate bonds are not adjacent to each other.

The location at which the polynucleotide or polynucleotide derivative is bonded to the spacer is not particularly limited, and can be, for example, at the 5' end or the 3' end. For covalent bonding between the polynucleotide or polynucleotide derivative and the spacer, any functional groups present in the polynucleotide or polynucleotide derivative can be used as they are, or those functional groups activated by chemical modification can be used. It is preferred that an oxygen atom of the hydroxy group at the 5' end or 3' end of the polynucleotide or polynucleotide derivative should be bonded to the spacer.

The polynucleotide or polynucleotide derivative can be synthesized using a known chemical synthesis method (e.g., phosphotriester method, phosphoramidite method, H-phosphonate method). The polynucleotide or polynucleotide derivative may be synthesized by a commercially available nucleic acid synthesizer using a commercially available reagent used for DNA/RNA synthesis.

In the immunity-inducing agent of the present invention, the "peptide" is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding.

In the present invention, the "MHC-binding peptide" refers to a peptide that can bind to an MHC (major histocompatibility complex) molecule without additional processing such as trimming and can be presented as an antigen to T cells. Examples of MHC molecules include MHC-1 molecules (also referred to as "MHC class I molecules") and MHC-2 molecules (also referred to as "MHC class II molecules"). MHC-1 molecules produced in humans are called "HLA molecules", and there are many HLA alleles. The MHC-binding peptide is preferably a peptide presented as an antigen by an MHC-1 molecule (i.e., MHC-1-binding peptide) or a peptide presented as an antigen by an MHC-2 molecule (i.e., MHC-2-binding peptide), more preferably an MHC-1-binding peptide, still more preferably a peptide presented as an antigen by an HLA-A molecule (i.e., HLA-A-binding peptide) or a peptide presented as an antigen by an HLA-B molecule (i.e., HLA-B-binding peptide).

The MHC-binding peptide can be a peptide derived from a protein responsible for allergies such as food allergy, or a protein from a pathogen such as bacterium or virus, tumor cells, or the like. Examples of MHC-binding peptides include, but are not limited to, the peptides listed in the public database SYFPEITHI (http://www.syfpeithi.de/0-Home.htm; vid., *Immunogenetics* (1999) 50:213-219), and the peptides listed in the table given in *Immunogenetics* (1995) 41:178-228.

Specific examples of MHC-1-binding peptides include OVA peptide 1 (a peptide consisting of amino acid residues 258 to 265 of ovalbumin (OVA; GenBank accession No. CAA23716.1); SIINFEKL (SEQ ID NO: 41)), TRP2-9 (a peptide consisting of amino acid residues 180 to 188 of mTRP2 (GenBank accession No. CAA44951.1)), hGP100-9 (a peptide consisting of amino acid residues 25 to 33 of hGP100 (GenBank accession No. AAC60634.1)), etc.

Specific examples of MHC-2-binding peptides include OVA peptide 2 (a peptide consisting of amino acid residues 324 to 340 of OVA; ISQAVHAAHAEINEAGR (SEQ ID NO: 42)), etc.

MHC molecules have, in their peptide-binding clefts, binding sites called pockets, which interact directly with MHC-binding peptides. In MHC-binding peptides, residues that interact with the particular pockets are called anchor residues or anchor amino acids. The locations of anchor residues can vary depending on the type of the bound MHC molecules. The locations of anchor residues and common motifs depending on the type of MHC molecules can be seen, for example, from the public database MHC Motif Viewer (http://www.cbs.dtu.dk/biotools/MHCMotifViewer/Home.html; vid., *Immunogenetics* (2008) 60:759-765). For example, it is known that in human MHC-1-binding peptides, such as HLA-A- and HLA-B-binding peptides, 2nd and 9th amino acid residues from the N-terminus serve as anchor residues.

MHC-binding peptides include not only peptides that can exist in nature as mentioned above (wild-type peptides), but also peptides that cannot exist in nature and which contain, for example, non-natural amino acids. Examples of such non-natural peptides include modified peptides in which anchor residues are substituted with other amino acids (including non-natural amino acids) for the purpose of enhancing the binding ability to MHC molecules (which are referred to as "heteroclitic peptides") (vid., *Front. Immunol.,* 6:377 (2015), and *J. Immunol.,* 174(8):4812-4820 (2005)).

The amino acid length of an MHC-binding peptide is not particularly limited, and can vary depending on the type of MHC molecules—for example, the MHC-binding peptide can have an amino acid length of not less than 5 and not more than 30. The length of a peptide binding to an MHC-1 molecule is fixed to some extent, and is generally a length of from 8 to 11 amino acids. Therefore, in the present invention, when the MHC-binding peptide is an MHC-1-binding peptide, the MHC-1-binding peptide has an amino acid length of preferably not less than 8 and not more than 11, more preferably 8, 9 or 10, still more preferably 9 or 10.

The present inventors found that when an amino acid such as cysteine is added to the N-terminus of an MHC-binding peptide for the purpose of conjugation, the MHC-binding peptide may become no longer able to bind to MHC molecules (Example 3). It is known that endoplasmic reticulum aminopeptidase (ERAP) is involved in the presentation of an antigenic peptide by MHC-1 molecules. An antigenic peptide precursor is generally trimmed from the N-terminus by ERAP to yield a peptide with a length suitable for binding to MHC-1. However, it is considered possible that a peptide derived from a polynucleotide-peptide conjugate may not be correctly trimmed by ERAP so that the resulting peptide cannot have an inherent structure capable of binding to the peptide-binding clefts of MHC molecules. In contrast, when a peptide is modified by substituting one or more contiguous amino acids at the N-terminus of an MHC-binding peptide with an amino acid having a reactive functional group which allows for the formation of a covalent bond with a spacer while anchor residues are left, the modified peptide is capable of binding to MHC-1 molecules. Further, a polynucleotide-peptide conjugate prepared using such a modified peptide has adequate CTL-inducing ability.

The number of N-terminal amino acids of an MHC-binding peptide substituted with an amino acid having a reactive functional group is not particularly limited as long as the N-terminal amino acids contain no anchor residues for MHC binding, and can be determined, as appropriate, depending on the type of MHC molecules. For example, in the case of a peptide binding to MHC-1 molecules, the number of amino acids substituted can be not more than 4 (i.e., 4, 3, 2 or 1), and is preferably 1. In one embodiment, when the MHC-binding peptide is an HLA-A-binding peptide or an HLA-B-binding peptide, an anchor residue is located at the 2nd position from the N-terminus—thus, the number of amino acids substituted can be 1.

The "amino acid having a reactive functional group which allows for the formation of a covalent bond with a spacer" refers to an amino acid having a reactive functional group capable of forming a covalent bond (e.g., ester bond, amide bond or phosphoester bond) with a spacer, and can be a natural amino acid or a non-natural amino acid. The covalent bond with a spacer is preferably a covalent bond cleavable in biological environment. Examples of such a covalent bond include bonds that are cleaved in intracellular reductive environment, such as disulfide bonds. Other examples thereof include ester bonds, amide bonds (e.g., amide bonds with cathepsin-sensitive peptides), and phosphodiester bonds, which are specifically cleaved by intracellular enzymes such as esterases, peptidases (e.g., cathepsin), and nucleases. In a preferred embodiment, the covalent bond can be a disulfide bond, and the reactive functional group can be a thiol group. In this case, the "amino acid having a reactive functional group which allows for the formation of a covalent bond with a spacer" can be cysteine or an analogue thereof having a thiol group. A cysteine analogue having a thiol group is an amino acid having a side chain containing thiol—the structure of a side chain is not particularly limited. Examples of a cysteine analogue having a thiol group include homocysteine (CAS No: 6027-13-0), penicillamine (β,β-dimethylcysteine; CAS No: 1113-41-3), β-methylcysteine (CAS No: 29768-80-7), and 4-mercapto-norvaline (CAS No: 2351397-00-5).

In the immunity-inducing agent of the present invention, the peptide can be prepared using any known method, such as peptide synthesis.

In the immunity-inducing agent of the present invention, the "spacer" need only have a structure capable of forming a covalent bond with a single-chain polynucleotide or polynucleotide derivative comprising a CpG motif and with a peptide. Examples of the spacer include alkylene group, polyethylene glycol (PEG), and the like. The spacer may comprise repeating units having a phosphodiester structure or phosphorothioate structure, as represented by the following formula.

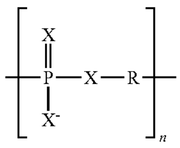

In the formula given above, X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

Since these repeating units do not undergo hydrolysis by nucleases, the stability of the repeating units does not significantly deteriorate even when X is an oxygen atom. For example, when R is $(CH_2)_3O$, the size of the repeating units is nearly equal to that of a ribonucleotide or deoxyribonucleotide—thus, it can be expected that the production cost can be reduced by partially substituting a polynucleotide or polynucleotide derivative with this spacer. Specific examples of the spacer include the following.

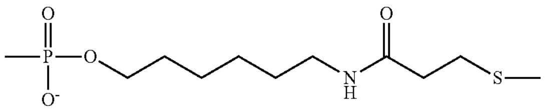
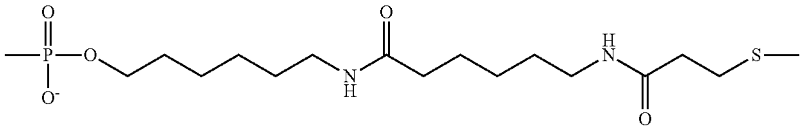
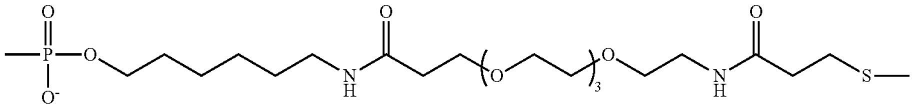
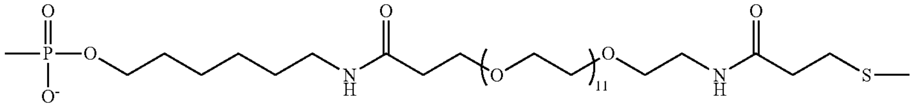
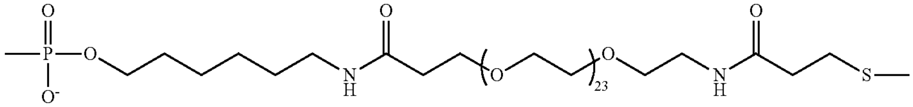
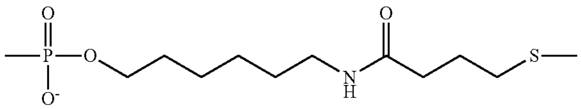
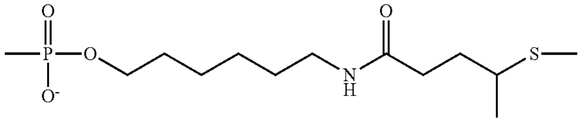
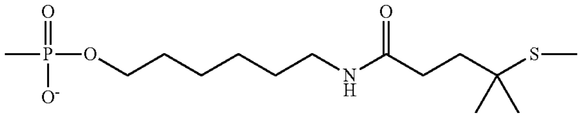
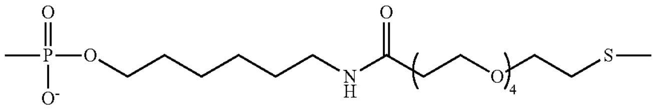
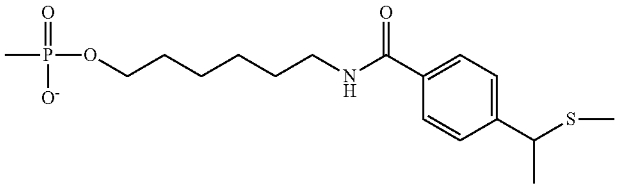
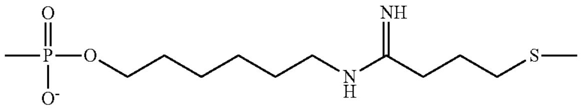
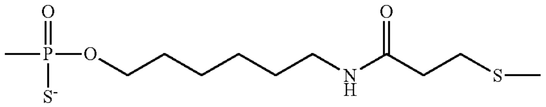
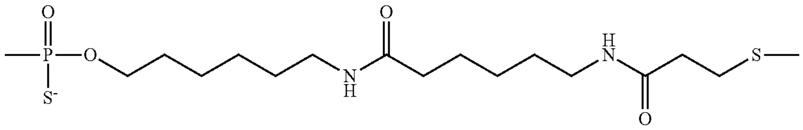
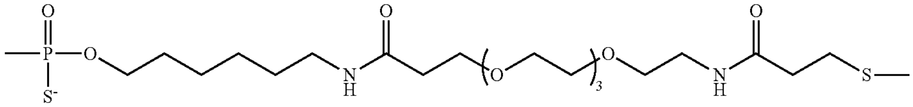

-continued
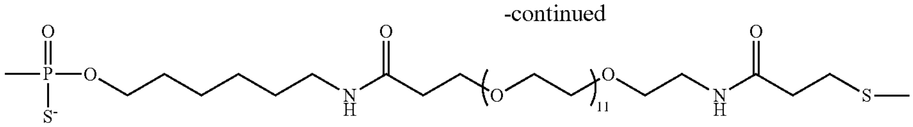
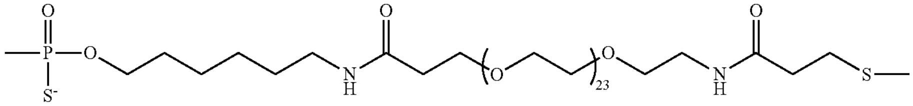
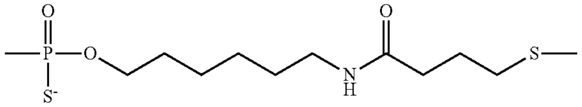
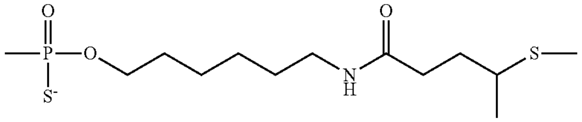
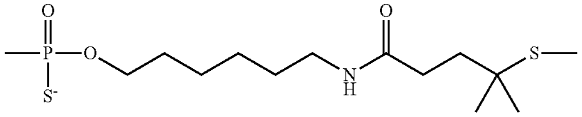
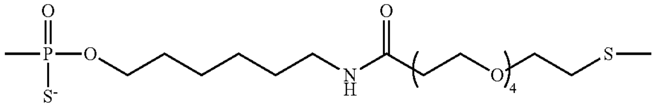
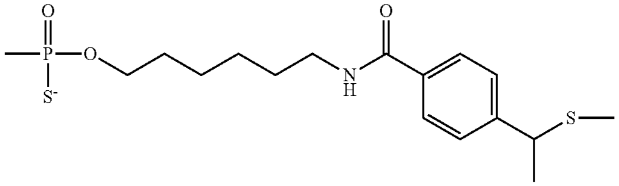
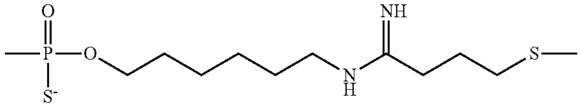
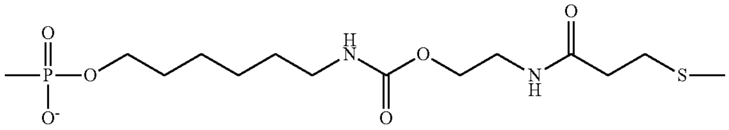
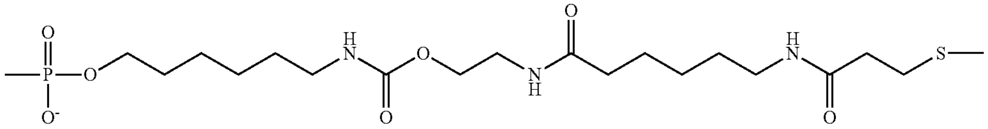
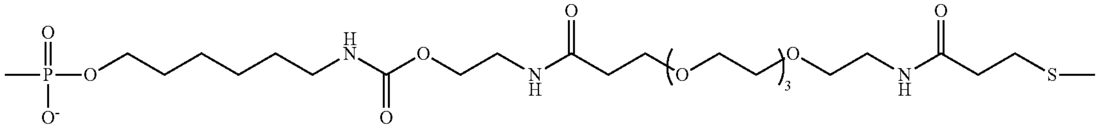
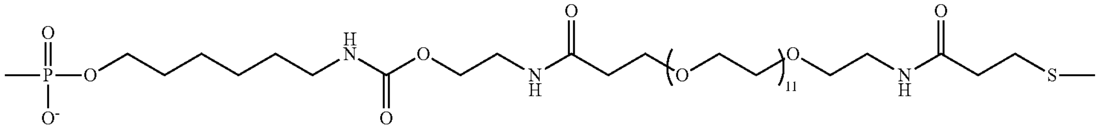
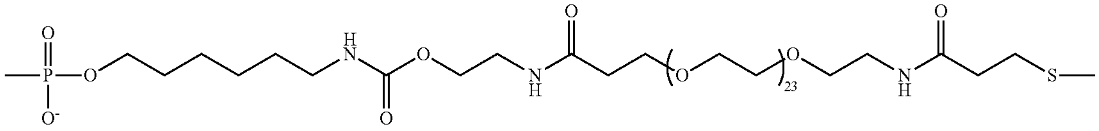
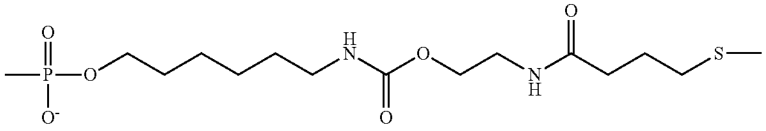

-continued
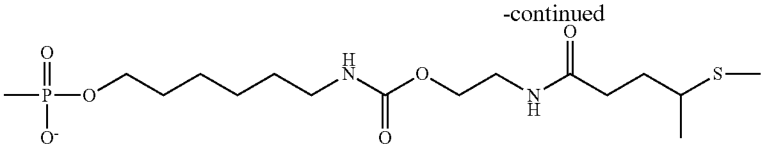
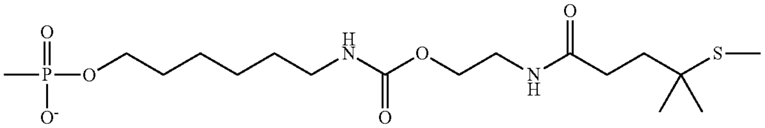
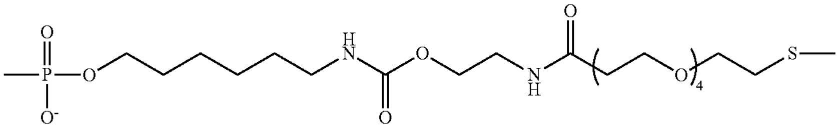
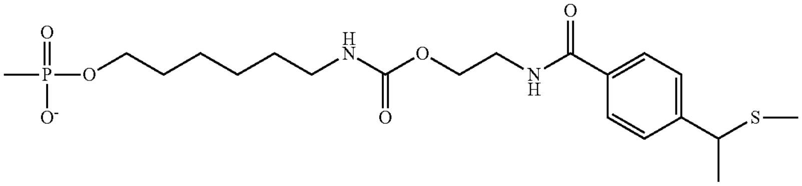
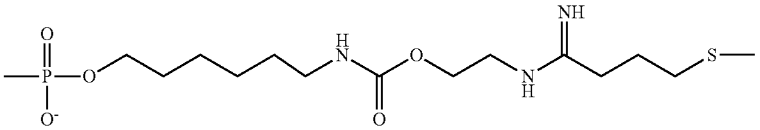
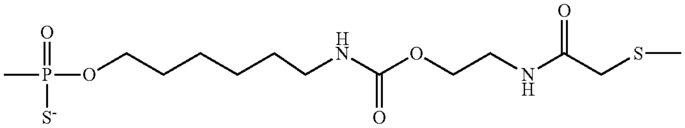
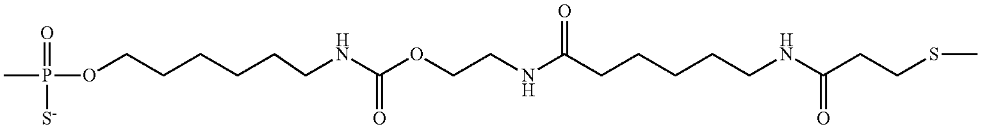
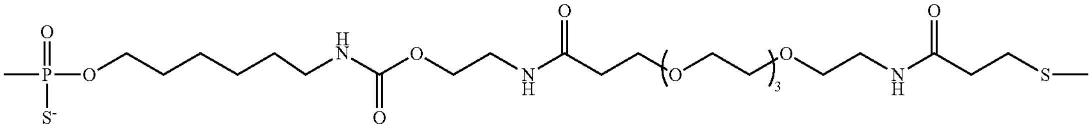
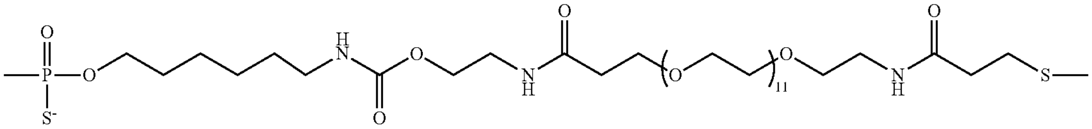
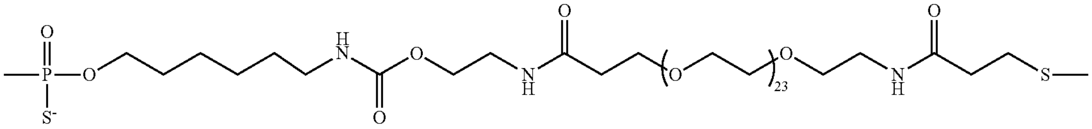
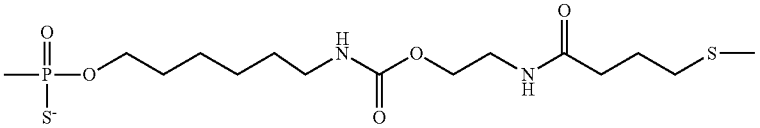
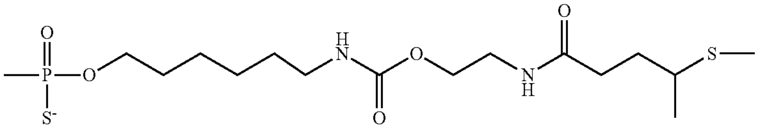
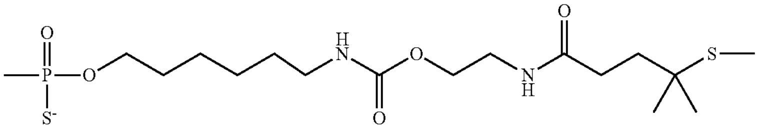

-continued
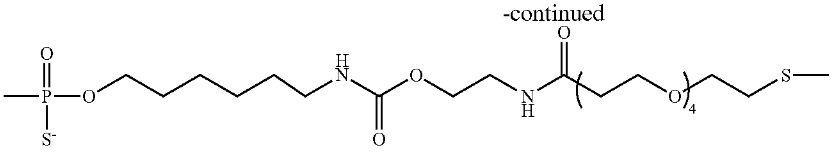
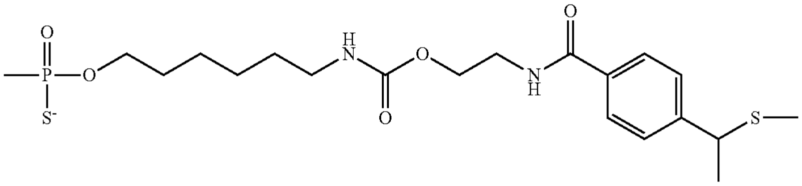
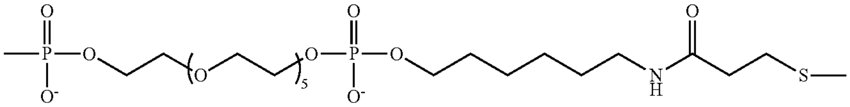
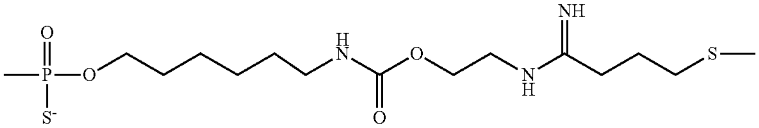
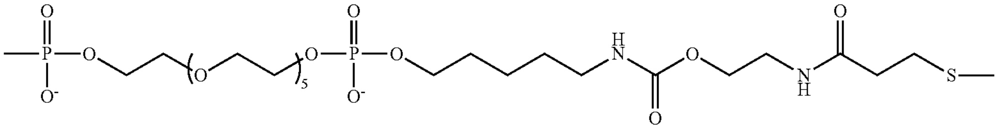
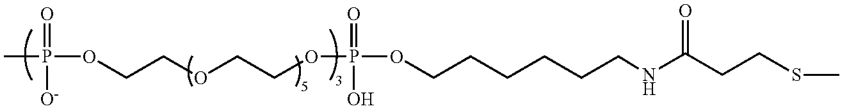
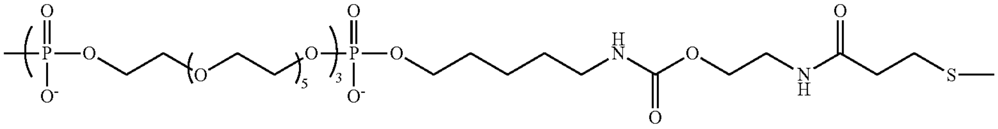
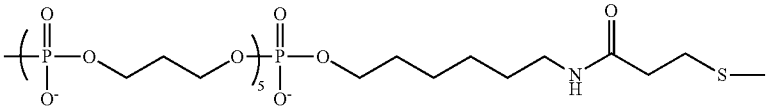
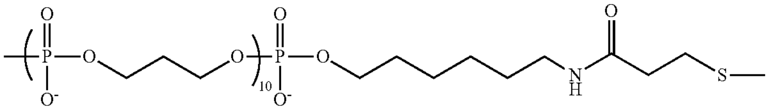
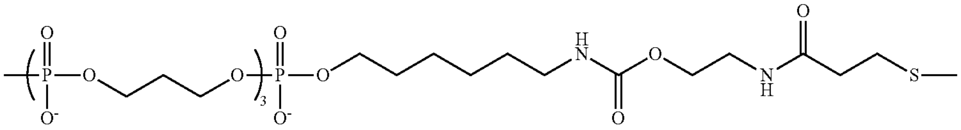
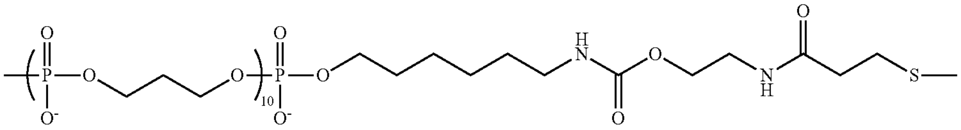
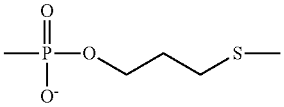
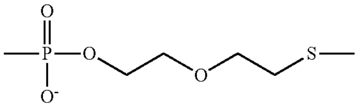
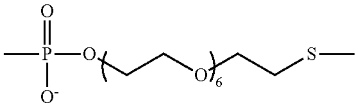

-continued
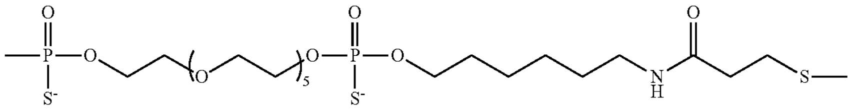
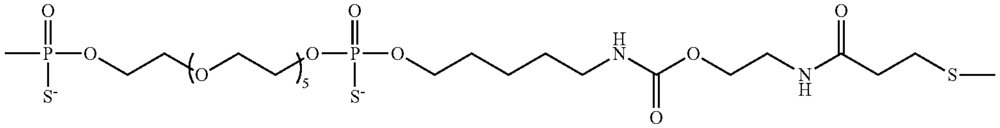
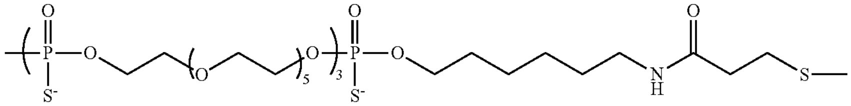
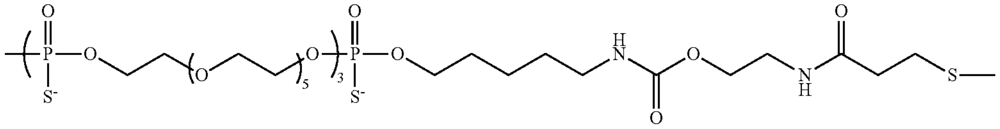
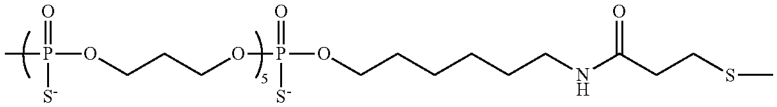
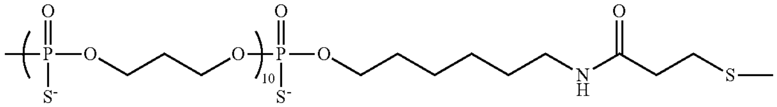
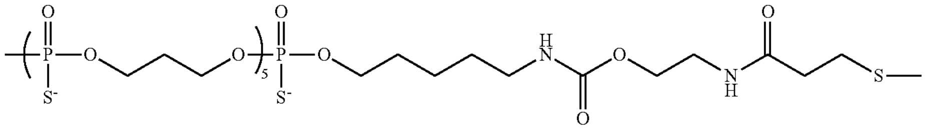
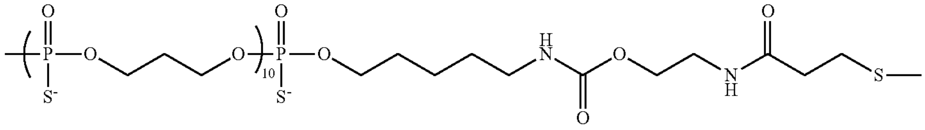
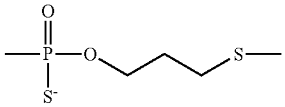
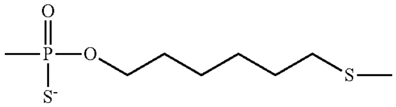
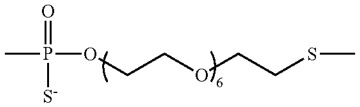
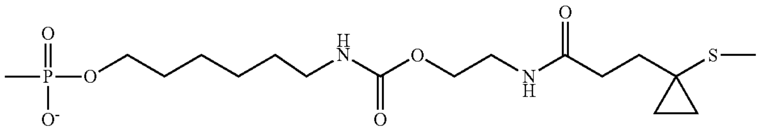
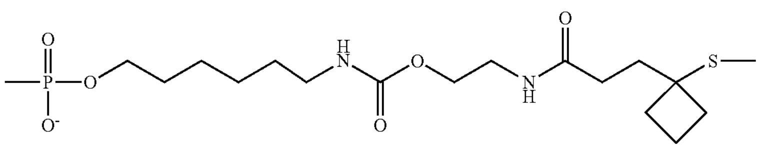
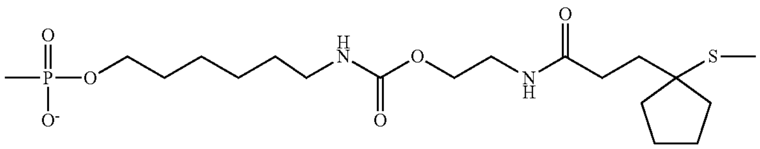

-continued
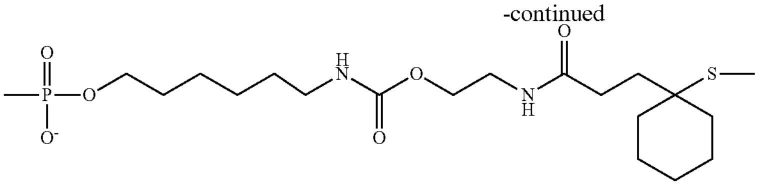
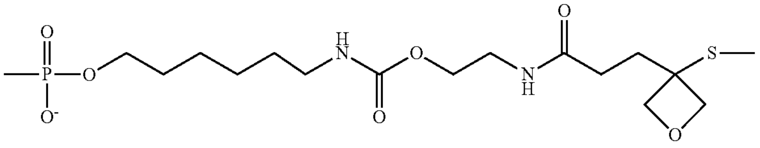
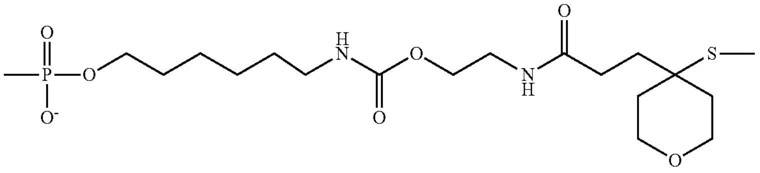
Preferred examples of the spacer include those having any of the structures shown below.
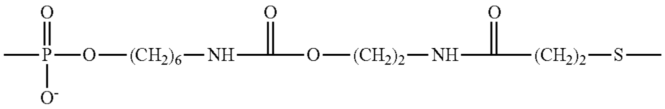
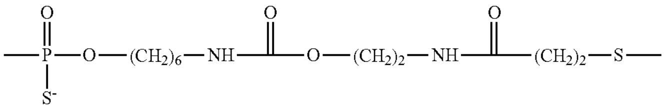
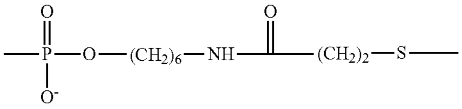
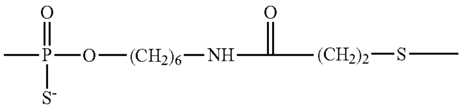
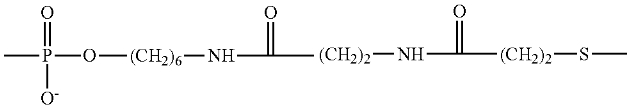
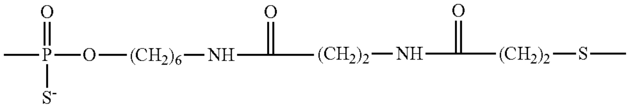
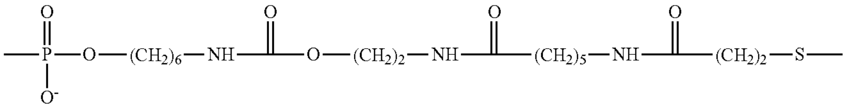
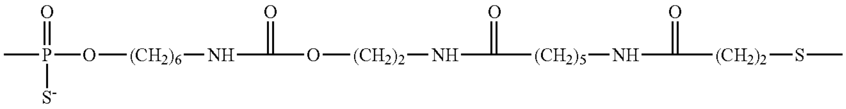

In another embodiment, more preferred examples of the spacer include those having any of the structures shown below.

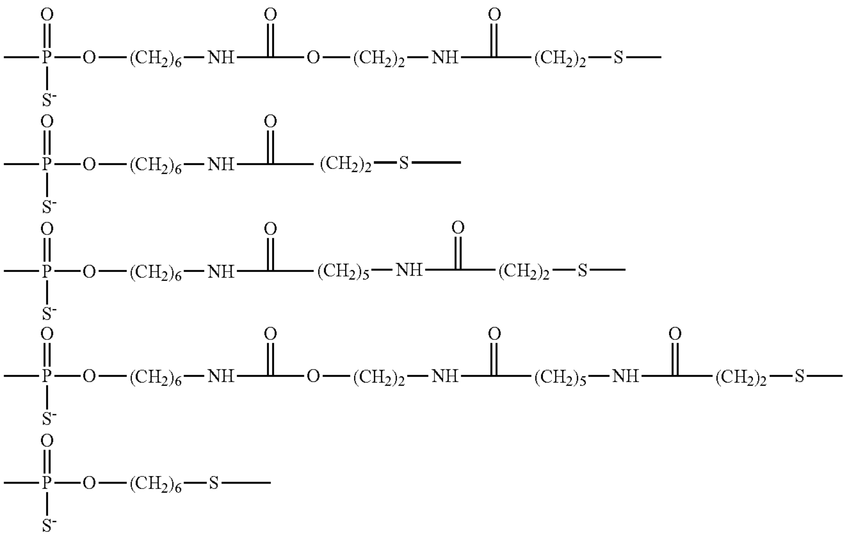

Examples of a combination of reactive functional groups used to form bonding between a spacer and a polynucleotide or polynucleotide derivative, and bonding between a spacer and a peptide include not only a combination of reactive functional groups used to form ester bonds, amide bonds, phosphoester bonds or the like, but also a combination of reactive functional groups used to immobilize a biomolecule on a biochip surface, for example. More specific examples thereof are detailed below.

(a) Alkyne and an Azide

Alkyne and an azide form a 1,2,3-triazole ring through a cycloaddition reaction (Huisgen reaction) as illustrated below. These compounds, which are stable functional groups capable of being introduced into many organic compounds including biomolecules, react with each other rapidly and nearly quantitatively even in a solvent including water, and generate no unnecessary wastes with little side effects; thus, they are widely used predominantly in so-called "click chemistry" reactions in the field of biochemistry. An alkyne derivative and an azido group can be introduced into an antigenic peptide or a polynucleotide or polynucleotide derivative using any known method. As for the alkyne derivative, those derivatives having a reactive functional group are easily available, such as propargyl alcohols or propargyl amines. By being reacted directly with a reactive functional group such as carboxyl group or hydroxyl group, or reacted with carbonyldiimidazole or the like, such an alkyne derivative can be introduced into an antigenic peptide or a polynucleotide or polynucleotide derivative, through amide bonding, ester bonding, urethane bonding, or other bonding formed by the reaction. The azido group can also be introduced into an antigenic peptide or a polynucleotide or polynucleotide derivative using any known method. Additionally, the Huisgen reaction is performed in the presence of a copper catalyst. However, since antigenic peptides, and polynucleotide derivatives in which the phosphodiester bonds are substituted with sulfur-containing functional groups such as phosphorothioate bonds, contain sulfur atoms coordinating to a copper ion, there may occur a deterioration of the catalytic activity of copper. Thus, it is preferred to add an excess amount of copper for the purpose of increasing the rate of reaction.

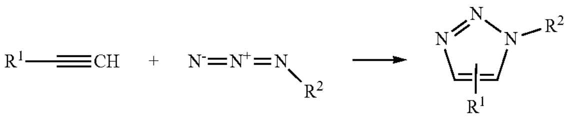

(b) Maleimide or Vinyl Sulfone and Thiol Group

Maleimide or vinyl sulfone, which has double bonds adjacent to an electron-withdrawing carbonyl or sulfone group, produces a stable thioether derivative at a near-neutral pH through an addition reaction (Michael addition reaction) with a thiol group as illustrated below. Since maleimide and vinyl sulfone derivatives containing a suitable spacer are commercially available, it is easy to introduce such a functional group into an antigenic peptide or a polynucleotide or polynucleotide derivative. In the case of introduction of a thiol group into an antigenic peptide, when the antigenic peptide contains cysteine, a thiol group at the side chain of the cysteine residue can be utilized. However, since cysteine is an amino acid with low abundance ratio, a peptide modified by introducing cysteine toward the N-terminus of an antigenic peptide is used. As the polynucleotide or polynucleotide derivative containing a thiol group, a thiolated polynucleotide in which the hydroxyl group at the 5' end is converted to a thiol group is used.

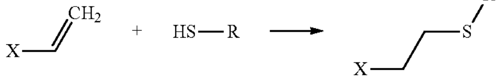

(X: COR' or $SO_2R'$)

(c) Thiol Group of a Peptide and Thiol Group of a Thiolated Polynucleotide

As mentioned above, a thiol group introduced onto the N-terminus of a peptide is reacted with a thiol group of a thiolated polynucleotide to form a disulfide group. Since the disulfide bond is cleaved in the presence of a reducing agent, this bond is inferior in stability over those mentioned in the previous sections, but is advantageous in that it is cleaved in reductive environment in vivo. The introduction of a thiol group onto a polynucleotide or polynucleotide derivative can be performed using any known method. One specific example of such a method is a reaction of an aminated polynucleotide or polynucleotide derivative with a N-succinimidyl ester of ω-(2-pyridyldithio)fatty acid as illustrated below.

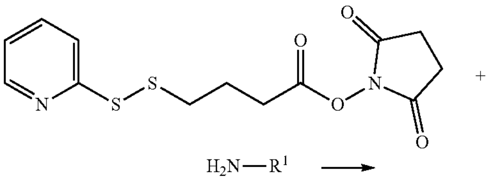

bond or bonds cleavable in biological environment. Therefore, among the combinations mentioned above in (a) to (c), a disulfide bond formed by a combination of a thiol group of a peptide and a thiol group of a thiolated polynucleotide is preferred since this bond is easily cleavable in vivo. In this case, the disulfide bond is a covalent bond between the spacer and the peptide.

Specific examples of a polynucleotide-peptide conjugate contained in the immunity-inducing agent of the present invention include CpG30(S)a-mTRP2pep9 (Compound 1), CpG20(S)a-mTRP2pep9 (Compound 2), and CpG30(S)a-hGP100pep9 (Compound 3) as mentioned below in Example 1, and the compounds listed in the subsequent paragraph. In the formulas shown below, the moieties represented by nucleotide sequences refer to DNA derivatives in which phosphodiester bonds are substituted with phosphorothioate bonds.

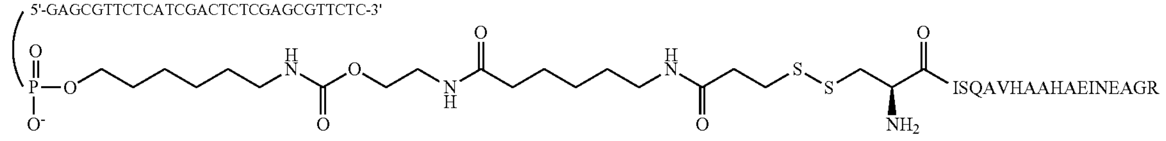

CpG30a-SS-C-OVA2-17

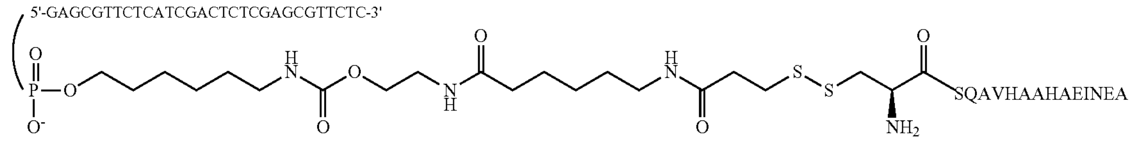

CpG30a-SS-C-OVA2-14

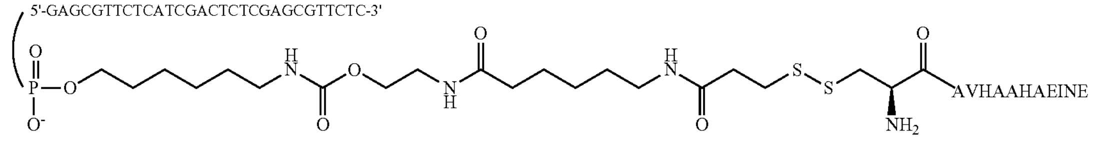

CpG30a-SS-C-OVA2-11

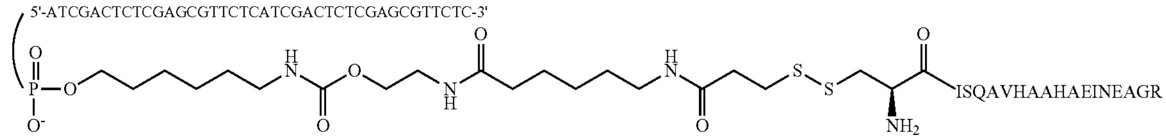

CpG40a-SS-C-OVA2-17

-continued

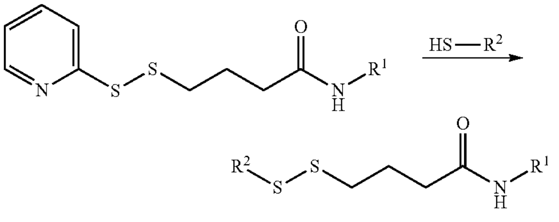

It is preferred that one or both of the covalent bond between the spacer and the polynucleotide or polynucleotide derivative, and the covalent bond between the spacer and the peptide should be a covalent bond or bonds cleavable in biological environment, and that at least a covalent bond between the spacer and the peptide should be a covalent Other specific examples of a polynucleotide-peptide conjugate contained in the immunity-inducing agent of the present invention include ISS1018-mTRP2pep9, ODN2006-mTRP2pep9, and ODN1826-mTRP2pep9 as mentioned below in Example 5, CpG30(S)a2-OVApep8 and CpG30(S)a2-mTRP2pep9 as mentioned below in Example 6, and CpG30(S)a2-OVA2-15 as mentioned below in Example 9.

In one embodiment, one polynucleotide or polynucleotide derivative contained in the immunity-inducing agent of the present invention may be bonded to two or more peptides. In other words, the immunity-inducing agent of this invention can comprise one polynucleotide or polynucleotide derivative and two or more peptides.

It is only necessary that one polynucleotide or polynucleotide derivative and two or more peptides are bonded via spacers. For example, the polynucleotide or polynucleotide derivative can be bonded to two or more peptides via different spacers. The polynucleotide or polynucleotide derivative may be bonded to two or more peptides via one branched spacer. By using a combination of any of the bonding modes mentioned above, one polynucleotide or polynucleotide derivative may be bonded to three or more peptides. The location at which the polynucleotide or polynucleotide derivative moiety is bonded to a spacer is not particularly limited, and can be selected, for example, from the 5' end and the 3' end.

Two or more peptides may be the same or different, but are preferably all the same. The number of peptides bonded to one polynucleotide or polynucleotide derivative is not particularly limited, and can be, for example, 2, 3, 4, 5, or more.

In one embodiment, the polynucleotide or polynucleotide derivative moiety of the immunity-inducing agent of the present invention may form a double strand with a polynucleotide or polynucleotide derivative having a nucleotide sequence complementary to the nucleotide sequence contained in said polynucleotide or polynucleotide derivative moiety (hereinafter also referred to as "complementary strand polynucleotide or polynucleotide derivative").

The complementary strand polynucleotide or polynucleotide derivative can be synthesized by the same synthesis method as that for the polynucleotide or polynucleotide derivative moiety of the immunity-inducing agent of the present invention. The complementary strand polynucleotide or polynucleotide derivative may be modified for the purpose of improving characteristic properties such as in vivo stability, toxicity, and in vivo kinetics. Examples of such a modification include lipid modification (vid., WO 2017/057540). A compound having lipid modification at one or both of its 5' and 3' ends can be synthesized by the method described in Example 8.

Formation of a double strand between the polynucleotide or polynucleotide derivative moiety of the immunity-inducing agent of the present invention and the complementary strand polynucleotide or polynucleotide derivative can be carried out by following a common annealing method. For example, the polynucleotide-peptide conjugate and the complementary strand polynucleotide or polynucleotide derivative are mixed, heated to become single stranded, and then naturally cooled to room temperature, whereby a double strand can be formed.

Examples of a pharmaceutically acceptable salt of the polynucleotide-peptide conjugate used as an active component of the immunity-inducing agent of the present invention include salts of alkali metals (e.g., potassium, sodium, lithium), salts of alkali earth metals (e.g., calcium, magnesium), ammonium salts (including tetramethylammonium salt, tetrabutylammonium salt), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine), acid adduct salts (including inorganic acid salts such as hydrochloride, hydrobromate, hydroiodide, hydrosulfate, phosphate and nitrate; and organic acid salts such as acetate, trifluoroacetate, lactate, tartrate, oxalate, fumarate, maleate, benzoate, citrate, methanesulfonate (mesylate), ethanesulfonate, benzenesulfonate, toluenesulfonate, isethionate, glucuronate, and gluconate), and the like.

The polynucleotide-peptide conjugate or a pharmaceutically acceptable salt thereof used as an active component of the immunity-inducing agent of the present invention can also be present as a solvate (including hydrate). The type of a solvate is not particularly limited as long as it is pharmaceutically acceptable, and examples thereof include hydrate and ethanol solvate.

The immunity-inducing agent of the present invention may further comprise a substance having immunostimulatory activity as an adjuvant. The adjuvant is, but not limited to, a substance that activates innate immunity. The adjuvant is preferably an agonist of an innate immunity receptor. Examples of innate immunity receptor agonists include TLR agonists (e.g., TLR2 agonist, TLR3 agonist, TLR4 agonist, TLR7 agonist, TLR8 agonist, TLR9 agonist), RLR (retinoic acid-inducible gene I (RIG-1)-like receptor) agonists, STING (stimulator of Interferon genes) agonists, NLR (nucleotide-binding oligomerization domain (NOD)-like receptor) agonists, and CLR (C-type lectin receptor) agonists. Examples of TLR agonists include lipopeptide, Poly IC RNA, imiquimod, resiquimod, monophosphoryl lipid (MPL), CpG-ODN, and the like. Examples of RLR agonists include pppRNA, Poly IC RNA, and the like. Examples of STING agonists include cGAMP, c-di-AMP, c-di-GMP, and the like. Examples of NLR agonists include iE-DAP, FK565, MDP, murabutide, and the like. Examples of CLR agonists include β-glucan, trehalose-6,6'-dimycolate, and the like. The adjuvant is preferably a TLR agonist, more preferably TLR4 agonist, TLR7 agonist or TLR9 agonist, still more preferably imiquimod, resiquimod, MPL or CpG-ODN. In some embodiments, the adjuvant is imiquimod, MPL or CpG-ODN. The adjuvant can be selected as appropriate depending on the type of a peptide or the like introduced into the polynucleotide-peptide conjugate. For example, the adjuvant can be CpG DNA or the like, or can be a polynucleotide/β-1,3-glucan complex, as disclosed in International Patent Publication No. WO 2015/118789.

The immunity-inducing agent of the present invention can be produced by a method comprising:

(1) preparing a single-chain polynucleotide or polynucleotide derivative comprising a CpG motif;
(2) preparing a peptide modified by substituting one or more contiguous amino acids at the N-terminus of an MHC-binding peptide with an amino acid having a reactive functional group which allows for the formation of a covalent bond with a spacer, wherein the one or more contiguous amino acids contain no anchor residues; and
(3) coupling the polynucleotide or polynucleotide derivative prepared in (1) and the peptide prepared in (2) via a spacer, wherein the spacer is covalently bonded at one end thereof to the polynucleotide or polynucleotide derivative and covalently bonded at the other end thereof to the peptide.

Therefore, in one embodiment, this invention provides a method for producing the immunity-inducing agent of this invention, the method comprising the aforementioned steps (1) to (3). The terms used in this embodiment shall be interpreted based on the descriptions of said terms provided herein. According to the method of this invention, immunity-inducing agents capable of inducing CTL activity can be produced using a wide variety of antigenic peptides.

Further, the present invention provides a polynucleotide-peptide conjugate or a pharmaceutically acceptable salt thereof. The terms used in this embodiment shall be interpreted based on the descriptions of said terms provided herein. The polynucleotide-peptide conjugate or the pharmaceutically acceptable salt thereof can be used as an active component of the immunity-inducing agent of this invention.

The polynucleotide-peptide conjugate or the pharmaceutically acceptable salt thereof can be produced by a method comprising the steps (1) to (3) which are the same as those of the aforementioned method for producing the immunity-inducing agent of this invention. Therefore, in one embodiment, this invention provides a method for producing a polynucleotide-peptide conjugate or a pharmaceutically acceptable salt thereof, the method comprising the aforementioned steps (1) to (3). The terms used in this embodiment shall be interpreted based on the descriptions of said terms provided herein. According to the aforementioned method, polynucleotide-peptide conjugates or pharmaceutically acceptable salts thereof, which can serve as an active component of immunity-inducing agents capable of inducing CTL activity, can be produced using a wide variety of antigenic peptides.

Further, the present invention provides a pharmaceutical composition comprising the immunity-inducing agent of this invention (hereinafter also referred to as "the pharmaceutical composition of the present [this] invention"). In order to produce the pharmaceutical composition of this invention, the polynucleotide-peptide conjugate or the pharmaceutically acceptable salt thereof as an active component can be mixed with any known components (any carriers, excipients and additives acceptable for pharmaceutical purposes) using any known pharmaceutical formulation method. Examples of pharmaceutical substances include, but are not limited to, the following: amino acids such as glycine, alanine, glutamine, asparagine, arginine or lysine; antioxidants such as ascorbic acid, sodium sulfate or sodium hydrogen sulfite; buffers such as phosphate buffer, citrate buffer, borate buffer, sodium hydrogen carbonate, or Tris-hydrochloride (Tris-HCl) solution; fillers such as mannitol or glycine; chelators such as ethylenediaminetetraacetic acid (EDTA); complexing agents such as caffeine, polyvinylpyrrolidine, β-cyclodextrin or hydroxypropyl-β-cyclodextrin; bulking agents such as glucose, mannose or dextrin; other carbohydrates such as monosaccharides or disaccharides; colorants; flavorants; diluents; emulsifiers; hydrophilic polymers such as polyvinylpyrrolidine; low-molecular-weight polypeptides; salt-forming counterions; preservatives such as benzalkonium chloride, benzoic acid, salicylic acid, thimerosal, phenethyl alcohol, methylparaben, propylparaben, chlorhexidine, sorbic acid or hydrogen peroxide; solvents such as glycerol, propylene glycol or polyethylene glycol; sugar alcohols such as mannitol or sorbitol; suspending agents; surfactants such as sorbitan esters, polysorbates (e.g., polysorbate 20, polysorbate 80), triton, tromethamine, lecithin or cholesterol; stability enhancers such as sucrose or sorbitol; elasticity enhancers such as sodium chloride, potassium chloride, mannitol or sorbitol; transporting agents; excipients; and/or pharmaceutical aids. Any skilled artisan can determine, as appropriate, the preferred composition profile of the pharmaceutical composition depending on the disease to be treated, the administration route to be applied, and the like.

The pharmaceutical composition of the present invention is provided in a dosage form suitable for oral or parenteral administration. For example, the pharmaceutical composition is used as an injection, a suppository or the like. Examples of injections include various injection forms such as intravenous injection, subcutaneous injection, intradermal injection, intramuscular injection and drip infusion. Such injections can be prepared according to known methods. With regard to a method for preparing an injection, the injection can be prepared by, for example, dissolving or suspending the immunity-inducing agent of this invention in a sterile aqueous solvent commonly used for injection. Examples of the aqueous solvent for injection that can be used include distilled water, physiological saline, a buffer such as phosphate buffer, carbonate buffer, Tris buffer or acetate buffer, or the like. The pH of such an aqueous solvent is in the range of from 5 to 10, preferably from 6 to 8. The prepared injection is preferably filled in an appropriate ampule. The injection may be made into a freeze-dried formulation. As for other dosage forms besides injections, the pharmaceutical composition can be provided in a dosage form for transdermal or transmucosal absorption (e.g., liquid spray, ointment, gel, lotion, patch), in a subcutaneous, local, sustained-release dosage form (e.g., suspension containing a nanogel, a biodegradable micro/nano-capsule, etc., or temperature-responsive gel), or in the form of a pharmaceutical preparation accompanied by a percutaneous device for skin permeation (e.g., iontophoresis, microneedle), a powder, a tablet, a capsule, a syrup, an inhalant such as aerosol or dry powder, or the like.

The pharmaceutical composition of the present invention can be administered to a human or a warm-blooded animal (e.g., mouse, rat, rabbit, sheep, pig, cow, horse, chicken, cat, dog, monkey) by any of oral and parenteral routes. Examples of parenteral routes include subcutaneous, intracutaneous and intramuscular injections, intraperitoneal administration, drip infusion, intravenous administration, administration to oral mucosa, spray into nasal mucosa or pharyngeal region, and the like.

The dose of the polynucleotide-peptide conjugate serving as an active component of the pharmaceutical composition of the present invention differs according to activity, the disease to be treated, the type, body weight, sex and age of an animal to be medicated, the type of disease, administration method, and/or the like. As an example, in the case of medication of an adult human with a body weight of 60 kg, the daily dose for oral administration is generally in the range of from about 0.1 to about 100 mg, preferably from about 1.0 to about 50 mg, more preferably from about 1.0 to about 20 mg, and the daily dose for parenteral administration is generally in the range of from about 0.01 to about 30 mg, preferably from about 0.1 to about 20 mg, more preferably from about 0.1 to about 10 mg. When the pharmaceutical composition is administered to other animals, the dose to be used for such animals is calculated by converting the aforementioned dose into a dose per unit body weight and multiplying the dose per unit body weight by the body weight of an animal to be medicated.

The frequency of administering the pharmaceutical composition of the present invention to a subject can be easily determined by any skilled artisan in consideration of the type, body weight, sex and age of an animal to be medicated, the type of disease, administration method, and/or the like. For example, in the case of administering the composition of this invention as a vaccine, the composition can be generally administered one to several times per day for only one day, or several times at intervals of one to several weeks in the same manner as common vaccine preparations. The administration is preferably performed while observing developments—for example, additional immunization can be performed at intervals of at least about one week. It is expected that additional immunization can yield a booster effect and provide more effective protection against infections.

By administering the pharmaceutical composition of the present invention to a patient with a pathogenic infection or a cancer, or a subject predisposed to suffering from a cancer or a pathogenic infection, cytotoxic T lymphocytes (CTLs) or helper T cells present in the medicated patient or subject are activated in an antigen-specific manner to induce a protective immune response of a warm-blooded animal (preferably a human), thereby enabling prevention or treatment of the infection or cancer. Also, by administering the pharmaceutical composition of this invention to a patient with an allergic disease, the pharmaceutical composition can be used as an antigen-specific immunotherapy which inhibits excessive immune responses to allergens causative of allergic diseases. In other words, the pharmaceutical composition of this invention is useful as a vaccine for the prevention or treatment of diseases such as infections, cancers and allergic diseases as mentioned above. In this invention, the terms “tumor(s)” and “cancer(s)” are exchangeably used. Also, in this invention, tumors, malignant tumors, cancers, malignant neoplasms, carcinomas, sarcomas and the like may be collectively referred to as “tumors” or “cancers”. Further, the terms “tumor(s)” and “cancer(s)” may in some cases include pathological conditions classified as pre-cancer stages, such as myelodysplastic syndromes.

The types of tumors to be treated or prevented are not particularly limited as long as they are tumors proved to be susceptible to the pharmaceutical composition of the present invention. Examples of tumors to be treated include breast cancer, colon cancer, prostate cancer, lung cancer (including small-cell lung cancer, non-small-cell lung cancer, etc.), stomach cancer, ovarian cancer, cervical cancer, endometrial cancer, corpus uteri cancer, kidney cancer, hepatocellular cancer, thyroid cancer, esophageal cancer, osteosarcoma, skin cancer (including melanoma, etc.), glioblastoma, neuroblastoma, ovarian cancer, head and neck cancer, testicular tumor, bowel cancer, blood cancer (including leukemia, malignant lymphoma, multiple myeloma, etc.), retinoblastoma, pancreatic cancer, and the like.

The pharmaceutical composition of the present invention may be used in combination with other antitumor agents. Examples of other antitumor agents include antitumor antibiotics, antitumor plant components, BRMs (biological response modifiers), hormones, vitamins, antitumor antibodies, molecular targeted drugs, alkylating agents, metabolic antagonists, and the like.

More specifically, examples of antitumor antibiotics include mitomycin C, bleomycin, peplomycin, daunorubicin, aclarbicin, doxorubicin, idarubicin, pirarubicin, THP-adriamycin, 4'-epi-doxorubicin or epirubicin, chromomycin A3, actinomycin D, or the like.

Examples of antitumor plant components and derivatives thereof include vinca alkaloids such as vindesine, vincristine or vinblastine; taxanes such as paclitaxel, docetaxel or cabazitaxel; or epipodophyllotoxins such as etoposide or teniposide.

Examples of BRMs include tumor necrosis factors, indomethacin, or the like.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, mepitiostane, medroxyprogesterone, or the like.

Examples of vitamins include vitamin C, vitamin A, or the like.

Antitumor antibodies or molecular targeted drugs include trastuzumab, rituximab, cetuximab, panitumumab, nimotuzumab, denosumab, bevacizumab, infliximab, ipilimumab, nivolumab, pembrolizumab, avelumab, pidilizumab, atezolizumab, ramucirumab, imatinib mesylate, dasatinib, sunitinib, lapatinib, dabrafenib, trametinib, cobimetinib, pazopanib, palbociclib, panobinostat, sorafenib, crizotinib, vemurafenib, kizaruchinib, bortezomib, carfilzomib, ixazomib, midostaurin, gilteritinib, or the like.

Examples of alkylating agents include alkylating agents such as nitrogen mustard, nitrogen mustard N-oxide, bendamustine or chlorambucil; aziridine-based alkylating agents such as carboquone or thiotepa; epoxide-based alkylating agents such as dibromomannitol or dibromodulcitol; nitrosourea-based alkylating agents such as carmustine, lomustine, semustine, nimustine hydrochloride, streptozocin, chlorozotocin or ranimustine; busulfan, improsulfan tosilate, temozolomide, dacarbazine, or the like.

Examples of metabolic antagonists include purine metabolic antagonists such as 6-mercaptopurine, 6-thioguanine or thioinosine; pyrimidine metabolic antagonists such as fluorouracil, tegafur, tegafur-uracil, carmofur, doxifluridine, broxuridine, cytarabine or enocitabine; folate metabolic antagonists such as methotrexate or trimetrexate, or the like.

Other antitumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, schizophyllan, picibanil, procarbazine, pipobroman, neocarzinostatin, hydroxyurea, ubenimex, thalidomide, lenalidomide, pomalidomide, eribulin, tretinoin, krestin, or the like.

Examples of infections to be treated or prevented include infections with pathogens such as viruses, fungi or bacteria. Examples of viruses include influenza virus, hepatitis virus, human immunodeficiency virus (HIV), RS virus, rubella virus, measles virus, epidemic parotitis virus, herpesvirus, poliovirus, rotavirus, Japanese encephalitis virus, varicella virus, adenovirus, rabies virus, yellow fever virus, or the like. Examples of bacteria include *Corynebacterium diphtheriae, Clostridium tetani, Bordetella pertussis, Hemophilus influenza, Mycobacterium tuberculosis, Streptococcus pneumoniae, Helicobacter pylori, Bacillus anthracis, Salmonella typhosa, Neisseria meningitidis, Bacillus dysenteriae, Vibrio cholerae*, or the like. Examples of fungi include fungi of the genus *Candida*, fungi of the genus *Histoplasma*, fungi of the genus *Cryptococcus*, fungi of the genus *Aspergillus*, or the like. The pharmaceutical composition of the present invention may be used in combination with existing therapeutic agents for such infections.

Examples of allergic diseases to be treated or prevented include bronchial asthma, allergic rhinitis, atopic dermatitis, hives, food allergies, animal allergies, anaphylaxis, or the like.

Administration of the pharmaceutical composition of the present invention in combination with an adjuvant or other drugs means ingestion of both of the drugs into the body of a medicated subject within a certain period of time. A single preparation incorporating both of the drugs may be administered, or both of the drugs may be formulated into separate preparations and administered separately. When both of the drugs are formulated into separate preparations, the timings of administration of the separate preparations are not particularly limited, and they may be administered simultaneously or may be sequentially administered at intervals of times or days. When separate preparations are administered at different times or on different days, the order of their administration is not particularly limited. Since separate preparations are generally administered according to their respective administration methods, the numbers of doses of these preparations may be the same or different. Also, when both of the drugs are formulated into separate preparations, the separate preparations may be administered by the same administration method (via the same administration route) or by different administration methods (via different administration routes). Further, both of the drugs are not necessarily present simultaneously in the body, and it is only necessary that both of the drugs should be ingested into the body within a certain period of time (e.g., for one month, preferably for one week, more preferably for a few days, still more preferably for one day). The active component of one preparation may be eliminated from the body at the time of administration of the other preparation.

In one embodiment, the present invention provides a method for the treatment or prevention of a disease, the method comprising administering a therapeutically or prophylactically effective amount of the pharmaceutical composition of this invention to a subject in need thereof. Examples of diseases include pathogenic infections, tumors, and allergic diseases, and preferred examples thereof include tumors.

As referred to in the present invention, the term "therapeutically or prophylactically effective amount" means an amount required for the pharmaceutical composition to exhibit a therapeutic or prophylactic effect in consideration of particular disease or symptom, dosage form, and administration route, and is determined, as appropriate, depending on the species of a subject, type of disease or symptom, indication, sex, age, pre-existing condition, and other factors.

The present invention further provides the following embodiments.

[B1] An immunity-inducing agent comprising a polynucleotide-peptide conjugate or a pharmaceutically acceptable salt thereof as an active component, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by deleting one or more contiguous amino acids at the N-terminus and/or the C-terminus of an MHC-2-binding peptide and adding an amino acid having a reactive functional group which allows for the formation of a covalent bond with the spacer, wherein the one or more contiguous amino acids contain no anchor residues for MHC-2 binding.

[B2] The immunity-inducing agent as set forth in [B1], wherein one or both of the covalent bond between the spacer and the polynucleotide or polynucleotide derivative, and the covalent bond between the spacer and the peptide are a covalent bond or bonds cleavable in biological environment.

[B3] The immunity-inducing agent as set forth in [B1] or [B2], wherein the amino acid having a reactive functional group which allows for the formation of a covalent bond with the spacer is cysteine or an analogue thereof having a thiol group.

[B4] The immunity-inducing agent as set forth in any one of [B1] to [B3], wherein the covalent bond between the spacer and the peptide is a disulfide bond.

[B5] The immunity-inducing agent as set forth in any one of [B1] to [B4], wherein the polynucleotide or polynucleotide derivative is a polydeoxyribonucleotide (DNA) or DNA derivative comprising two or more CpG motifs.

[B6] The immunity-inducing agent as set forth in any one of [B1] to [B5], wherein the polynucleotide or polynucleotide derivative has a nucleotide length of not less than 15 and not more than 40.

[B7] The immunity-inducing agent as set forth in [B6], wherein the polynucleotide or polynucleotide derivative has a nucleotide length of not less than 20 and not more than 30.

[B8] The immunity-inducing agent as set forth in any one of [B1] to [B7], wherein the polynucleotide or polynucleotide derivative is a polynucleotide derivative in which phosphodiester bonds are at least partially substituted with phosphorothioate bonds.

[B9] The immunity-inducing agent as set forth in [B8], wherein, in the polynucleotide derivative in which phosphodiester bonds are at least partially substituted with phosphorothioate bonds, not less than 50% of the phosphodiester bonds are substituted with phosphorothioate bonds.

[B10] The immunity-inducing agent as set forth in [B9], wherein, in the polynucleotide derivative in which phosphodiester bonds are at least partially substituted with phosphorothioate bonds, not less than 90% of the phosphodiester bonds are substituted with phosphorothioate bonds.

[B11] The immunity-inducing agent as set forth in any one of [B1] to [B10], wherein the spacer comprises repeating units represented by the following formula:

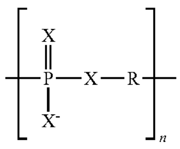

wherein

X represents an oxygen atom or a sulfur atom (wherein each X may be the same or different), R represents any of $(CH_2)_pO$, $(CH_2)_qNH$, and $(CH_2CH_2O)_m$ (wherein m, p and q each independently represent a natural number of not more than 10), and n represents a natural number of not more than 10.

[B12] The immunity-inducing agent as set forth in any one of [B1] to [B11], wherein the spacer has a structure represented by any of the following formulas.

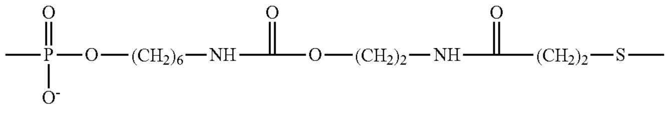

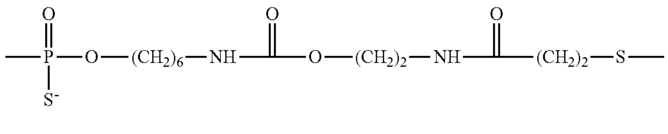

-continued

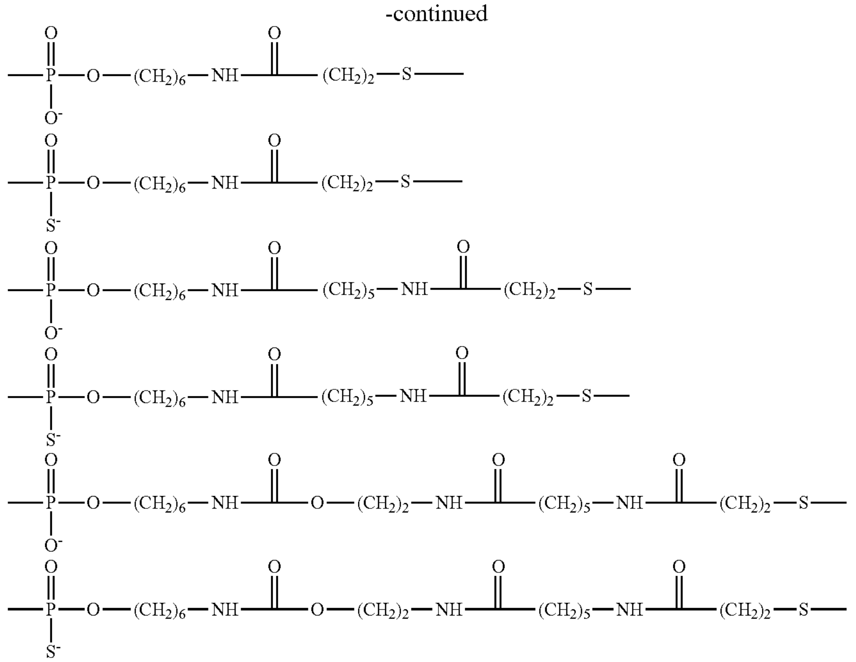

[B13] The immunity-inducing agent as set forth in any one of [B1] to [B10], wherein the spacer has a structure represented by any of the following formulas.

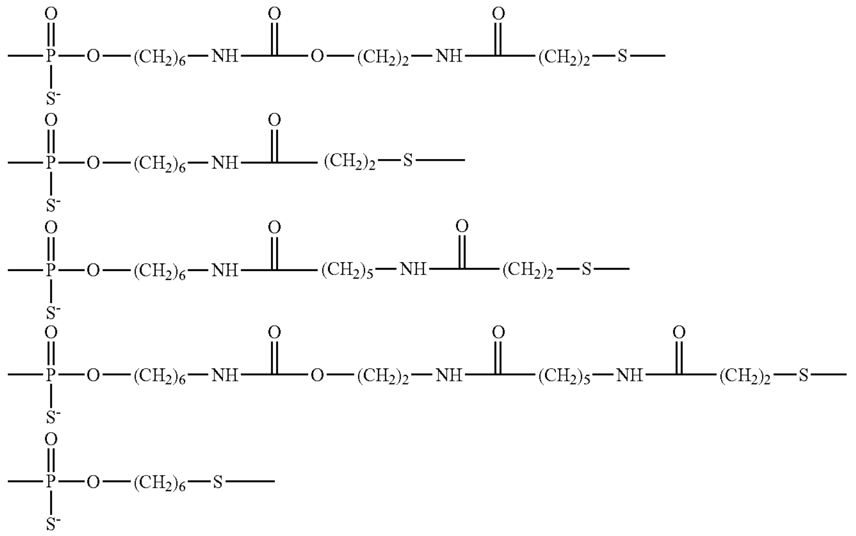

[B14] The immunity-inducing agent as set forth in any one of [B1] to [B13], further comprising a substance having immunostimulatory activity as an adjuvant.

[B15] A pharmaceutical composition comprising the immunity-inducing agent as set forth in any one of [B1] to [B14].

[B16] The pharmaceutical composition as set forth in [B15], or the treatment or prevention of infections, tumors, or allergic diseases.

[B17] A method for the treatment or prevention of infections, tumors, or allergic diseases, the method comprising administering the immunity-inducing agent as set forth in any one of [B1] to [B14] to a patient.

[B18] The immunity-inducing agent as set forth in any one of [B1] to [B14], for use in the treatment or prevention of infections, tumors, or allergic diseases.

[B19] Use of the immunity-inducing agent as set forth in any one of [B1] to [B14] for the manufacture of a pharmaceutical composition for the treatment or prevention of infections, tumors, or allergic diseases.

Hereunder, the invention of the embodiments [B1] to [B19] as mentioned above is referred to as "the present [this] invention B". The terms used in this invention B shall be interpreted based on the descriptions of said terms provided herein, as long as these descriptions are not contradictory in the invention using an MHC-2-binding peptide.

In the present invention B, the peptide contained in the polynucleotide-peptide conjugate is a peptide modified by deleting one or more contiguous amino acids at the N-terminus and/or the C-terminus of an MHC-2-binding peptide and adding an amino acid having a reactive functional group which allows for the formation of a covalent bond with the spacer. The number of amino acids deleted is not particularly limited as long as they contain no anchor residues for MHC-2 binding. The number of amino acids deleted can be determined, as appropriate, depending on the length of an original MHC-2-binding peptide and the locations of anchor residues. The amino acid having a reactive functional group which allows for the formation of a covalent bond with the spacer can be added to the N-terminus or the C-terminus.

In the present invention B, the amino acid length of the peptide contained in the polynucleotide-peptide conjugate is not particularly limited, and can be, for example, not less than 8 and not more than 30.

Specific examples of the immunity-inducing agent of the present invention B include CpG30(S)a2-OVA2-15 as mentioned below in Example 9.

According to the present invention B, polynucleotide-peptide conjugates can be prepared using shorter peptides, and therefore, pharmaceutical compositions that are superior in physical properties and/or economy can be provided.

EXAMPLES

Next, the following describes working examples conducted to confirm the actions and effects of the present invention. As referred to in the following examples, the term "CpG DNA(S)" refers to a DNA derivative (an example of polynucleotide derivative) which has a nucleotide sequence comprising a CpG motif and in which phosphodiester bonds are substituted with phosphorothioate bonds. In the following examples, the nucleotide sequences of polynucleotide derivatives are written in a single-letter notation with the 5' end to the left (and the 3' end to the right), and the amino acid sequences of peptides are written in a single-letter notation with the N-terminus to the left (and the C-terminus to the right). In the polynucleotide derivatives written in a single-letter notation, all phosphodiester bonds are substituted with phosphorothioate bonds, and their termini end with an oxygen atom at the 5'- or 3'-hydroxy group of the terminal nucleotide when coupled to a spacer, or end with the entire 5'- or 3'-hydroxy group (including a hydrogen atom) of the terminal nucleotide when not coupled to a spacer. Further, in the following examples, the CpG DNA(S)-peptide conjugate was prepared in the form of a salt having triethylamine and acetic acid added thereto.

Example 1: Preparation of CpG DNA(S)-Peptide Conjugates (1) Synthesis of CpG DNA(S) Derivatives Synthesis of CpG DNA(S) was performed using the phosphoramidite method (vid., e.g., *Nucleic Acids Research,* 12, 4539 (1984)). Synthesis of amino group-modified CpG DNA(S) was performed using an ssH amino linker (*Bioorg. Med. Chem.,* 16, 941-949 (2008)). These syntheses were contracted to a contract synthesis service (provided by GeneDesign Inc.).

The nucleotide sequences of the synthesized CpG DNA (S) are shown below.

CpG30a:
5'-GAGCGTTCTCATCGACTCTCGAGCGTTCTC-3' (K3-30(a) in Table 1; SEQ ID NO: 6)

CpG20a:
5'-ATCGACTCTCGAGCGTTCTC-3' (K3 in Table 1; SEQ ID NO: 1)

The obtained amino group-modified CpG DNA(S) derivatives have a structure represented by the formula shown below at the 5' end thereof. Hereinafter, among the CpG DNA(S) derivatives having a structure represented by the following formula at the 5' end thereof, the one having the sequence of SEQ ID NO: 6 is referred to as "CpG30(S)a", and the one having the sequence of SEQ ID NO: 1 is referred to as "CpG20(S)a.

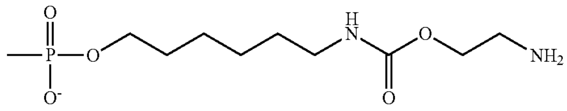 [SMILES: CP(=O)([O-])OCCCCCCNC(=O)OCCN]

Further, amino group-modified CpG DNA(S) and succinimidyl 6-[3'-(2-pyridyldithio)-propionamido]hexanoate (LC-SPDP) were mixed at a molar ratio of 1:30 in a phosphate buffer (pH 8.0). After being left to stand at 40° C. for 3 hours, the mixture was purified using a NAP-5 column to yield SPDP-modified CpG DNA(S).

Hereinafter, the structure represented by the following formula is referred to as "ssH amino linker".

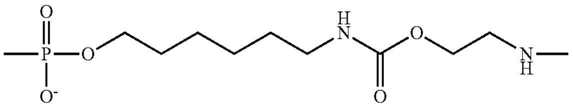

(2) Synthesis of N-Terminal Modified Peptides

Synthesis of peptides was contracted to a contract synthesis service (provided by GeneDesign Inc.).

The amino acid sequences of the synthesized peptides are shown below.

C-OVA8: (SEQ ID NO: 30)
CSIINFEKL

C-TRP2-9: (SEQ ID NO: 31)
CSVYDFFVWL

C-TRP2-8: (SEQ ID NO: 32)
CVYDFFVWL

C-gp100-9: (SEQ ID NO: 33)
CKVPRNQDWL

C-gp100-8: (SEQ ID NO: 34)
CVPRNQDWL

CM-TRP2-9: (SEQ ID NO: 35)
CMSVYDFFVWL

C-TRP2-13: (SEQ ID NO: 36)
CFANASVYDFFVWL

C-TRP2-11: (SEQ ID NO: 37)
CNASVYDFFVWL

C-OVA8 is a peptide modified by adding cysteine to the N-terminus of a peptide (hereinafter also referred to as "OVA peptide 1") consisting of amino acid residues 258 to 265 of ovalbumin (OVA; GenBank accession No. CAA23716.1).

C-TRP2-9 is a peptide modified by adding cysteine to the N-terminus of a peptide (hereinafter also referred to as "TRP2-9") consisting of amino acid residues 180 to 188 of mTRP2 (mouse tyrosinase-related protein 2; GenBank accession No. CAA44951.1) known as a melanoma-associated antigen.

C-TRP2-8 is a peptide modified by adding cysteine to the N-terminus of a peptide consisting of amino acid residues 181 to 188 of mTRP2.

C-gp100-9 is a peptide modified by adding cysteine to the N-terminus of a peptide (hereinafter also referred to as "hGP100-9") consisting of amino acid residues 25 to 33 of hGP100 (human glycoprotein 100; GenBank accession No. AAC60634.1) known as a melanoma-associated antigen.

C-gp100-8 is a peptide modified by adding cysteine to the N-terminus of a peptide consisting of amino acid residues 26 to 33 of hGP100.

CM-TRP2-9 is a peptide modified by adding cysteine and methionine to the N-terminus of a peptide consisting of amino acid residues 180 to 188 of mTRP2.

C-TRP2-13 is a peptide modified by adding cysteine to the N-terminus of a peptide consisting of amino acid residues 176 to 188 of mTRP2.

C-TRP2-11 is a peptide modified by adding cysteine to the N-terminus of a peptide consisting of amino acid residues 178 to 188 of mTRP2.

(3) Synthesis of CpG DNA(S)-Peptide Conjugates

One mol of each of the SPDP-modified CpG DNA(S) derivatives synthesized in (1) was mixed with 25 mol of each of the peptides synthesized in (2) in an aqueous solution of 30% N,N-dimethylformamide (DMF). After being left to stand at 40° C. for 3 hours, each of the mixtures was fractionated by HPLC under any of the conditions (A) to (C) as detailed below to afford CpG DNA(S)-peptide conjugates. The HPLC conditions and retention times used for the fractionation of the different conjugates are shown in Table 2.

<HPLC Condition (A)>

HPLC was performed under the following gradient conditions using 0.1 M hexafluoroisopropanol/8 mM triethylamine (TEA) as solvent A and methanol as solvent B, respectively, and the column X-Bridge C18 (2.5 μm, 4.6×75 mm; Waters Corporation), at a column temperature of 60° C. and a flow rate of 1 mL/min.

| | | |
|---|---|---|
| 0 min. | A: 95% | B: 5% |
| to 20 min. | A: 70% | B: 30% |

<HPLC Condition (B)>

HPLC was performed under the following gradient conditions using 0.1 M hexafluoroisopropanol/8 mM triethylamine (TEA) as solvent A and methanol as solvent B, respectively, and the column X-Bridge C18 (2.5 μm, 4.6×75 mm; Waters Corporation), at a column temperature of 60° C. and a flow rate of 1 mL/min.

| | | |
|---|---|---|
| 0 min. | A: 95% | B: 5% |
| to 25 min. | A: 60% | B: 40% |

<HPLC Condition (C)>

HPLC was performed under the following gradient conditions using 0.1 M triethylammonium acetate (TEAA; pH 7.0) as solvent A and acetonitrile as solvent B, respectively, and the column ZORBAX Eclipse Plus C18 (Agilent Technologies), at a column temperature of 40° C. and a flow rate of 1 mL/min.

| | | |
|---|---|---|
| 0 min. | A: 90% | B: 10% |
| to 25 min. | A: 70% | B: 30% |
| to 30 min. | A: 0% | B: 100% |

<HPLC Condition (D)>

HPLC was performed under the following gradient conditions using 0.1 M hexafluoroisopropanol/8 mM triethylamine (TEA) as solvent A and methanol as solvent B, respectively, and the column X-Bridge C18 (2.5 μm, 4.6×75 mm; Waters Corporation), at a column temperature of 60° C. and a flow rate of 1 mL/min.

| | | |
|---|---|---|
| 0 min. | A: 95% | B: 5% |
| to 25 min. | A: 50% | B: 50% |

During the process of the HPLC fractionation of the solutions obtained after the reactions of SPDP-modified CpG DNA(S) with the peptides, detection was performed by monitoring the absorption at 260 nm. It was observed that the elution times of the fractionated CpG DNA(S)-peptide conjugates were delayed as compared to that of SPDP-modified CpG DNA(S). This is considered to be because the elution times became longer since SPDP-modified CpG DNA(S) derivatives were bonded to the hydrophobic peptides. Further, in the chromatograms obtained from the fractionation, no peak for unreacted SPDP-modified CpG DNA(S) was observed, and only the peaks for the CpG DNA(S)-peptide conjugates were detected—this fact confirmed that the CpG DNA(S)-peptide conjugates of interest were obtained with high purity. As an example of the results of HPLC analysis, a chromatogram obtained by the HPLC analysis of CpG30(S)a-mTRP2pep9 (Compound 1) under the condition (B) is shown in FIG. 1.

The structures of the obtained CpG DNA(S)-peptide conjugates are shown below. In the following formula, "CpG DNA" represents a nucleotide sequence moiety of CpG30(S)a or CpG20(S)a, and "peptide" represents a moiety of each of the peptides synthesized above in (2) which excludes N-terminal cysteine.

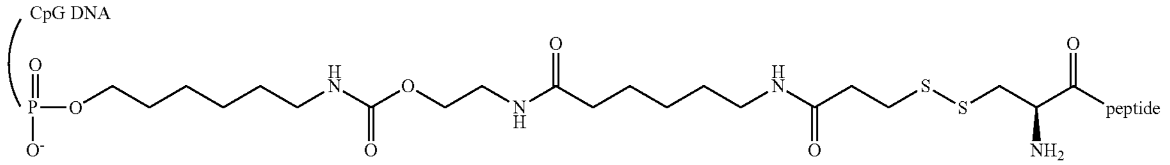

The synthesized CpG DNA(S)-peptide conjugates are as listed below.

TABLE 2

| Name | CpG DNA (nucleotide sequence moiety of structure) | peptide (a moiety excl. N-terminal Cys in peptide) | HPLC condition | Retention time (min.) | Mass spectrometry (MALDI-TOF) $[M-H]^-$ | Remarks |
|---|---|---|---|---|---|---|
| CpG30(S)a-OVApep9 | CpG30(S)a | C-OVA8 | (A) | 16.1 | 11118.3 | Also called Compound 4 |
| CpG30(S)a-mTRP2pep10 | CpG30(S)a | C-TRP2-9 | (B) | 14.0 | 11331.6 | Also called Compound 5 |
| CpG30(S)a-hGP100pep10 | CpG30(S)a | C-gp100-9 | (C) | 16.1 | Not determined | Also called Compound 6 |
| CpG30(S)a-mTRP2pep9 | CpG30(S)a | C-TRP2-8 | (B) | 14.2 | 11248.3 | Also called Compound 1 |
| CpG20(S)a-mTRP2pep9 | CpG20(S)a | C-TRP2-8 | (D) | 12.9 | 8009.5 | Also called Compound 2 |
| CpG30(S)a-hGP100pep9 | CpG30(S)a | C-gp100-8 | (C) | 16.3 | Not determined | Also called Compound 3 |
| CpG30(S)a-CMTRP2-9 | CpG30(S)a | CM-TRP2-9 | (B) | 15.2 | 11464.2 | |
| CpG30(S)a-mTRP2-14 | CpG30(S)a | C-TRP2-13 | (D) | 12.6 | 11739.3 | |
| CpG30(S)a-mTRP2-12 | CpG30(S)a | C-TRP2-11 | (B) | 14.2 | 11524.5 | |

Figure 2:
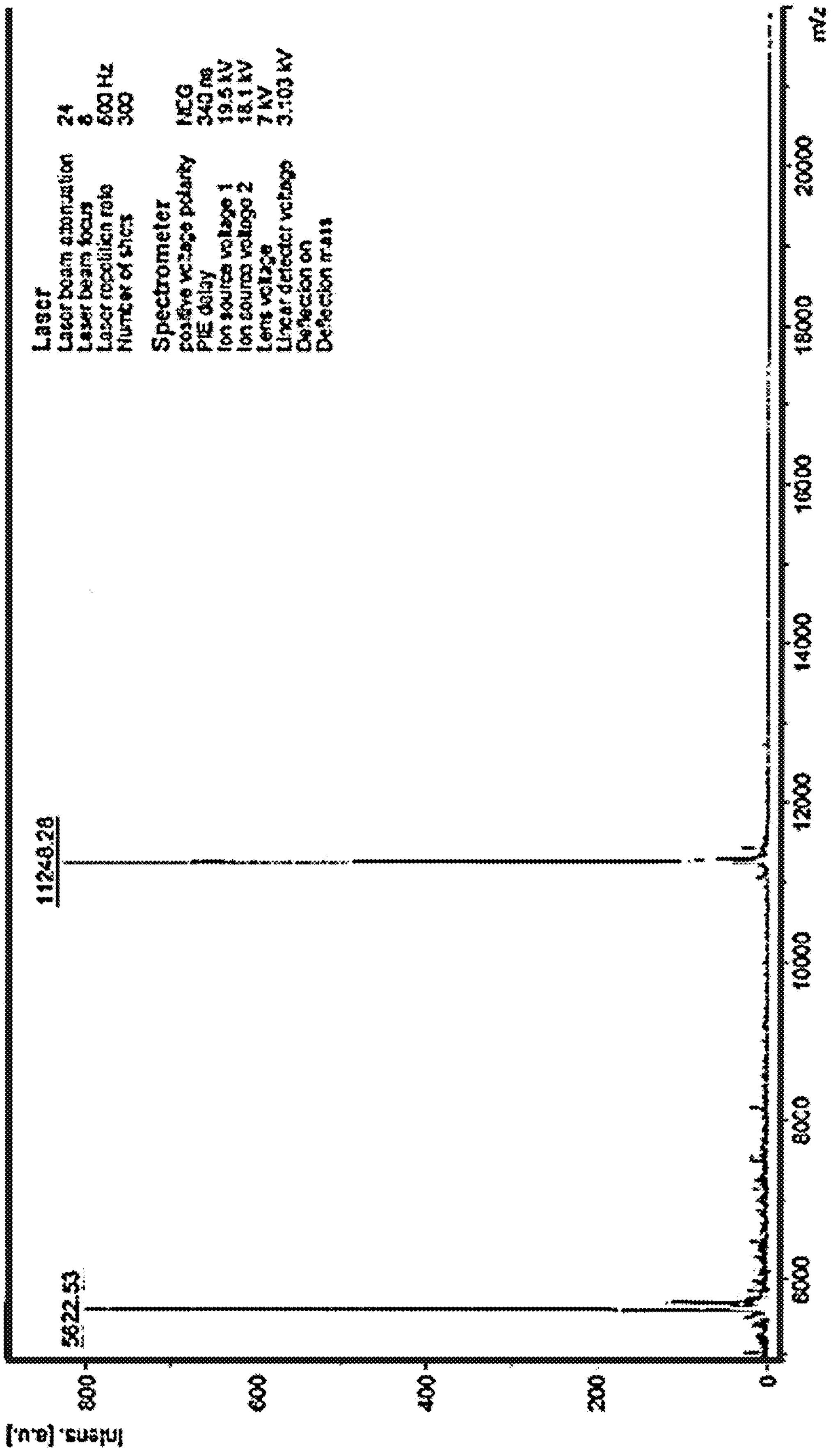
FIG. 2 depicts the mass spectrum obtained by the mass spectrometry of CpG30(S)a-mTRP2pep9 (Compound 1) performed in Example 1.

Also, as an examples of the results of mass spectrometry, a mass spectrum (MALDI-TOF) obtained by the mass spectrometry of CpG30(S)a-mTRP2pep9 (Compound 1) is shown in FIG. 2. The peaks of 11248.28 (monovalent negative ion) and 5622.53 (bivalent negative ion) were detected—this confirmed that a mass spectrum equivalent to that of CpG30(S)a-mTRP2pep9 (theoretical most abundant mass for $C_{369}H_{480}N_{116}O_{174}P_{30}S_{31}$: 11246.56) was obtained.

Example 2: Evaluation of Induction of Cytotoxic T Lymphocytes by CpG DNA(S)-Peptide Conjugates (Evaluation Using mTRP2 Antigens)

(1) Procedure for Evaluating Induction of Cytotoxic T Lymphocytes

A CpG DNA(S)-peptide conjugate as an antigen was intracutaneously administered to mice (C57BL/6 mice (♂, 7 weeks old)). The dose of a CpG DNA(S)-peptide conjugate was 50, 200 or 1000 ng per mouse in terms of peptide (about 0.4, 1.7 or 8.5 μg in terms of CpG30(S)). After one week of administration, splenocytes were isolated from those mice of the same strain not receiving administration, and divided into two aliquots of $2.0\times10^7$ cells/mL. To one aliquot, a peptide as an antigen was added to a concentration of 10 μg/mL, and the mixture was left to stand for 90 minutes to prepare antigen-retaining splenocytes. The other aliquot of splenocytes with no peptide added was regarded as non-antigen-retaining splenocytes. Both of the antigen-retaining splenocytes and the non-antigen-retaining splenocytes were fluorescently modified with 5,6-carboxyfluorescein succinimidyl ester (CFSE). During this process, the concentration of CFSE was varied such that the fluorescence intensity of the antigen-retaining splenocytes (CFSE: 1 μm) was higher than that of the non-antigen-retaining splenocytes (CFSE: 0.1 μm). The same numbers of the antigen-retaining and non-antigen-retaining splenocytes were mixed together, and administered via tail vain at a cell density of $3.0\times10^6$ to the mice which had been administered a CpG DNA(S)-peptide conjugate as an antigen, after one week of administration.

After the lapse of 24 hours from the tail vein administration, splenocytes were isolated from the mice, and evaluated for induced antigen-specific cytotoxic T lymphocyte activity through flow cytometrically quantifying the percentages of antigen-retaining and non-antigen-retaining splenocytes to determine the amount of decrease in antigen-retaining splenocytes. For comparison's sake, other mice were administered PBS (phosphate-buffered saline) instead of a CpG DNA(S)-peptide conjugate, and were regarded as control groups. The control groups were subjected to flow cytometric analysis under the same conditions.

(2) Evaluation of Cytotoxic T Lymphocyte-Inducing Ability of CpG30(S)a-mTRP2pep10

Figure 3B:
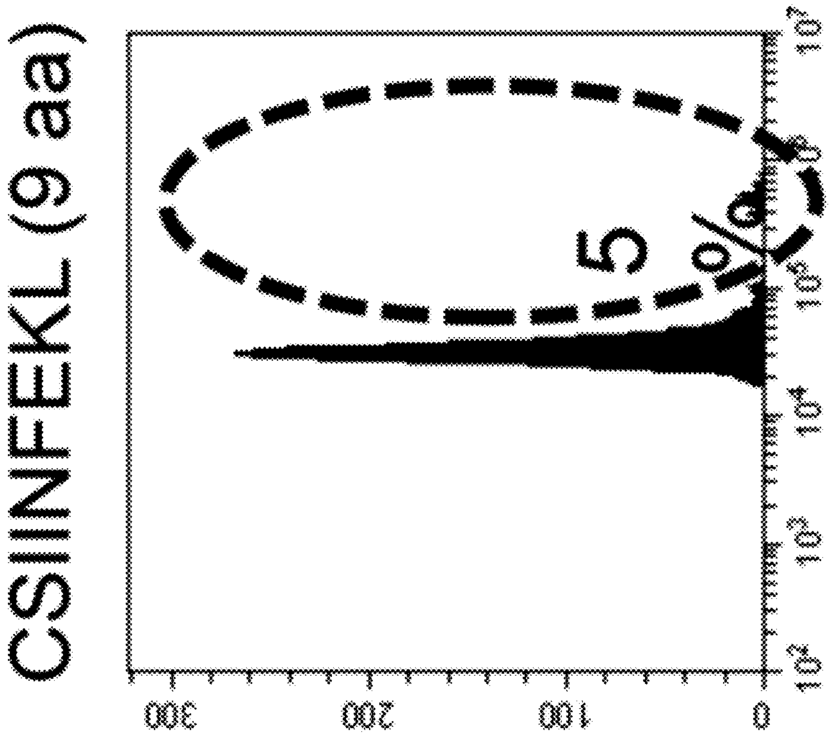
FIGS. 3A-3C depict the results of the flow cytometric analysis performed in (2) in Example 2.
Figure 3A:
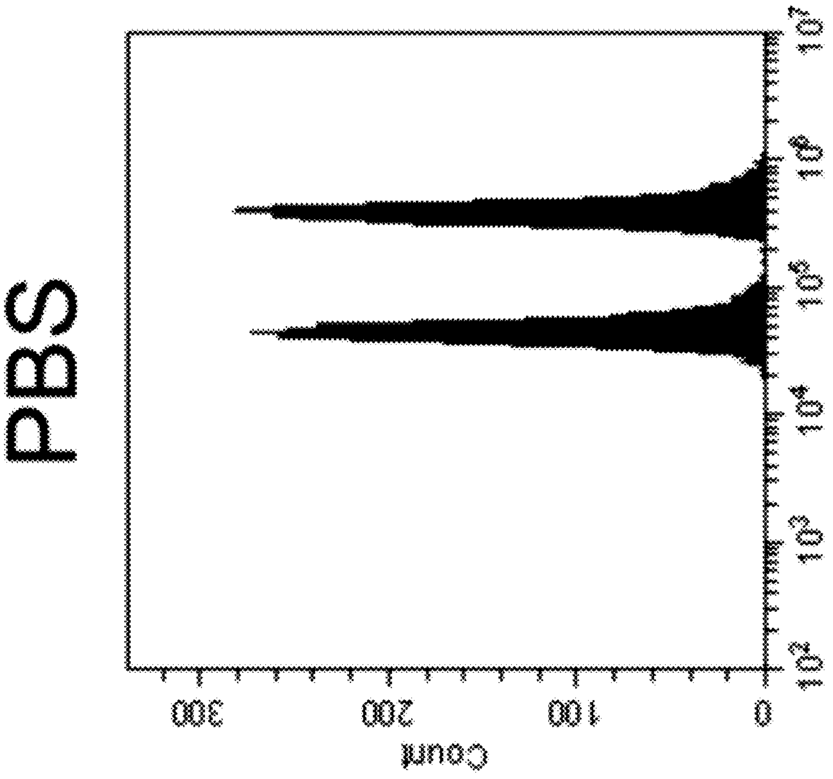
Figure 3C:
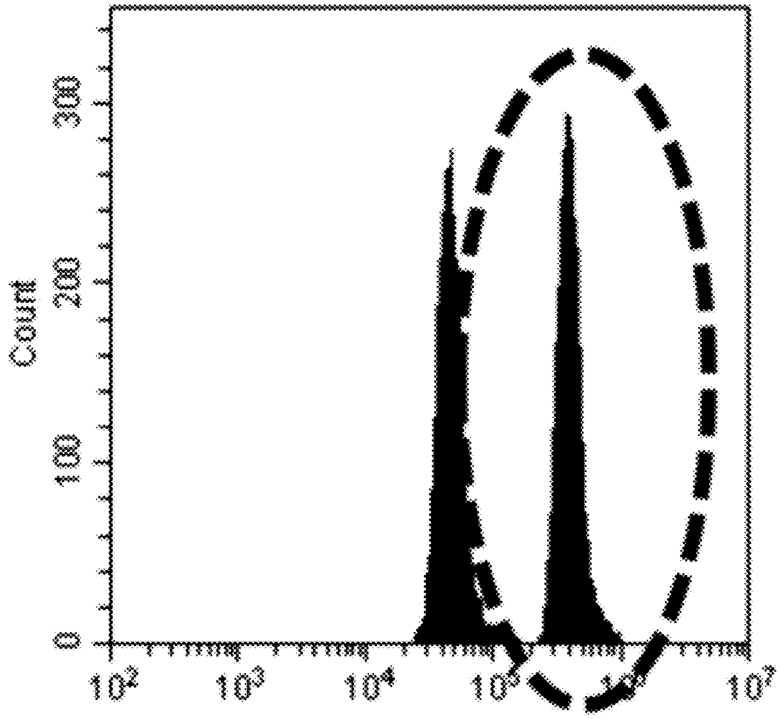

In the earlier application (PCT/JP 2019/038090), the study using OVA-derived antigenic peptides had revealed that the CpG DNA(S)-peptide conjugates had high cytotoxic T lymphocyte (CTL)-inducing ability. However, it was found that some of similar CpG DNA(S)-peptide conjugates prepared with other antigenic peptides did not have adequate CTL-inducing ability (FIGS. 3A-3C).

To be specific, when CpG30(S)a-OVApep9 was evaluated for CTL-inducing ability by using a peptide (OVA peptide 1) consisting of amino acid residues 258 to 265 of ovalbumin (OVA) known as an antigenic peptide, it was observed that antigen-retaining splenocytes disappeared in mice administered the conjugate at a dose of 20 ng per mouse in terms of peptide—this result confirmed that CpG30(S)a-OVApep9 induced potent CTL activity. On the other hand, when CpG30(S)a-mTRP2pep10 (a conjugate prepared with a peptide modified by adding cysteine to the N-terminus of TRP2-9) was evaluated for CTL-inducing ability by using a peptide (TRP2-9) consisting of amino acid residues 180 to 188 (9 amino acids) of mTRP2 known as a melanoma-associated antigen, no CTL activity was observed even in mice administered the conjugate at a dose of 200 ng per mouse in terms of peptide.

(3) Evaluation of Cytotoxic T Lymphocyte-Inducing Ability of CpG30(S)a-mTRP2pep9

In order for a CpG DNA(S)-peptide conjugate to induce CTL activity, it is necessary that after the CpG DNA(S)-peptide conjugate is incorporated in antigen-presenting cells, the peptide moiety should be detached from the polynucleotide moiety and the spacer moiety, and bind to an MHC molecule. It was considered from the results given above that since the peptide C-TRP2-9 (10 amino acids) used to prepare CpG30(S)a-mTRP2pep10 is modified by adding one amino acid to the N-terminus of a peptide having inherent antigenicity, said peptide may not be able to bind to an MHC molecule, or even if it binds to an MHC molecule, it may not be recognized by a T lymphocyte receptor.

Thus, the CpG DNA(S)-peptide conjugate, CpG30(S)a-mTRP2pep9, was prepared using a peptide (C-TRP2-8) modified by deleting one N-terminal residue (serine) from TRP2-9 consisting of 9 amino acids and adding cysteine to the N-terminus, and evaluated for cytotoxic T lymphocyte-inducing ability. The antigen used to prepare antigen-retaining splenocytes was TRP2-9.

Figure 4B:
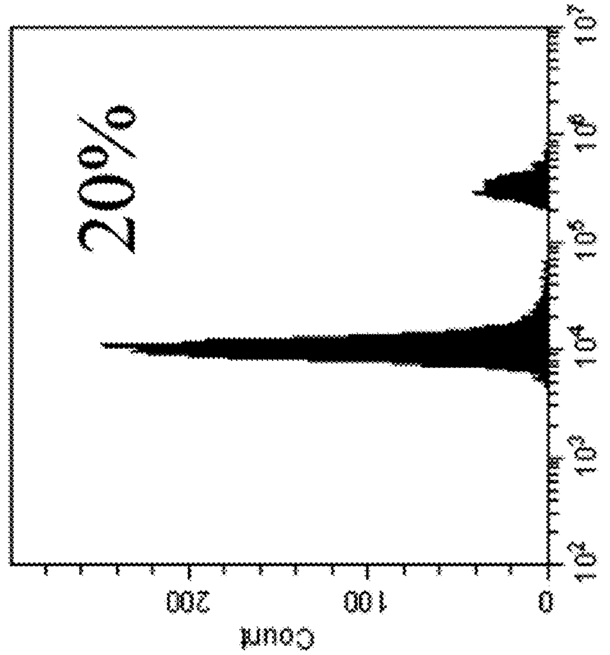
FIGS. 4A-4C depict the results of the flow cytometric analysis performed in (3) in Example 2.
Figure 4A:
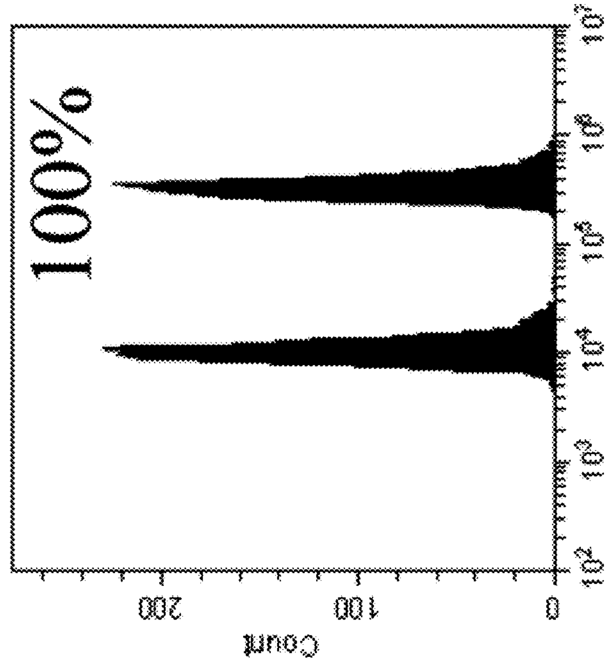
Figure 4C:
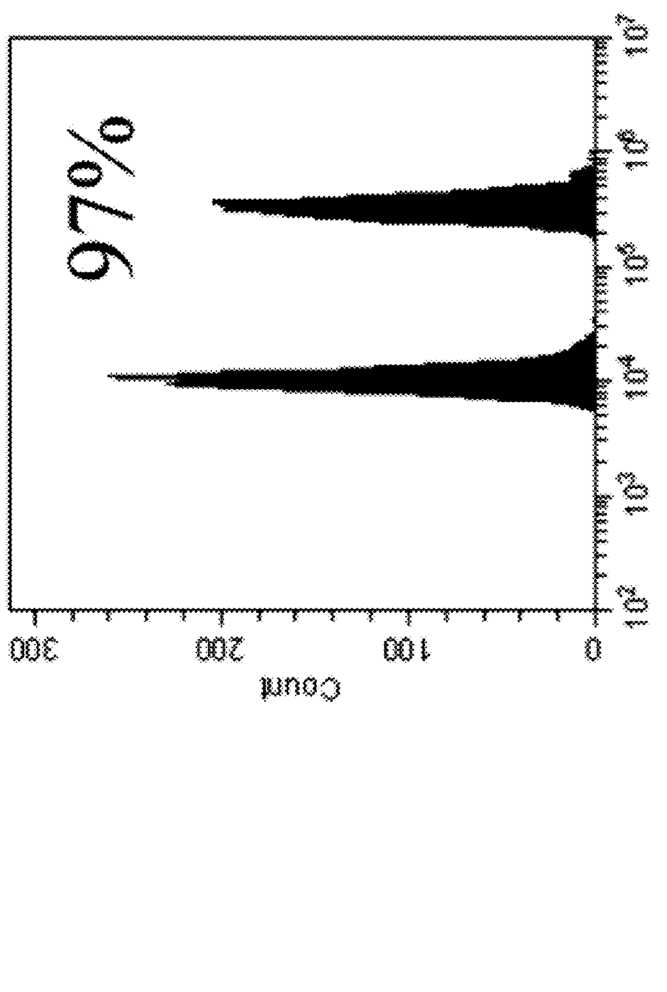

The results of the flow cytometric analysis are shown in FIGS. 4A-4C. A marked decrease in antigen-retaining splenocytes was observed in mice administered CpG30(S)a-mTRP2pep9 at a dose of 200 ng per mouse in terms of peptide—this confirmed that CpG30(S)a-mTRP2pep9 induced potent CTL activity. In contrast, little decrease in antigen-retaining splenocytes was observed in mice administered CpG30(S)a-mTRP2pep10.

(4) Dose Dependence

The cytotoxic T lymphocyte-inducing ability of CpG30(S)a-mTRP2pep9 was evaluated in mice administered the conjugate at varied doses of 50, 200 or 1000 ng per mouse in terms of peptide. The antigen used to prepare antigen-retaining splenocytes was TRP2-9.

Figure 5A:
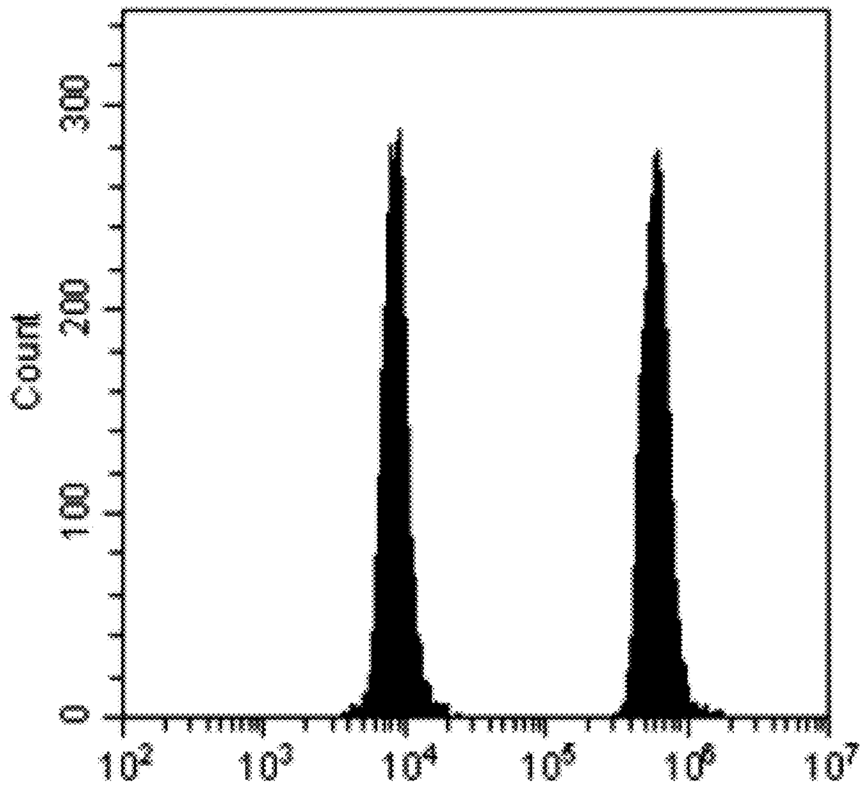
FIGS. 5A and 5B depict the results of the flow cytometric analysis performed in (4) in Example 2.
Figure 5B:
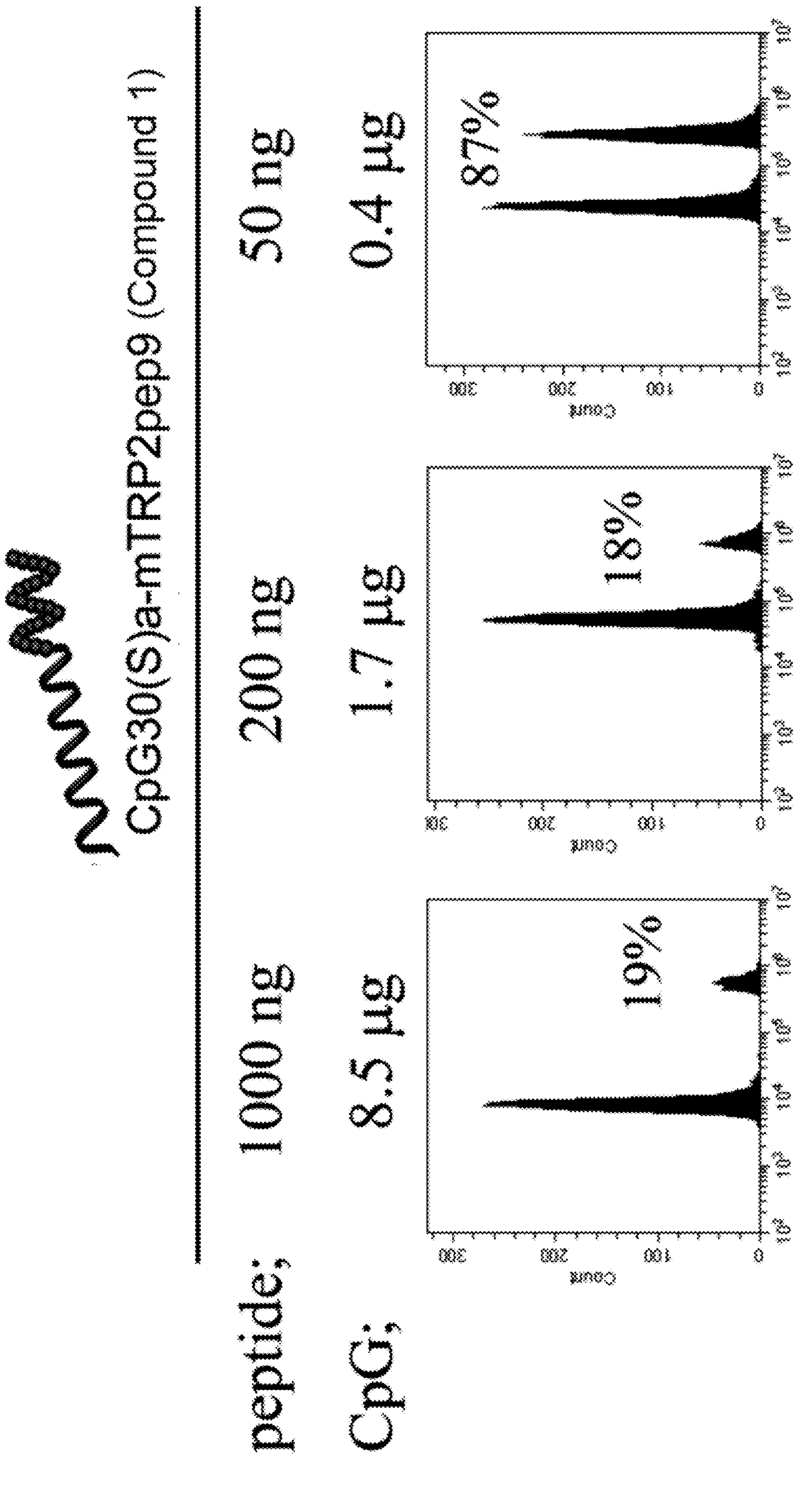

The results of the flow cytometric analysis are shown in FIGS. 5A and 5B. It was observed that there was a dose dependency of the CTL-inducing ability of CpG30(S)a-mTRP2pep9. It was shown that CpG30(S)a-mTRP2pep9 can induce potent CTL activity at a dose of 200 ng.

(5) Dependence on the Nucleotide Sequence Length of CpG DNA

The CpG DNA(S)-peptide conjugate, CpG20(S)a-mTRP2pep9, was prepared by substituting the polynucleotide moiety of CpG30(S)a-mTRP2pep9 with CpG20(S)a having a nucleotide length of 20 nucleotides, and evaluated for cytotoxic T lymphocyte-inducing ability. The antigen used to prepare antigen-retaining splenocytes was TRP2-9.

Figure 6A:
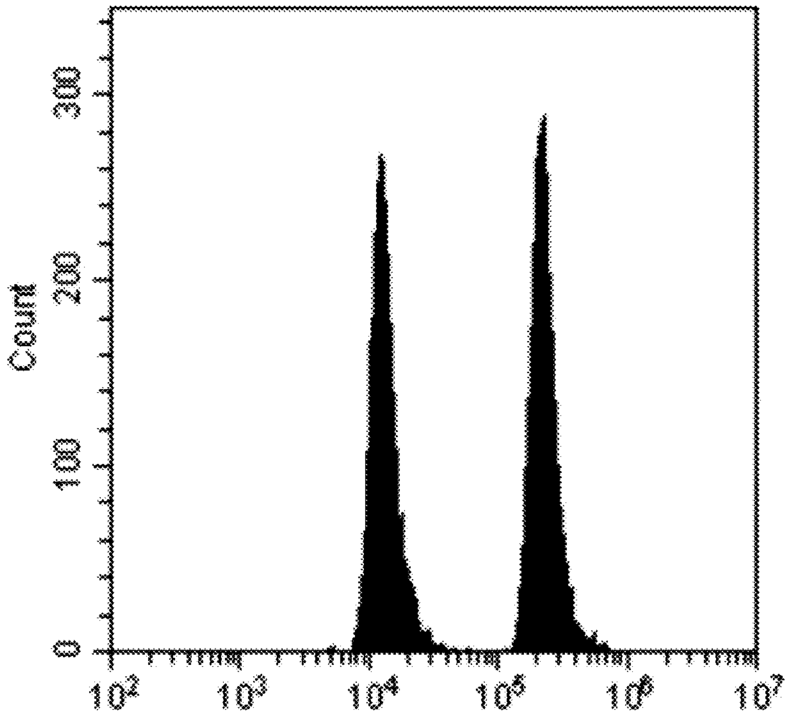
FIGS. 6A-6C depict the results of the flow cytometric analysis performed in (5) in Example 2.
Figure 6B:
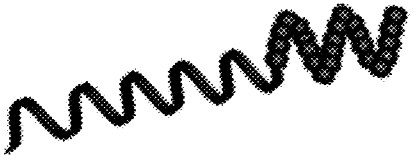
Figure 6B:
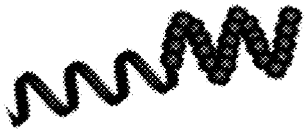
Figure 6B:
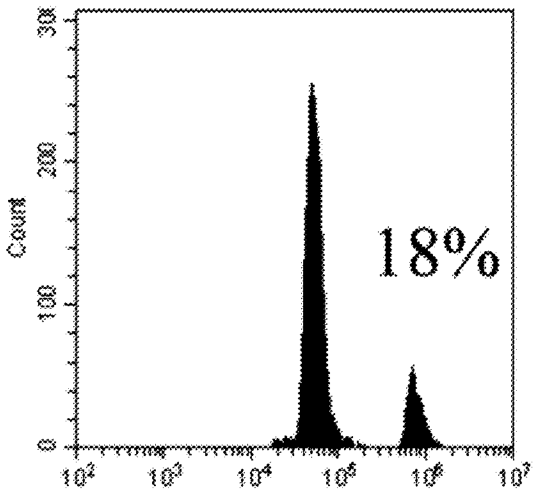
Figure 6C:
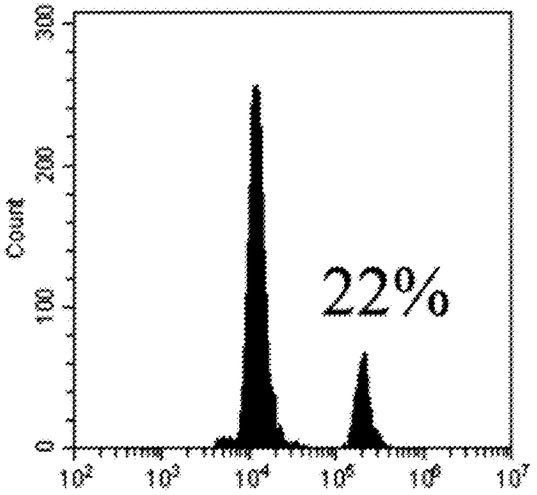

The results of the flow cytometric analysis are shown in FIGS. 6A-6C. It was shown that, similarly to CpG30(S)a-mTRP2pep9, CpG20(S)a-mTRP2pep9 had high CTL-inducing ability.

Example 3: Evaluation of the MHC-1 Binding Ability of the Peptides Used to Prepare the CpG-Peptide Conjugates of the Present Invention (Evaluation of Competitive Inhibition of Binding of OVA Peptide 1 to MHC-1 on DC2.4 Cells)

Murine dendritic cell line, DC2.4 cells, were detached from a dish, and suspended in 1.5 mL tubes at a concentration of $1.5\times10^5$ cells per 200 mL of PBS. To the tubes, OVA peptide 1 was added to a concentration of 0.25 μg/mL, and then any of TRP2-derived peptides (TRP2-9, C-TRP2-9, or C-TRP2-8) was added to a concentration of 2.5 μg/mL in terms of peptide, and the tubes were incubated on ice for 30 minutes. Next, an antibody specific for OVA peptide 1-MHC-1 molecular complexes (fluorescently labeled with phycoerythrin (PE); PE-labeled anti-mouse $OVA_{257-264}$ (SIINFEKL) peptide bound to H-2Kb antibody (ThermoFisher SCIENTIFIC)) (hereinafter referred to as "PE labelled H-2Kb/FIINFEKL") was added, and then antibody-bound OVA peptide 1-MHC-1 complexes on DC2.4 cells were quantified by flow cytometry to thereby evaluate the competitive inhibition activity of the TRP2-derived peptides on binding to MHC-1.

Figure 7A:
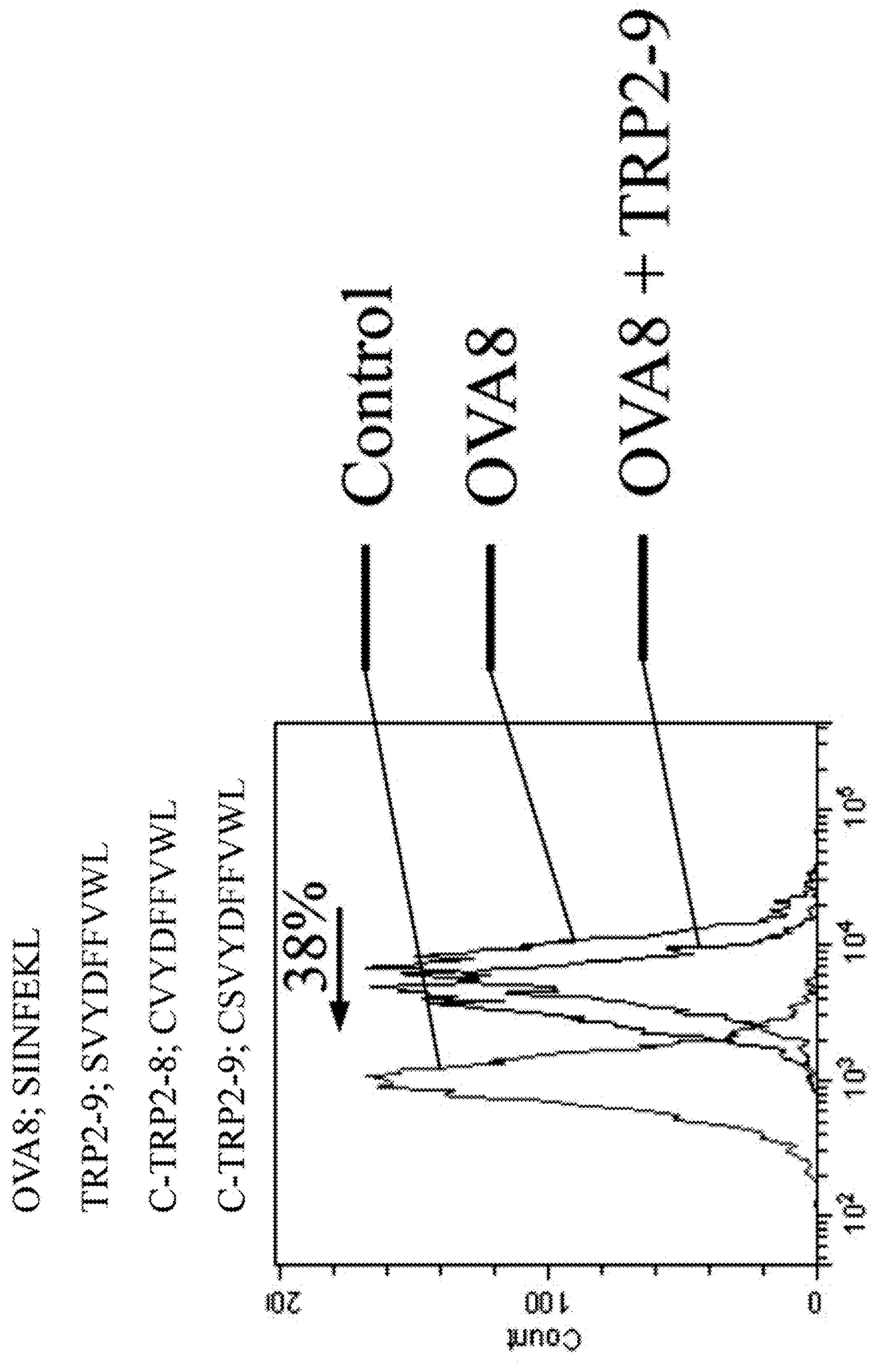
FIGS. 7A-7C depict the results of the flow cytometric analysis performed in Example 3.
Figure 7B:
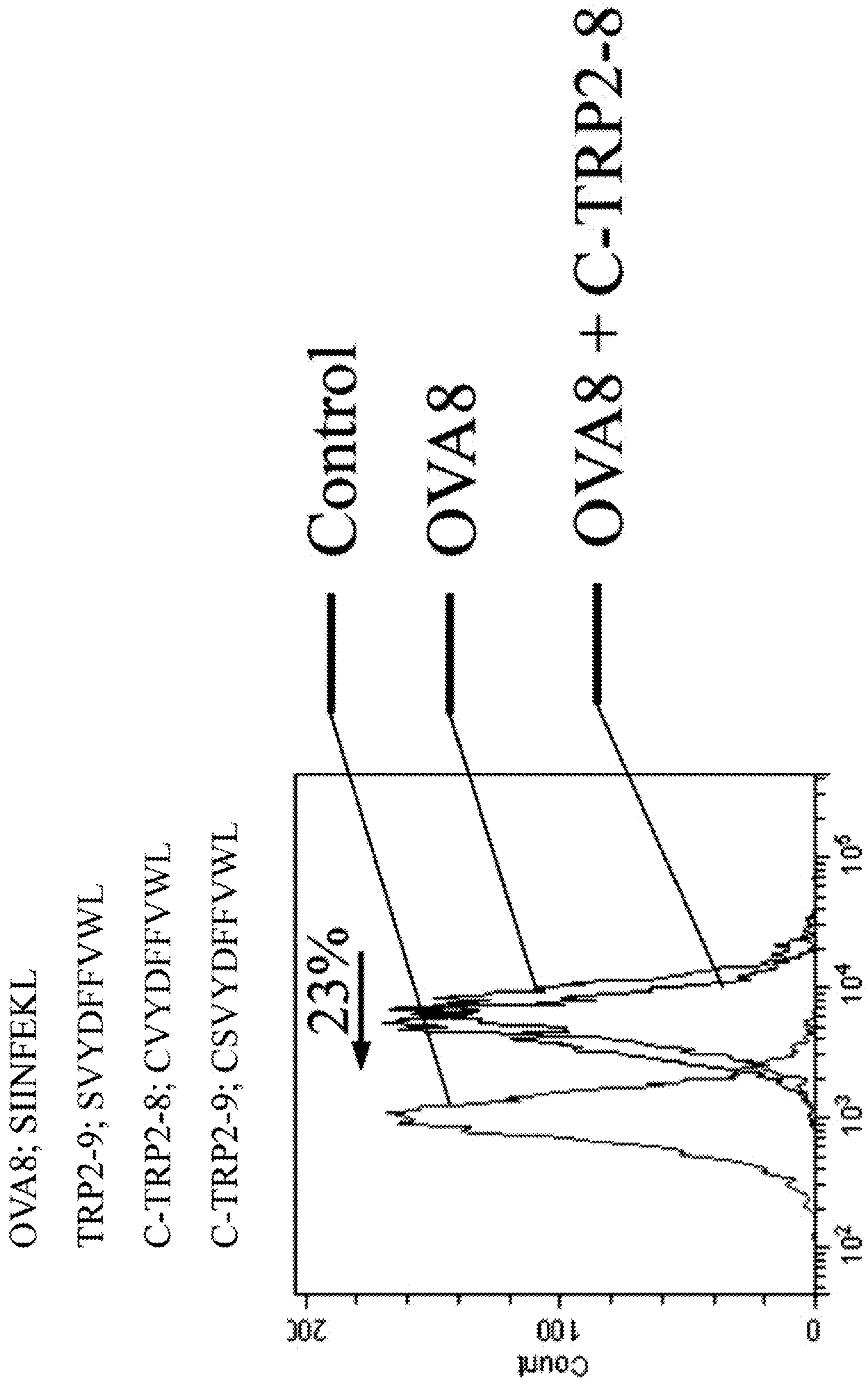
Figure 7C:
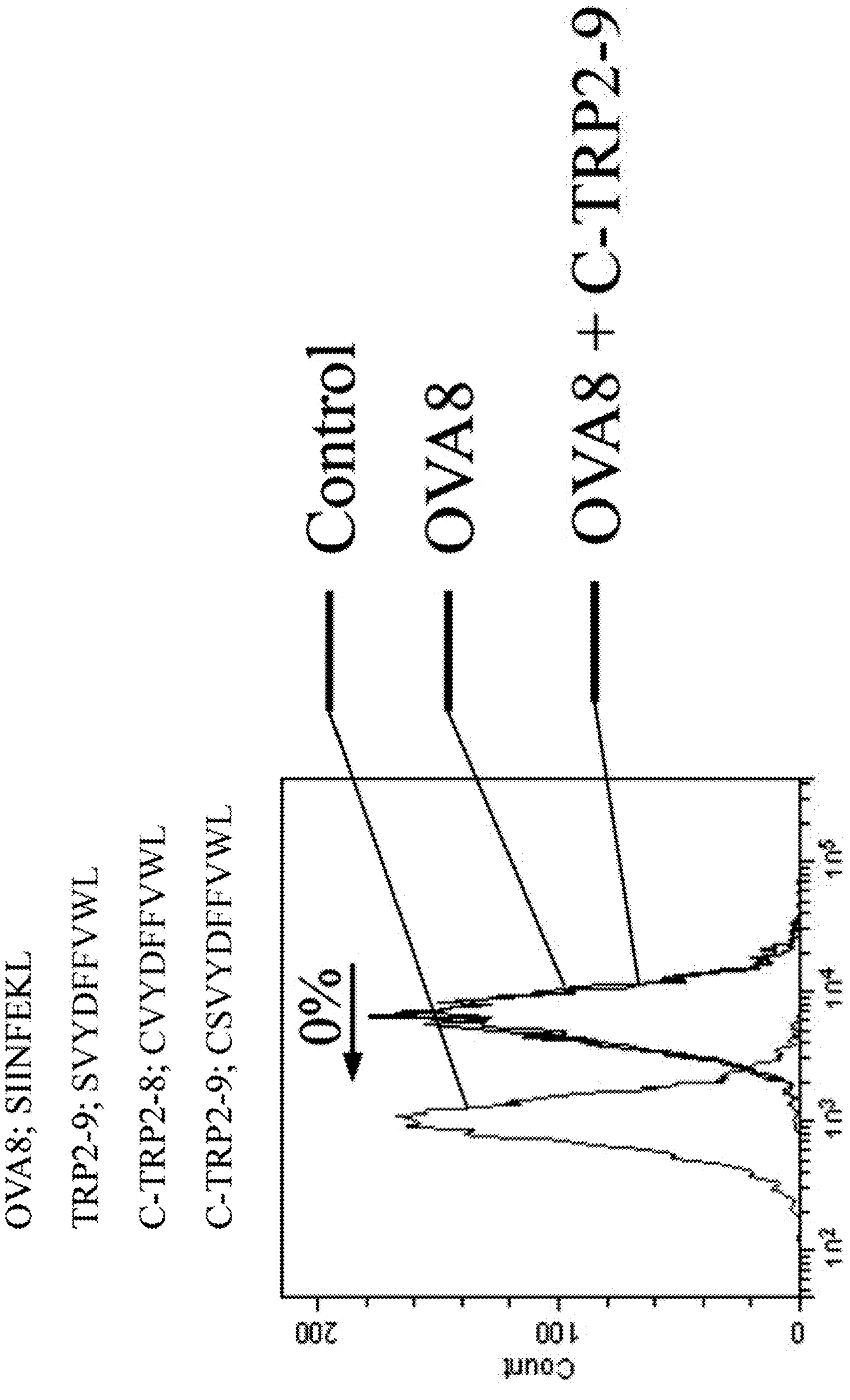

The results of the flow cytometric analysis are shown in FIGS. 7A-7C. In the case of adding TRP2-9, the average fluorescence intensity decreased by 38%—this demonstrated that TRP2-9 had inhibitory activity against binding of OVA peptide 1 to MHC class I molecules, or namely that TRP2-9 was capable of binding to MHC class I molecules. Also, in the case of adding C-TRP2-8, which has the same amino acid length as TRP2-9 but differs in N-terminal amino acid from TRP2-9, the average fluorescence intensity decreased by 23%—this demonstrated the inhibitory activity of C-TRP2-8 against binding of OVA peptide 1 to MHC class I molecules. In contrast, no inhibitory activity was observed for C-TRP2-9 which is longer by one amino acid than TRP2-9.

Therefore, it was suggested that C-TRP2-9 loses its binding ability to MHC-1 while C-TRP2-8 retains its binding ability to MHC-1.

Example 4: Evaluation of Induction of Cytotoxic T Lymphocytes by CpG DNA(S)-Peptide Conjugates (Evaluation Using hGP100)

CpG30(S)a-hGP100pep10 or CpG30(S)a-hGP100pep9 was evaluated for cytotoxic T lymphocyte-inducing ability by following the same procedure as in Example 2. The antigen used to prepare antigen-retaining splenocytes was the peptide hGP100-9, which consists of amino acid residues 25 to 33 (9 amino acids) of hGP100 known as a melanoma-associated antigen.

Figure 8A:
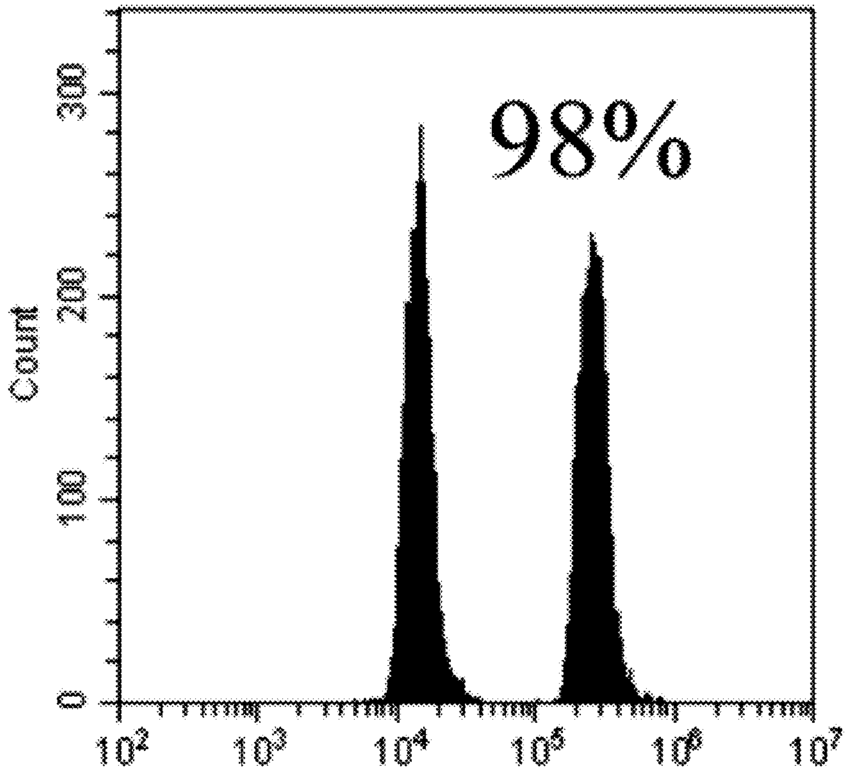
FIGS. 8A-8C depict the results of the flow cytometric analysis performed in Example 4.
Figure 8B:
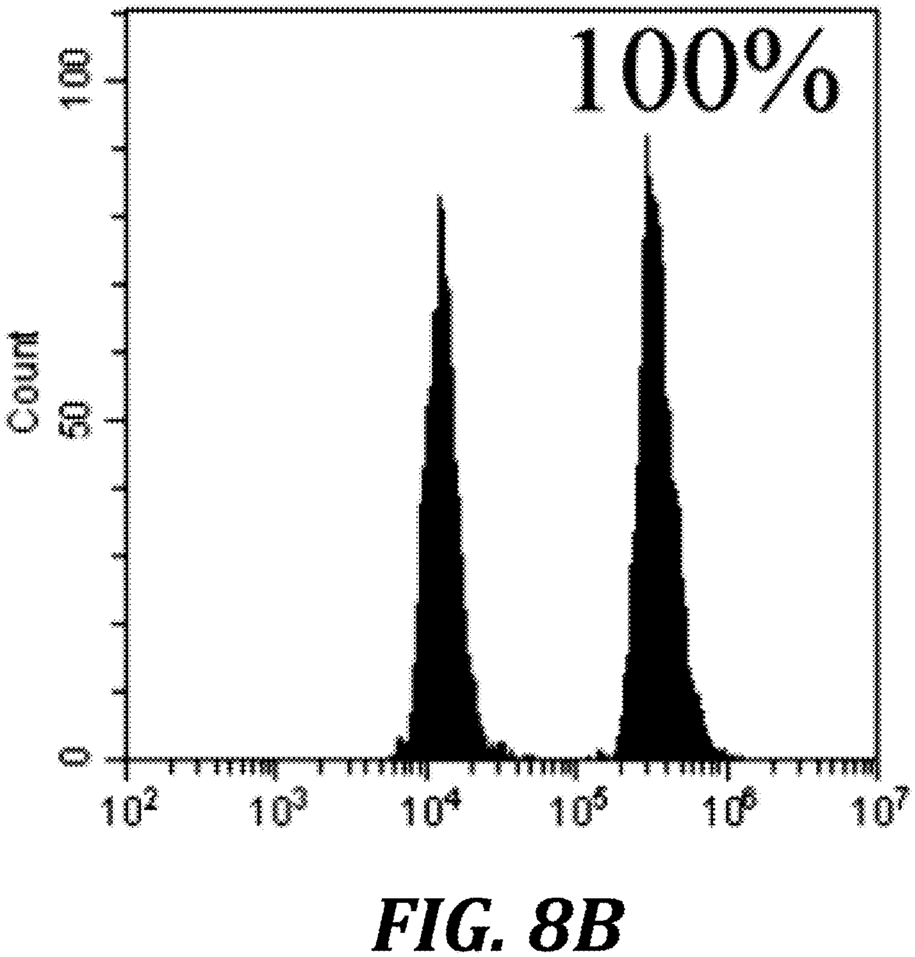
Figure 8C:
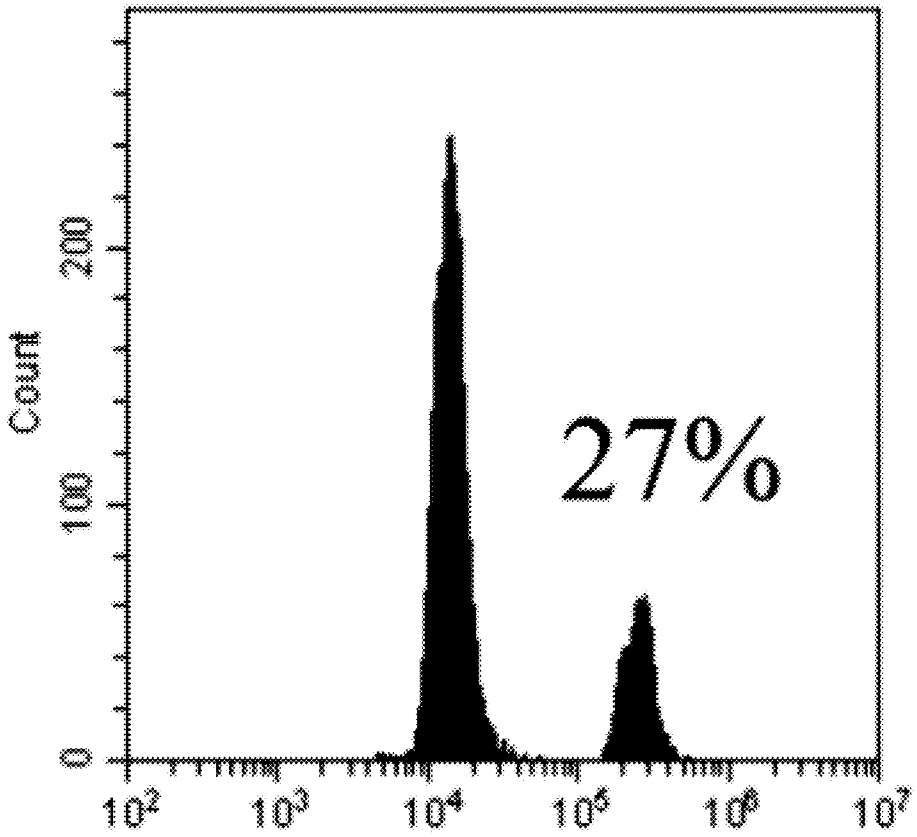
Figure 9A:
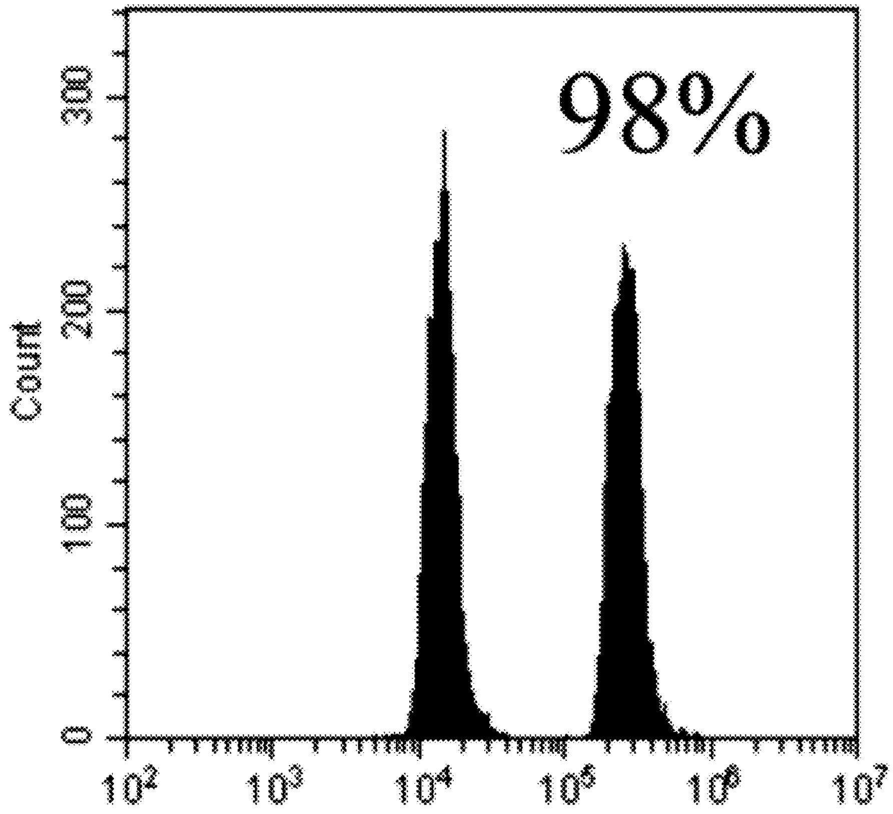
FIGS. 9A and 9B depict the results of the flow cytometric analysis performed in Example 4.
Figure 9B:
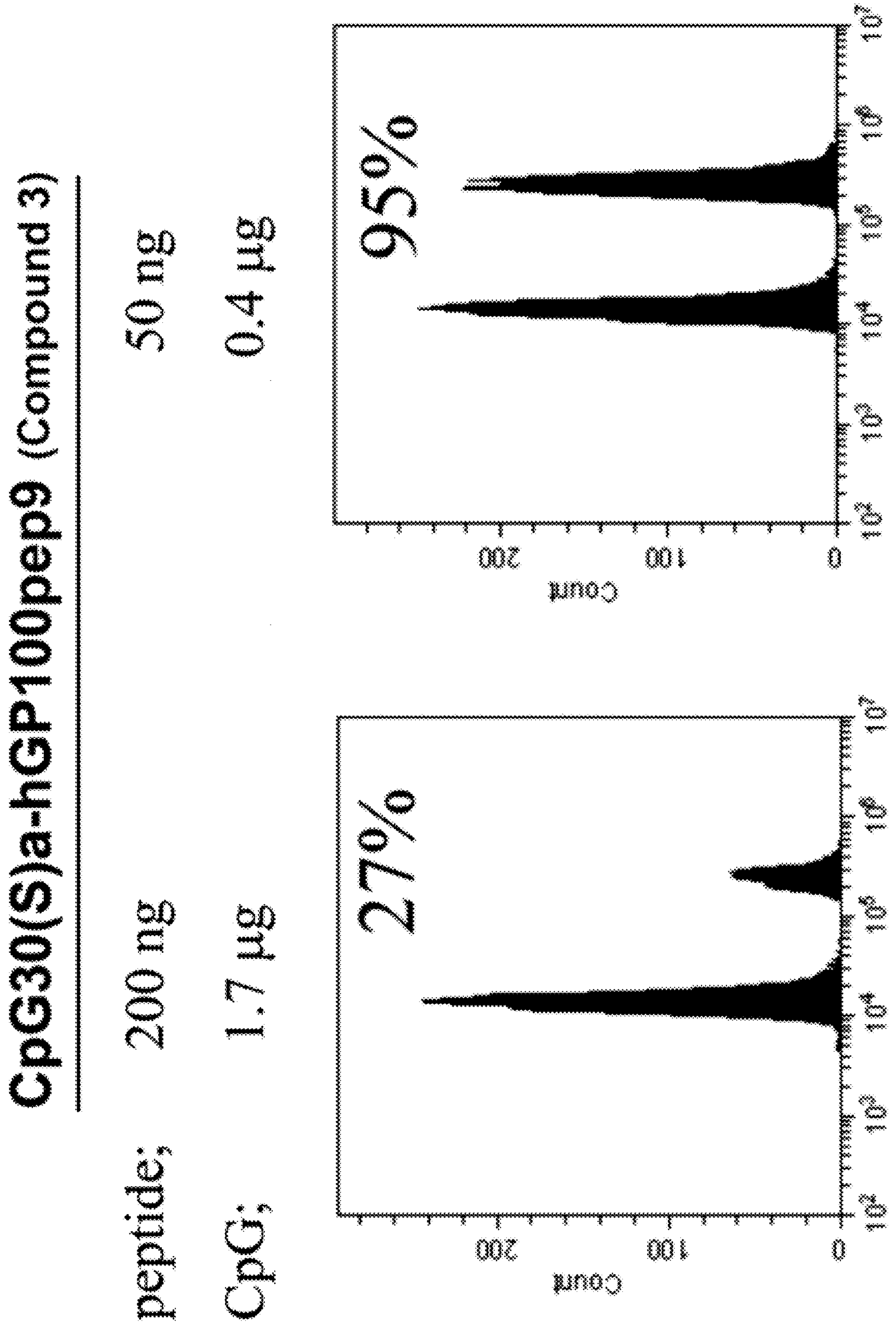

The results of the flow cytometric analysis are shown in FIGS. 8A-8C and FIGS. 9A and 9B. Like in the case of the evaluation using mTRP2 antigens, a decrease in antigen-retaining splenocytes was observed in mice administered CpG30(S)a-hGP100pep9 at a dose of 200 ng per mouse in terms of peptide—this confirmed that CpG30(S)a-hGP100pep9 induced CTL activity, whereas little decrease in antigen-retaining splenocytes was observed in mice administered CpG30(S)a-hGP100pep10 (FIGS. 8A-8C). Also, it was observed that there was a dose dependence of the CTL-inducing ability of CpG30(S)a-hGP100pep9, which demonstrated that CpG30(S)a-hGP100pep9 can induce potent CTL activity at a dose of 200 ng (FIGS. 9A and 9B).

Reference Example 1: Evaluation of Induction of Cytotoxic T Lymphocytes by CpG30(S)a-CMTRP2-9

Endoplasmic reticulum aminopeptidase (ERAP) is involved in the presentation of an antigenic peptide by MHC-1 molecules. An antigenic peptide precursor is trimmed from the N-terminus by ERAP to yield a peptide with a length suitable for binding to MHC-1. With regard to this process, it has been reported that when alanine, leucine or methionine is inserted into the C-terminal side of cysteine in an antigenic peptide precursor having cysteine at the N-terminus, the modified peptide precursor becomes more susceptible to trimming by ERAP (vid., WO 2014/157704). It was considered from the results shown in FIG. 3 that the CTL-inducing ability of CpG30(S)a-mTRP2pep10 may be improved if alanine, leucine or methionine is inserted into the C-terminal side of N-terminal cysteine of C-TRP2-9 so that the modified peptide can become more susceptible to trimming by ERAP.

Thus, the CpG DNA(S)-peptide conjugate, CpG30(S)a-CMTRP2-9, was prepared using CM-TRP2-9, which is a peptide modified by inserting methionine into the C-terminal side of N-terminal cysteine of C-TRP2-9, and evaluated for CTL-inducing ability. The antigen used to prepare antigen-retaining splenocytes was TRP2-9.

Figure 10A:
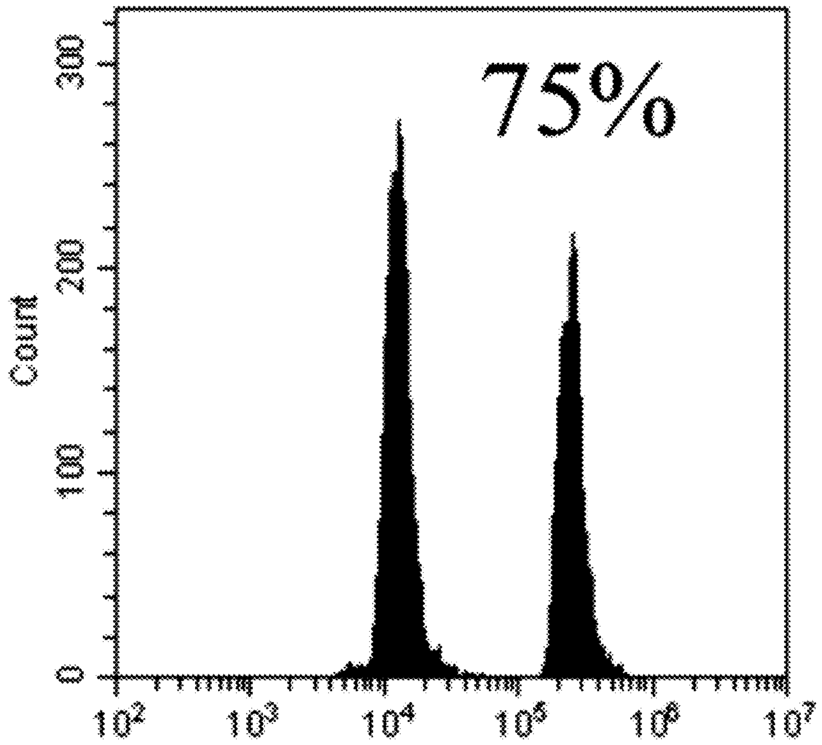
FIGS. 10A and 10B depict the results of the flow cytometric analysis performed in Reference Example 1.
Figure 10B:
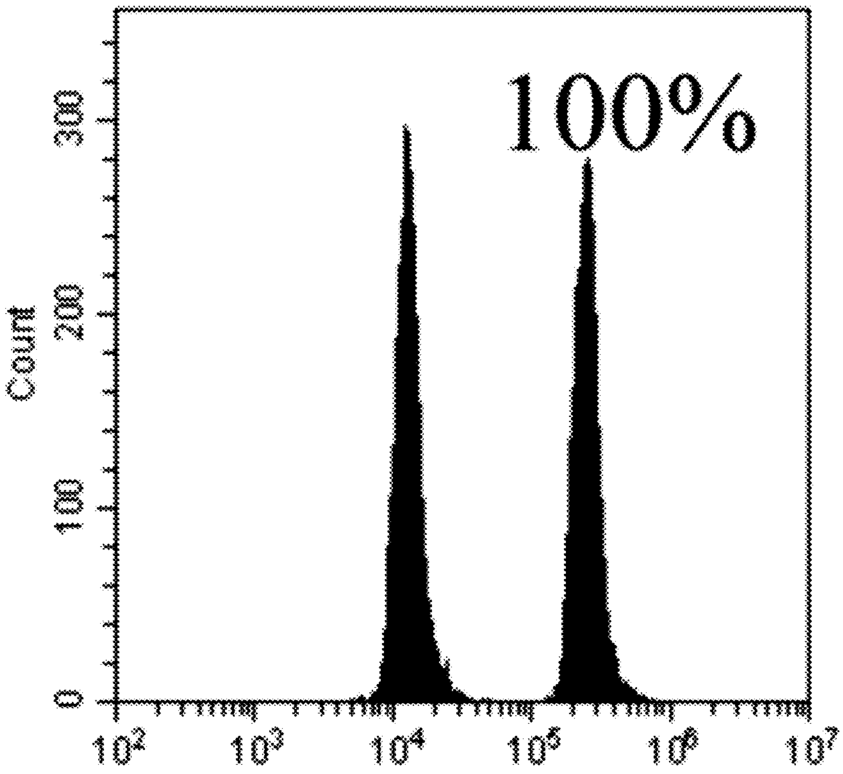

The results of the flow cytometric analysis are shown in FIGS. 10A and 10B. No sufficient decrease in antigen-retaining splenocytes was observed even in mice administered CpG30(S)a-CMTRP2-9 at a dose of 1000 ng per mouse in terms of peptide. Little decrease in antigen-retaining splenocytes was observed in mice administered 200 ng of this conjugate. Some results of the in vitro evaluation using the peptide CM-TRP2-9 suggested that said peptide became susceptible to cleavage by ERAP, but the in vivo evaluation suggested that the CTL-inducing ability of the CpG DNA(S)-peptide conjugate cannot be fully improved using CM-TRP2-9.

Reference Example 2: Evaluation of Induction of Cytotoxic T Lymphocytes by CpG30(S)a-mTRP2-14 and CpG30(S)a-mTRP2-12

It has been reported that the susceptibility of a peptide to trimming by ERAP varies with the chain length of the peptide, and that 9-16 amino acid-long peptides are suitable substances for ERAP (*Proc. Natl. Acad. Sci. USA.* 102(47): 17107-12 (2005)).

Thus, the CpG DNA(S)-peptide conjugates, CpG30(S)a-TRP2-12 and CpG30(S)a-TRP2-14, were prepared using C-TRP2-11 and C-TRP2-13, respectively, which are peptides in which a region on the N-terminal side of the TRP2-derived sequence is longer by 2 or 4 amino acids than that of C-TRP2-9, and the prepared conjugates were evaluated for CTL-inducing ability. The antigen used to prepare antigen-retaining splenocytes was TRP2-9.

Figure 11A:
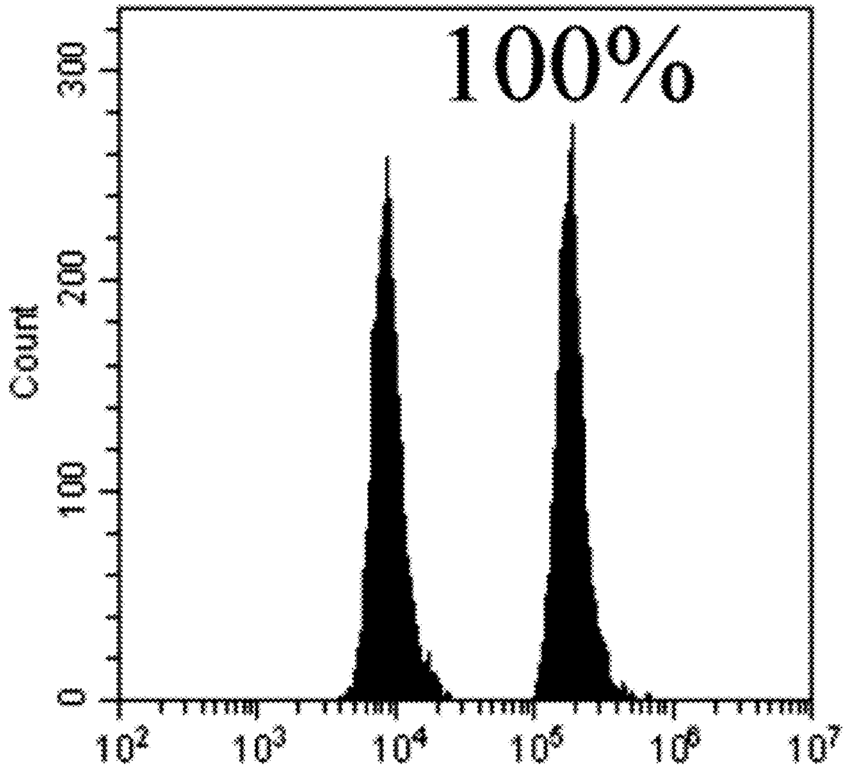
FIGS. 11A and 11B depict the results of the flow cytometric analysis performed in Reference Example 2.
Figure 11B:
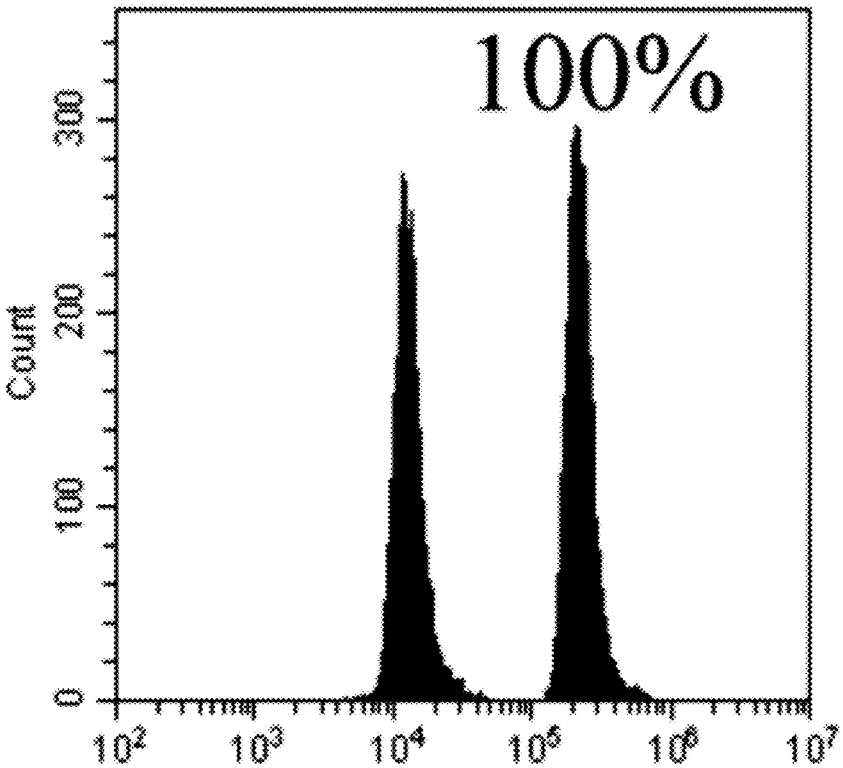
Figure 12A:
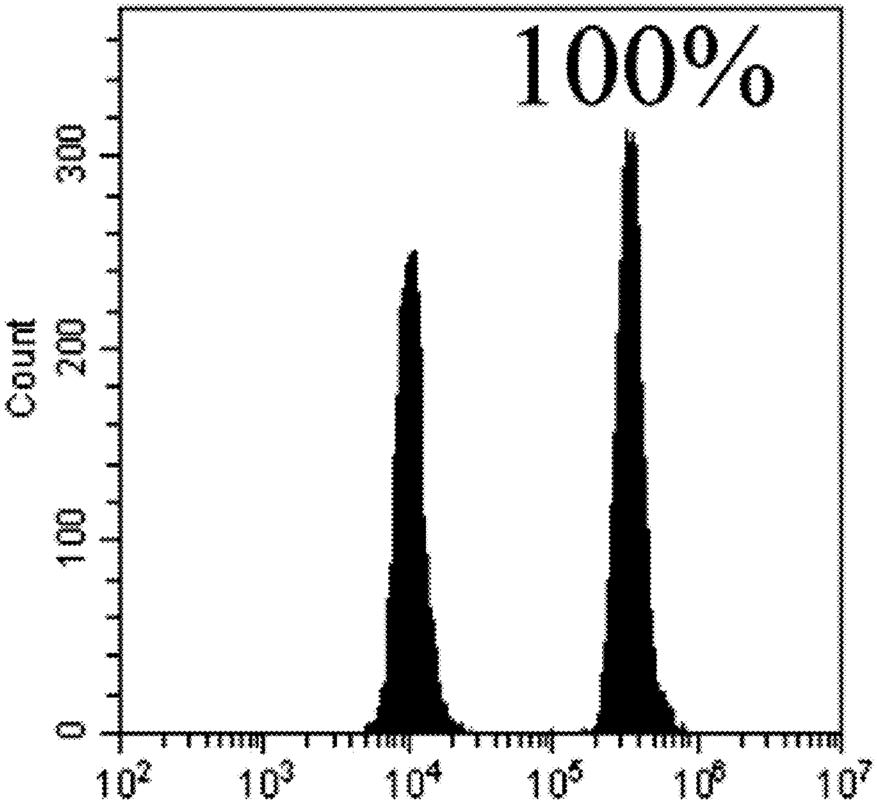
FIGS. 12A-12E depict the results of the flow cytometric analysis performed in Example 5.
Figure 12B:
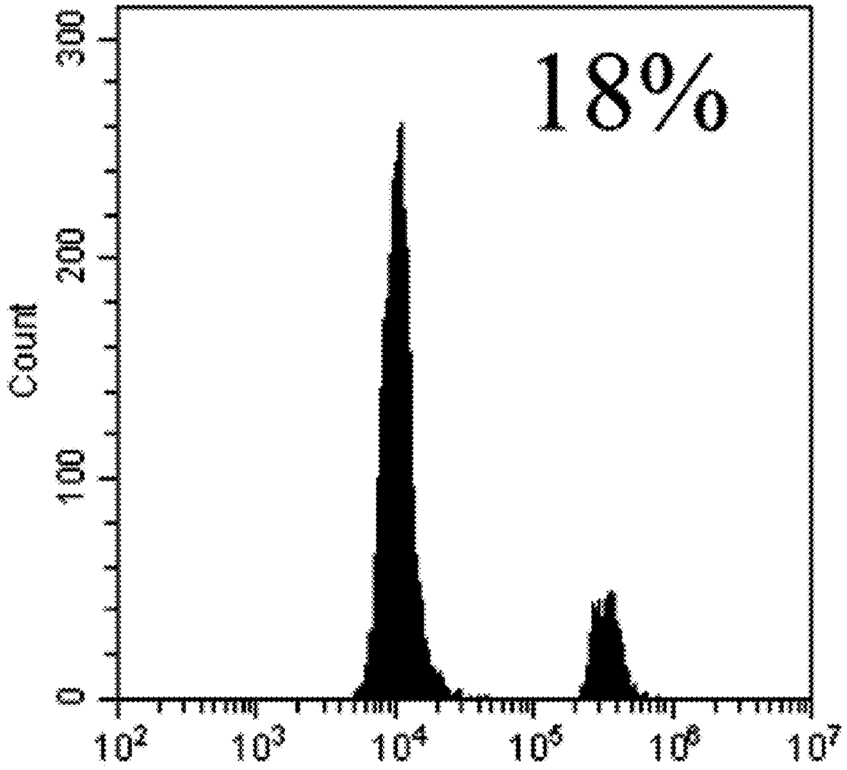
Figure 12C:
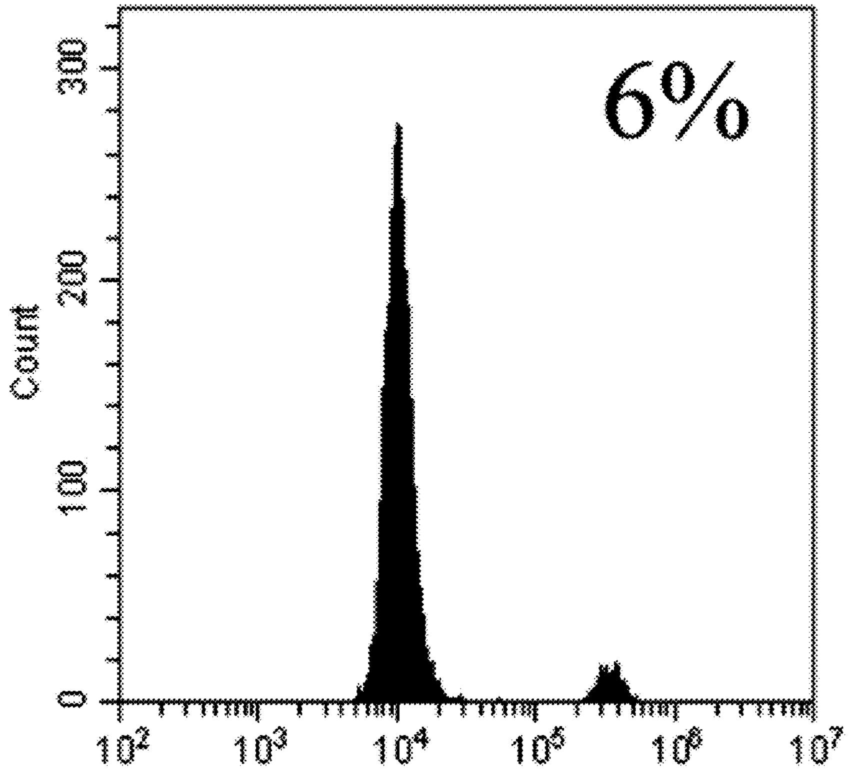
Figure 12D:
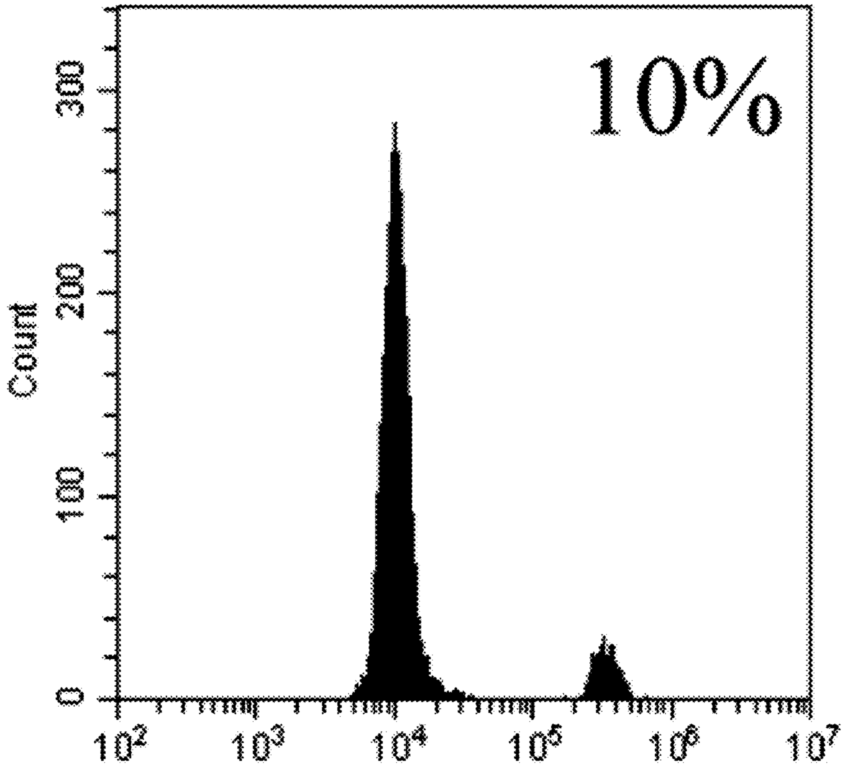
Figure 12E:
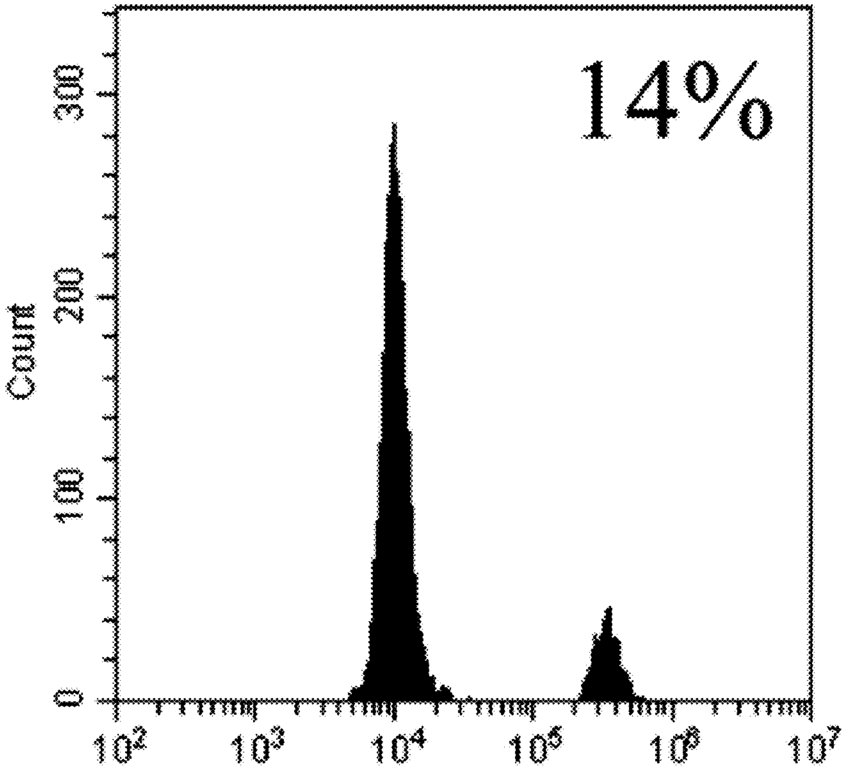
Figure 13A:
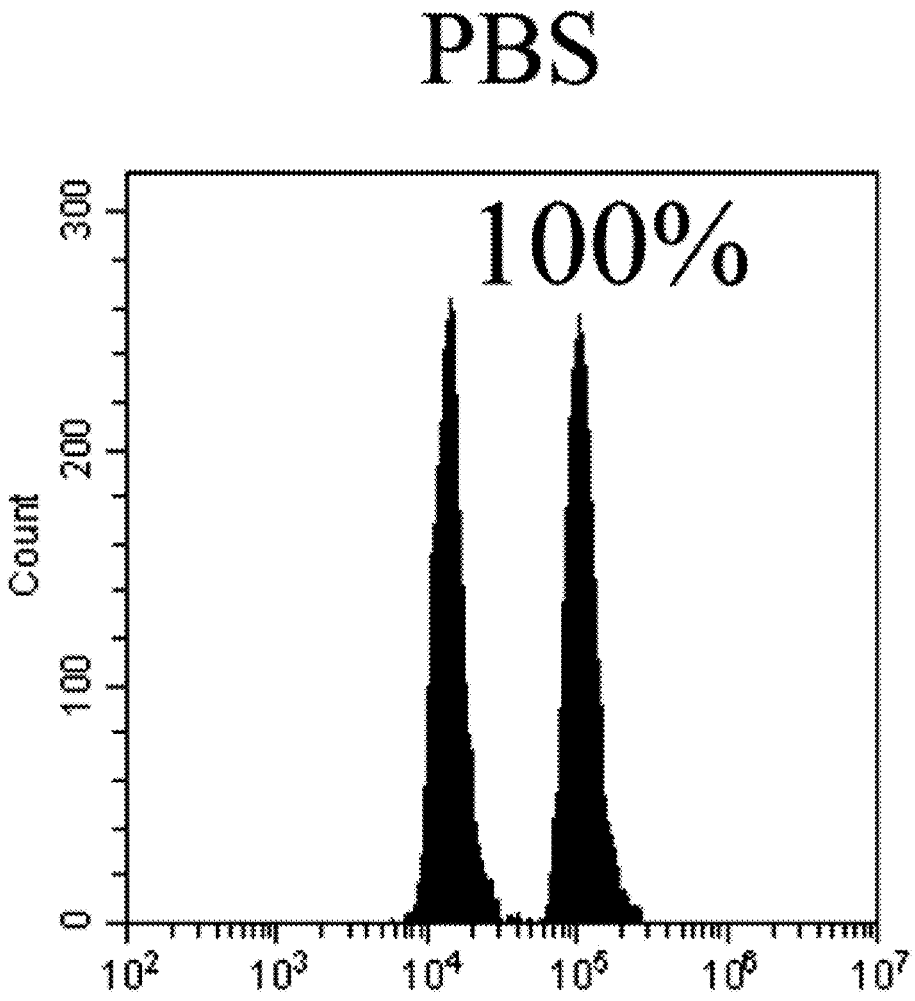
FIGS. 13A-13D depict the results of the flow cytometric analysis performed in Example 6.
Figure 13B:
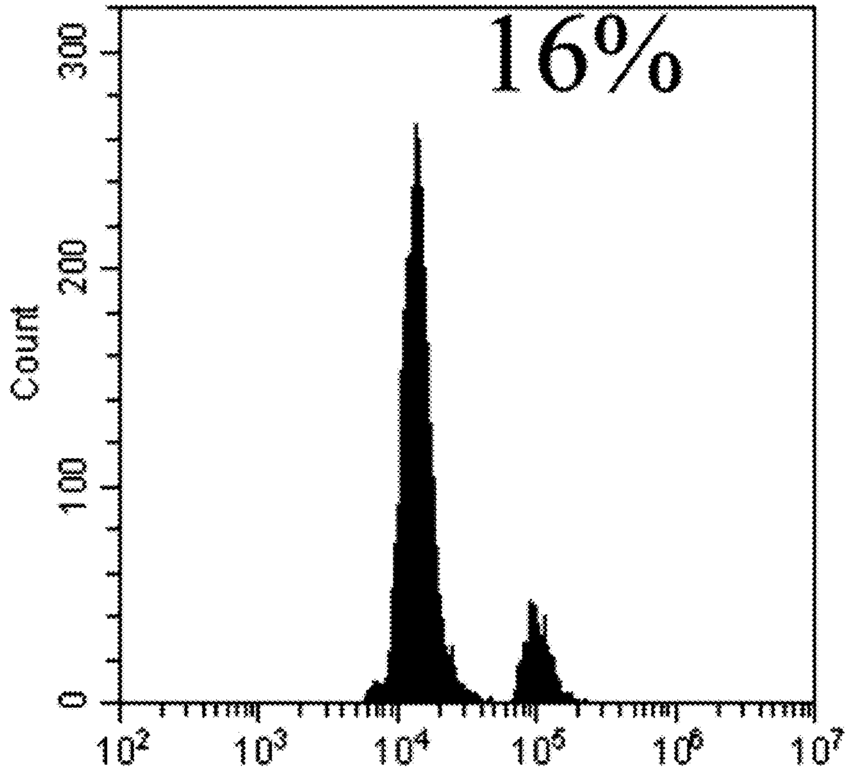
Figure 13C:
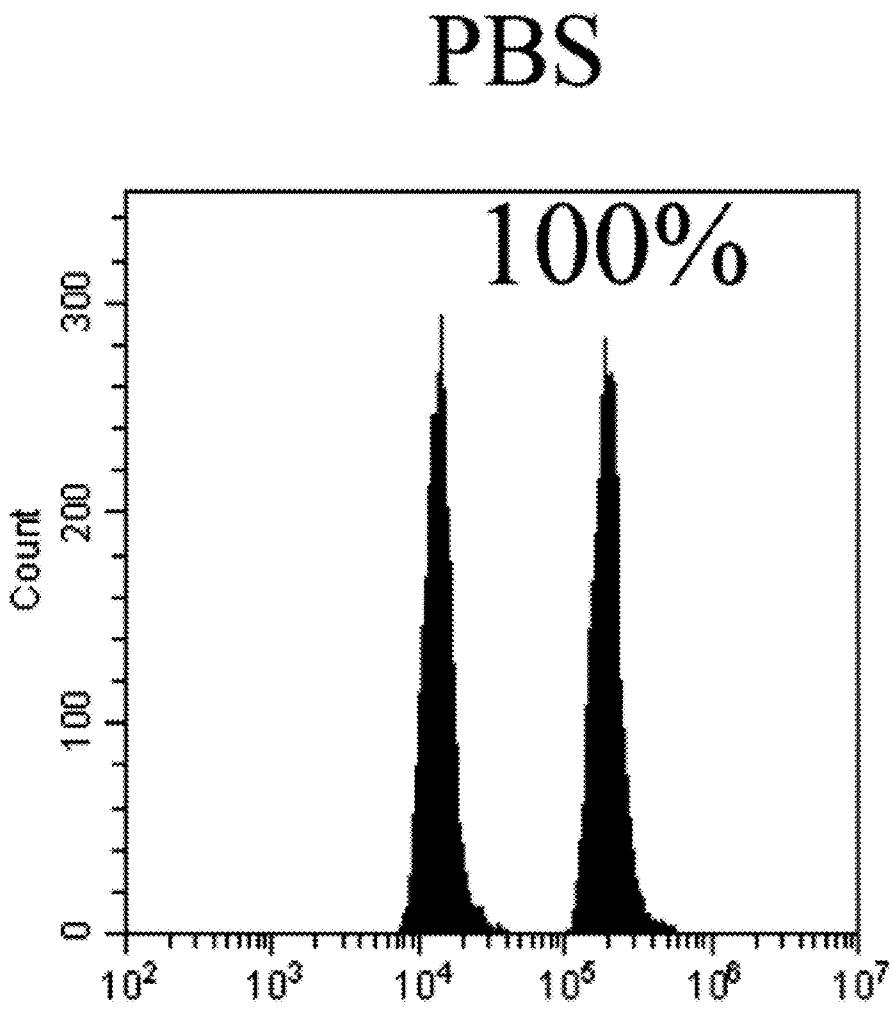
Figure 13D:
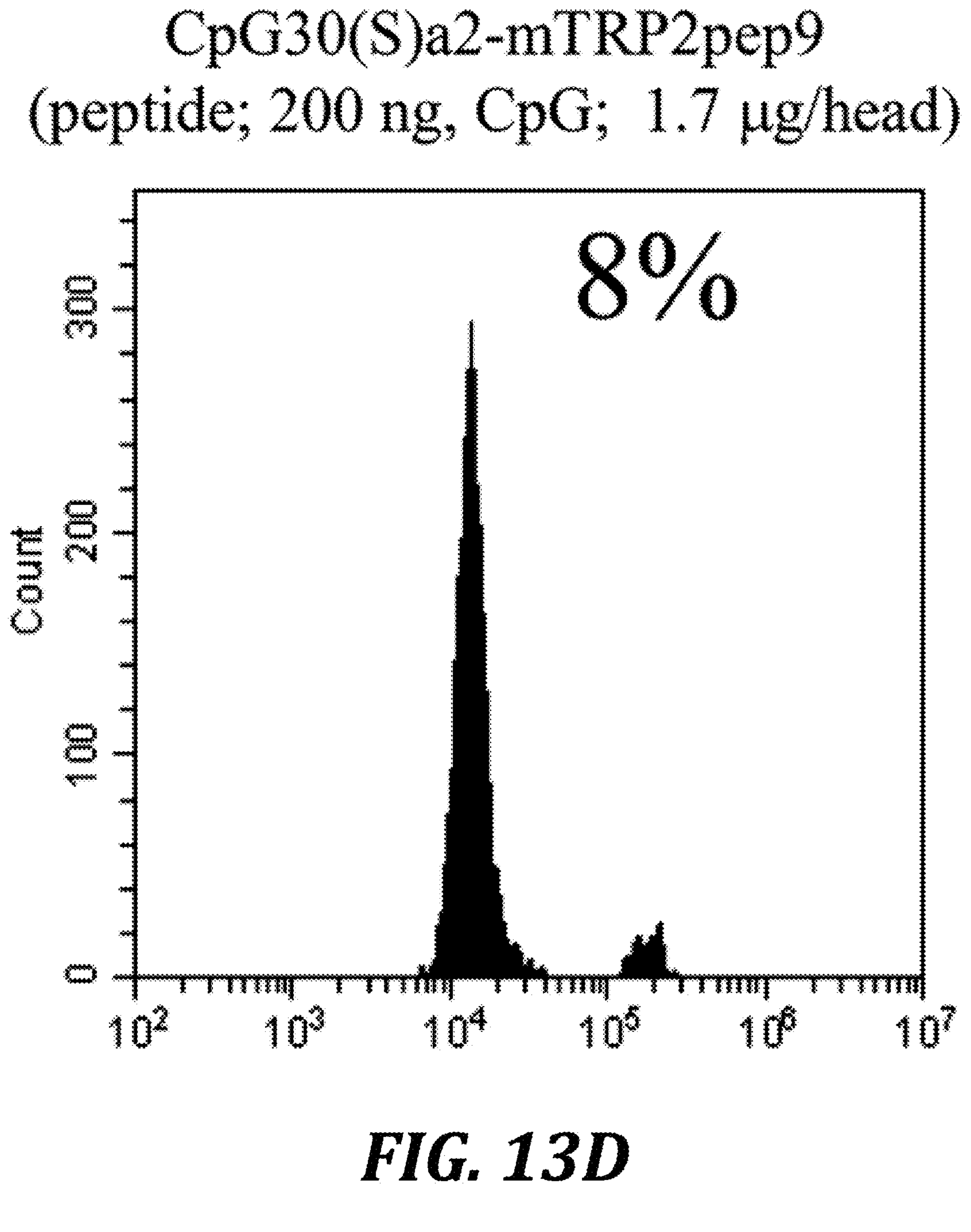

The results of the flow cytometric analysis are shown in FIGS. 11A and 11B. No decrease in antigen-retaining splenocytes was observed in mice administered either of the prepared CpG DNA(S)-peptide conjugates. Some results of the in vitro evaluation using the peptide C-TRP2-11 or C-TRP2-13 suggested that the peptide became susceptible to cleavage by ERAP, but the in vivo evaluation using the prepared CpG DNA(S)-peptide conjugates suggested that the CTL-inducing ability of the CpG DNA(S)-peptide conjugates cannot be fully improved using C-TRP2-11 or C-TRP2-13.

Example 5: Synthesis of CpG DNA(S)-Peptide Conjugates Containing any Other CpG Motifs than K3-Derived CpG Motifs, and Evaluation of the Cytotoxic T Lymphocyte-Inducing Ability of Said Conjugates (1) Synthesis Procedure CpG DNA(S)-peptide conjugates containing any other CpG motifs than K3-derived CpG motifs were synthesized by following the same procedure as in Example 1. The synthesized compounds are represented by the formulas given below, and shown in Table 3. The N-terminal modified peptide used was C-TRP2-8 (vid., (2) in Example 1).

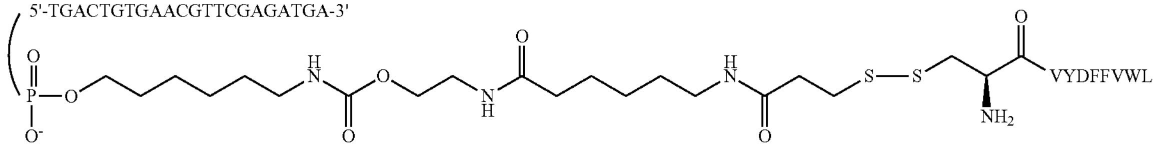

ISS1018-mTRP2pep9

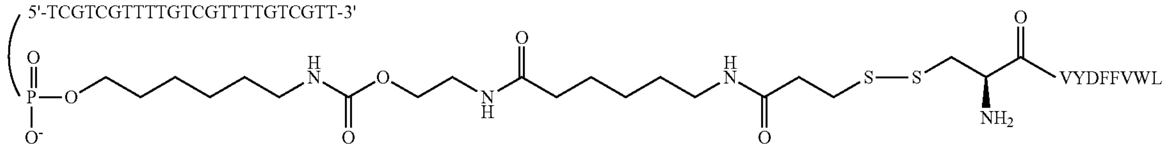

ODN2006-mTRP2pep9

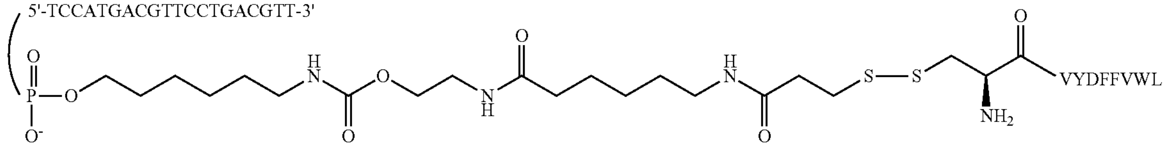

ODN1826-mTRP2pep9

TABLE 3

| Name | CpG DNA | peptide (a moiety excl. N-terminal Cys in pepetide) | HPLC condition | Retention time (min.) | Mass spectrometry (MALDI-TOF) $[M-H]^-$ |
|---|---|---|---|---|---|
| ISS1018-mTRP2pep9 | ISS1018 | C-TRP2-8 | B | 15.1 | 8808.2 |
| ODN2006-mTRP2pep9 | ODN2006 | C-TRP2-8 | B | 15.0 | 9358.6 |
| ODN1826-mTRP2pep9 | ODN1826 | C-TRP2-8 | B | 15.5 | 8024.8 |

(2) Test Procedure

By following the same procedure as in Example 2, ISS1018-mTRP2pep9, ODN2006-mTRP2pep9, and ODN1826-mTRP2pep9 were evaluated for cytotoxic T lymphocyte-inducing ability. The dose of the conjugates administered was 200 ng per mouse in terms of peptide. As a control, CpG30(S)a-mTRP2pep9 (a conjugate containing K3-derived CpG motifs; vid., Example 1) was used.

The results are shown in FIGS. 12A-12E. It was shown that like the conjugate containing K3-derived CpG motifs, all of the compounds synthesized in (1) have cytotoxic T lymphocyte-inducing ability.

Example 6: Synthesis of Conjugates Having an ssH Amino Linker Moiety in which a Phosphate Group is Substituted with a Thiophosphate Group, and Evaluation of the Cytotoxic T Lymphocyte-Inducing Ability of Said Conjugates (1) Synthesis Procedure Different conjugates having an ssH amino linker moiety in which a phosphate group was substituted with a thiophosphate group were synthesized by following the procedure described below. The synthesized compounds are represented by the formulas given below, and shown in Table 4.

(1-1) Synthesis of a CpG DNA(S) Derivative

Synthesis of CpG DNA(S) was performed using the phosphoramidite method (vid., e.g., *Nucleic Acids Research,* 12, 4539 (1984)). Synthesis of amino group-modified CpG DNA(S) was performed using an ssH amino linker (vid., *Bioorg. Med. Chem.,* 16, 941-949 (2008)) in which a phosphate group was substituted with a thiophosphate group. These syntheses were contracted to a contract synthesis service (provided by GeneDesign Inc.).

The nucleotide sequence of the synthesized CpG DNA(S) was the same as that of CpG30a as described above in (1) in Example 1.

The obtained amino group-modified CpG DNA(S) had at its 5' end the structure represented by the formula shown below. Hereinafter, the CpG DNA(S) derivative having at its 5' end the structure represented by the formula shown below and comprising the sequence of SEQ ID NO: 6 is referred to as "CpG30(S)a2".

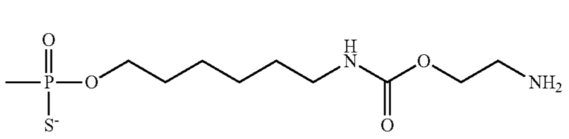 [SMILES: CP(=O)([S-])OCCCCCCNC(=O)OCCN]

Further, 1 mol of amino group-modified CpG DNA(S) was mixed with 30 mol of succinimidyl 6-[3'-(2-pyridyldithio)-propionamido]hexanoate (LC-SPDP) in a phosphate buffer (pH 8.0). After being left to stand at 40° C. for 3 hours, the mixture was purified using a NAP-5 column to yield SPDP-modified CpG DNA(S).

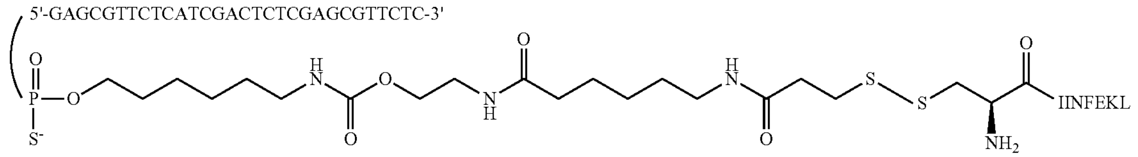

CpG30(S)a2-OVApep8

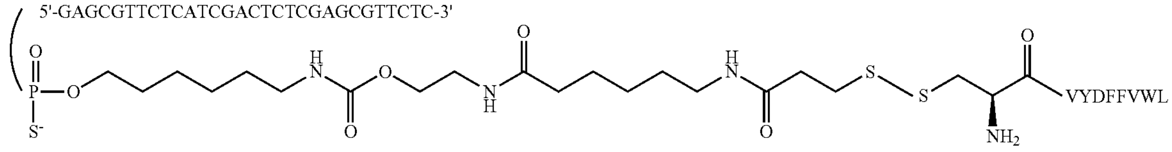

CpG30(S)a2-mTRP2pep9

TABLE 4

| Name | CpG DNA (nucleotide sequence moiety of structure) | peptide (a moiety excl. N-terminal Cys in peptide) | HPLC condition | Retention time (min.) | Molecular formula | Mass spectrometry (ESI) |
|---|---|---|---|---|---|---|
| CpG30(S)a2-OVApep8 | CpG30(S)a2 | C-OVA7 | (E) | 8.0 | $C_{353}H_{476}N_{116}O_{172}P_{30}S_{32}$ | $[M-11H]^{11-}$: Calcd 1003.58465 (most abundant mass), Found 1003.58665 |
| CpG30(S)a2-mTRP2pep9 | CpG30(S)a2 | C-TRP2-8 | (E) | 9.1 | $C_{369}H_{480}N_{116}O_{173}P_{30}S_{32}$ | $[M-11H]^{11-}$: Calcd 1022.86182 (most abundant mass), Found 1022.86031 |

The obtained SPDP-modified CpG DNA(S) had the structure represented by the formula shown below.

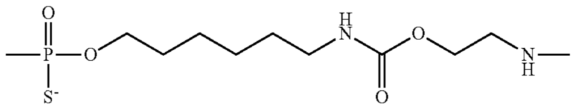

(1-2) Synthesis of N-Terminal Modified Peptides

Synthesis of peptides was contracted to a contract synthesis service (provided by GeneDesign Inc.).

The amino acid sequences of the synthesized peptides are shown below.

```
C-OVA7:
                          (SEQ ID NO: 46)
CIINFEKL

C-TRP2-8:
                          (SEQ ID NO: 32)
CVYDFFVWL
```

C-OVA7 is a peptide modified by adding cysteine to the N-terminus of a peptide consisting of amino acid residues 259 to 265 of ovalbumin (OVA; GenBank accession No. CAA23716.1). Also, C-OVA7 is a peptide modified by deleting one N-terminal residue from the MHC-1-binding peptide, OVA peptide 1 (a peptide consisting of the amino acid sequence of SEQ ID NO: 41) and adding cysteine to the N-terminus.

C-TRP2-8 is, as described in Example 1, a peptide modified by deleting one N-terminal residue from the MHC-1-binding peptide, TRP2-9, and adding cysteine to the N-terminus.

(1-3) Synthesis of CpG DNA(S)-Peptide Conjugates

The SPDP-modified CpG DNA(S) synthesized above in (1-1) was mixed with 5-10 mol equivalent of each of the peptides synthesized above in (1-2) in an aqueous solution of 50% dimethylsulfoxide (DMSO), and the mixtures were reacted at 40° C. for 2 hours. After the reaction, the mixtures were fractionated by HPLC purification under the following condition to afford CpG DNA(S)-peptide conjugates.

<HPLC Condition (E)>

HPLC was performed under the following gradient conditions using 0.1 M hexafluoroisopropanol (HFIP)/8 mM triethylamine (TEA) as solvent A and methanol as solvent B, respectively, and the column XBridge BEH C18 (4.6×75 mm Column XP) (Waters Corporation), at a column temperature of 40° C. and a flow rate of 1 mL/min.

| | |
|---|---|
| 0 min. | A: 80% B: 20% |
| to 10 min. | A: 50% B: 50% |

The HPLC conditions and retention times used for the fractionation of the different conjugates are shown in Table 4.

(2) Test Procedure

By following the same procedure as in Example 2, CpG30(S)a2-OVApep8 and CpG30(S)a2-mTRP2pep9 were evaluated for cytotoxic T lymphocyte-inducing ability. The dose of CpG30(S)a2-OVApep8 administered was 20 ng per mouse in terms of peptide. The dose of CpG30(S)a2-mTRP2pep9 administered was 200 ng per mouse in terms of peptide. The difference in dose between the two conjugates reflects the difference in the strength of antigenicity between their original peptides.

The results are shown in FIGS. 13A-13D. It was shown that both of the conjugates CpG30(S)a2 OVApep8 and CpG30(S)a2-mTRP2pep9 synthesized in (1) had high cytotoxic T lymphocyte-inducing ability.

Example 7: Evaluation of Induction of Cytotoxic T Lymphocytes by a CpG DNA(S)-Peptide Conjugate (Activity in Two-Dose Administration)

The cytotoxic T lymphocyte-inducing ability in administration of CpG30(S)a-mTRP2pep9 at two doses was evaluated by following the same procedure as in Example 2. The second administration was performed after 10 days from the first administration. Both of the two doses were 200 ng per mouse in terms of peptide.

Figure 14A:
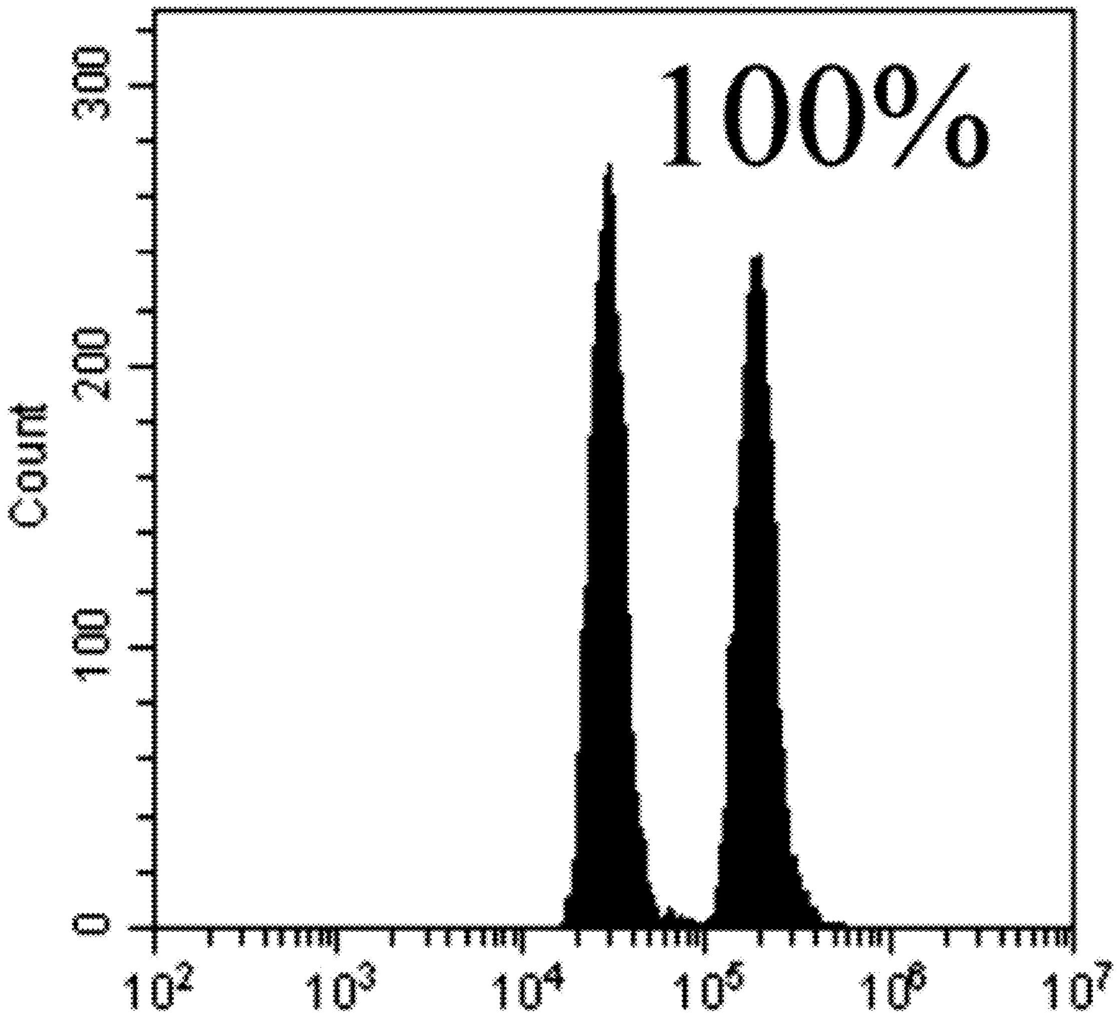
FIGS. 14A-14C depict the results of the flow cytometric analysis performed in Example 7.
Figure 14B:
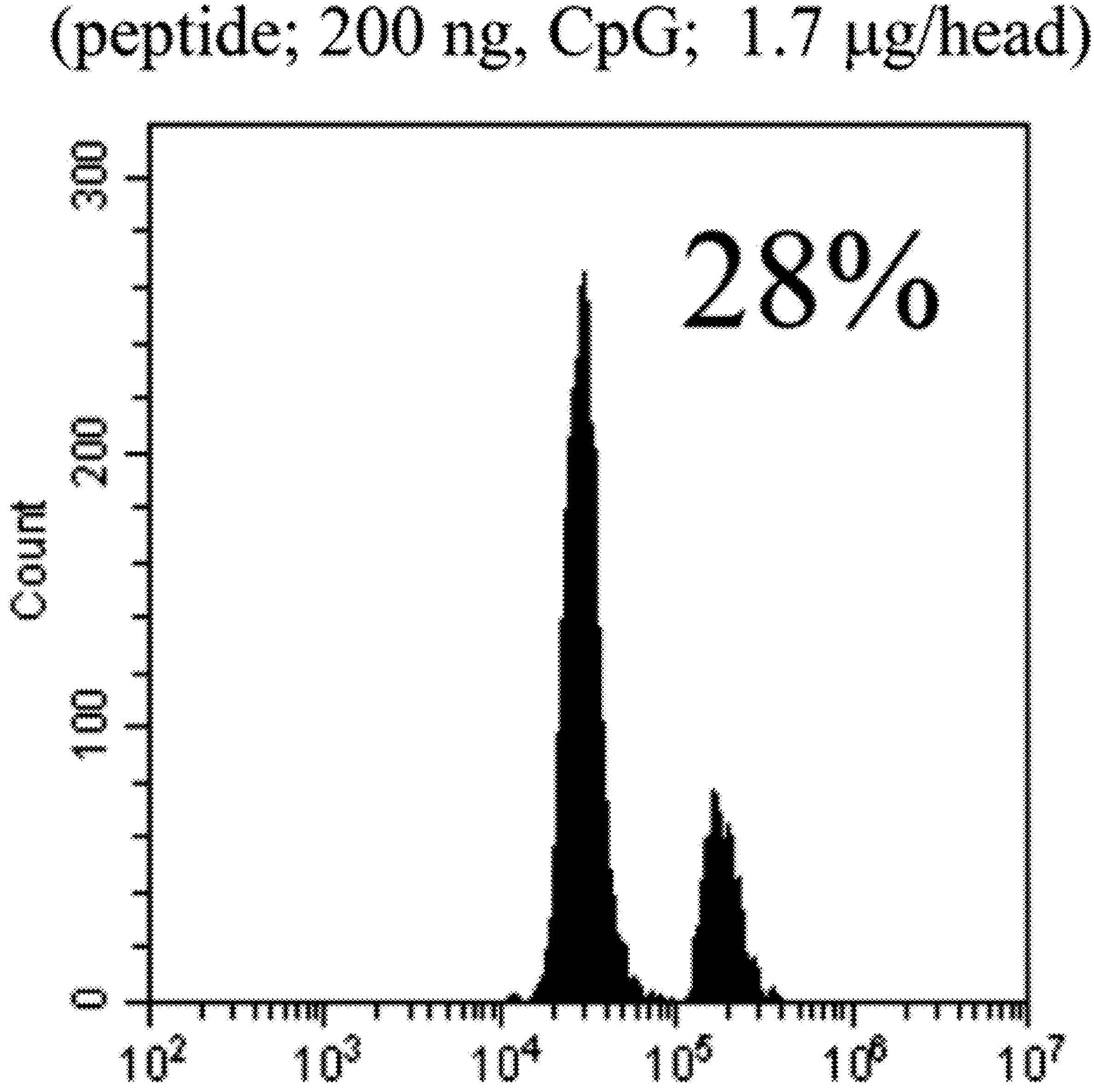
Figure 14C:
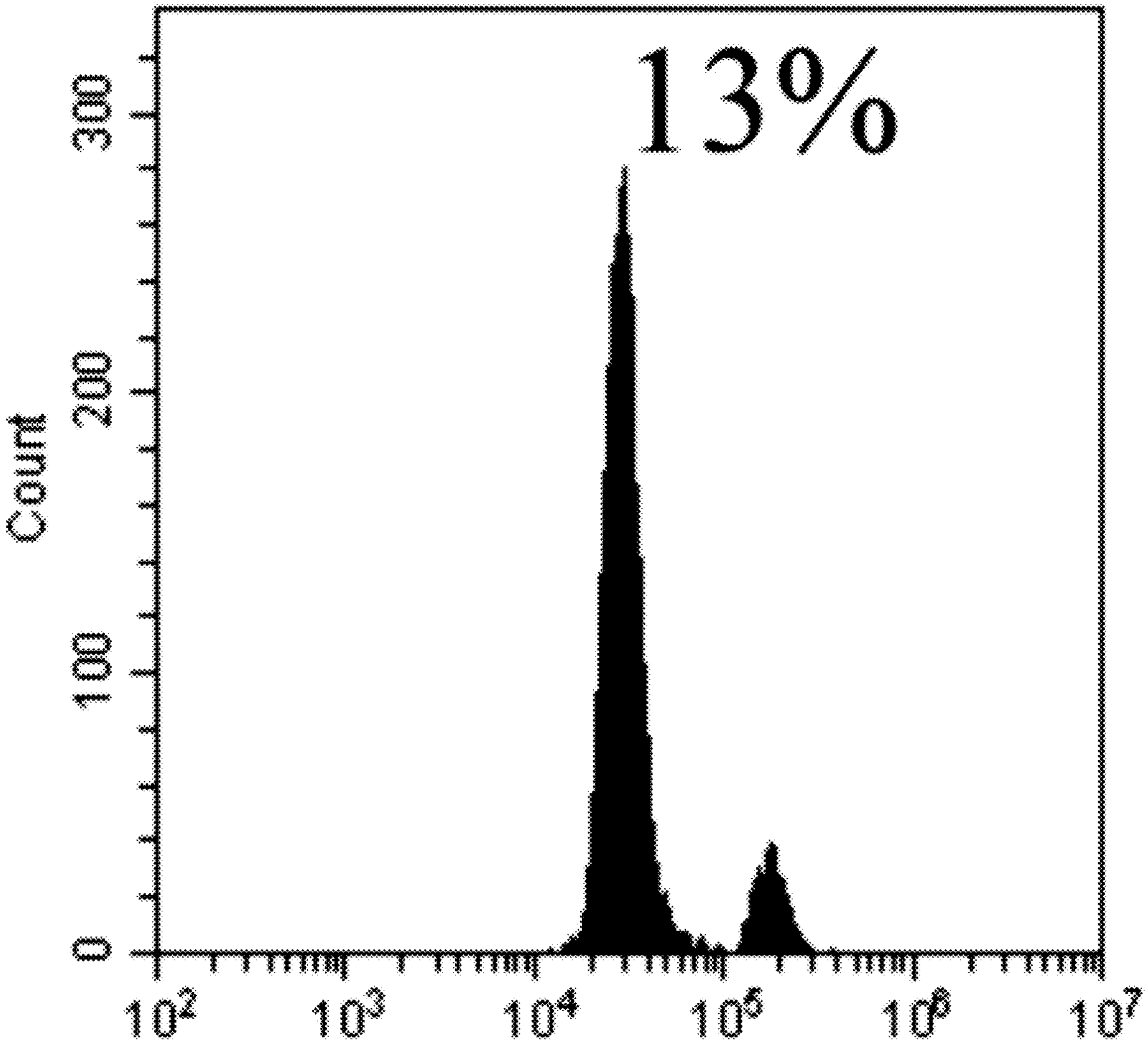

The results are shown in FIGS. 14A-14C. It was suggested that two-dose administration of the CpG DNA(S)-peptide conjugate had enhanced CTL activity as compared to the single-dose administration of the same conjugate.

Example 8: Synthesis of Double-Stranded CpG DNA(S)-Peptide Conjugates

Different double-stranded complexes (double-stranded CpG DNA(S)-peptide conjugates) were prepared by annealing a CpG DNA(S)-peptide conjugate (CpG30(S)a-mTRP2pep9; vid., Example 1) with any of different DNA derivatives having a sequence complementary to the nucleotide sequence of the CpG DNA(S) moiety.

(1) Synthesis of CpG Complementary Strand DNA Derivatives

Like in the synthesis of CpG DNA(S), synthesis of DNA complementary to CpG was performed using the phosphoramidite method. Synthesis of complementary strand DNA lipid-modified at its 5' end was performed by using lipid-modified phosphoramidite as represented by the formula shown below (synthesized by the same procedure as that for M22-12 phosphoramidite as described in the patent literature (WO 2017/057540)) at the last coupling step during the synthesis of the sequence of complementary strand DNA.

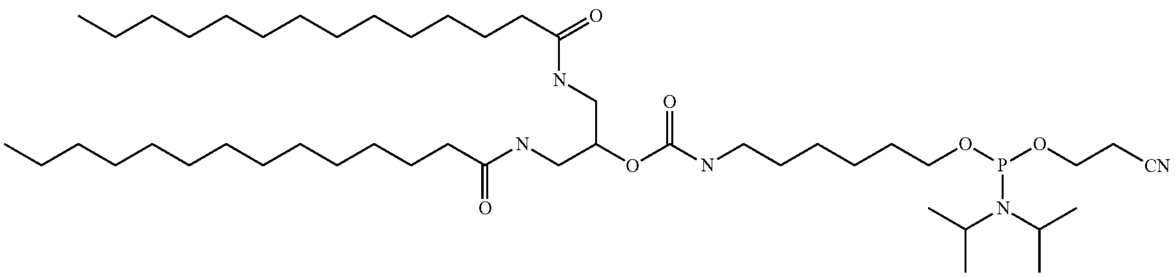 [SMILES: CCCCCCCCCCCCCC(=O)NCC(CNC(=O)CCCCCCCCCCCCC)OC(=O)NCCCCCCOP(OCCC#N)N(C(C)C)C(C)C]

Synthesis of complementary strand DNA lipid-modified at its 3' end was performed by following the procedure described below.

After the first coupling was performed using Asymmetric Doubler (Lev) Phosphoramidite (GlenResearch, 10-1981) on a universal solid-phase support (Glen UnySupport 500 (GlenResearch, 20-5040)), the sequence of complementary strand DNA was synthesized. Then, after detritylation and acetyl protection were performed on the solid-phase support, the levulinic acid unit was deprotected by the procedure specified by the manufacturer. The hydroxyl group produced was allowed to react with the lipid-modified phosphoramidite as mentioned above, whereby the compound of interest was synthesized.

Synthesis of complementary strand DNA lipid-modified at its 3'- and 5' ends was performed by following the procedure described below.

After the first coupling was performed using Asymmetric Doubler (Lev) Phosphoramidite (GlenResearch, 10-1981) on a universal solid-phase support (Glen UnySupport 500 (GlenResearch, 20-5040)), the sequence of complementary strand DNA was synthesized. Then, after detritylation was performed on the solid-phase support, the levulinic acid unit was deprotected by the procedure specified by the manufacturer. The hydroxyl groups produced at the 3' and 5' ends were allowed to react with the lipid-modified phosphoramidite as mentioned above, whereby the compound of interest was synthesized.

The structures of the synthesized DNA derivatives complementary to CpG are shown below. The DNA sequence (compK3: SEQ ID NO: 47) found in the derivatives is a sequence complementary to the nucleotide sequence of K3 (SEQ ID NO: 1).

5'-Lipo-compK3:
5'-Lipo^G^A^G^AACGCTCGAGA^G^T-3'

3'-Lipo-compK3:
5'-G^A^G^AACGCTCGAGA^G^T^Lipo-3'

5',3'-di-Lipo-compK3:
5'-Lipo^G^A^G^AACGCTCGAGA^G^T^Lipo-3'

In the structures shown above, the symbol “^” represents a phosphorothioate bond between nucleosides. “Lipo^G” and “T^Lipo” represent the following structures.

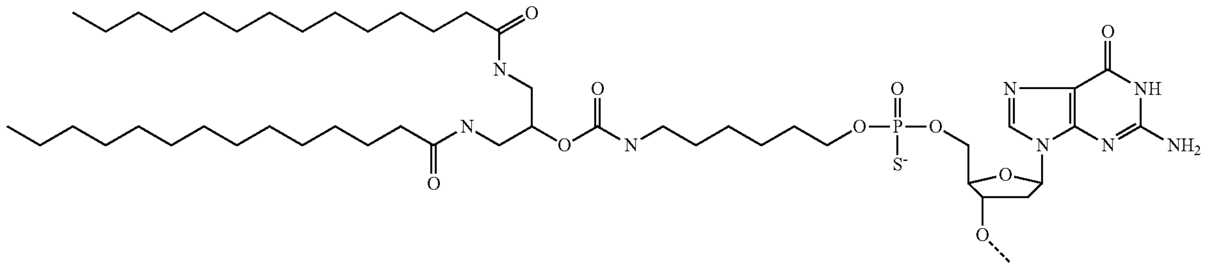

Lipo^G

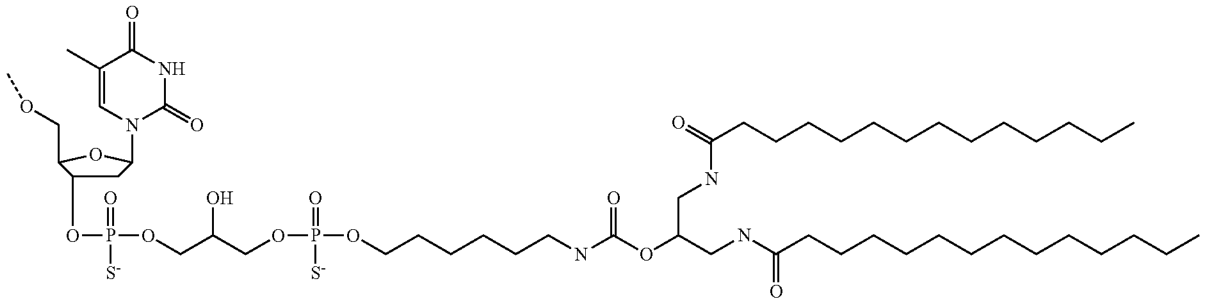

T^Lipo

The DNA derivatives complementary to CpG were fractionated by HPLC under the following condition. The results are shown in Table 5.

<HPLC Condition (F)>

HPLC was performed under the following gradient conditions using 0.1 M hexafluoroisopropanol (HFIP)/8 mM triethylamine (TEA) as solvent A and methanol as solvent B, respectively, and the column Clarity™ 2.6 μm Oligo-MS 100A (LC-Column 50×2.1 mm) (Phenomenex Inc.), at a column temperature of 60° C. and a flow rate of 0.5 mL/min.

| | |
|---|---|
| 0 min. | A: 90% B: 10% |
| to 7 min. | A: 10% B: 90% |

TABLE 5

| Name | CpG DNA | HPLC condition (analysis) | Retention time (min.) | Molecular formula | Mass spectrometry (MALDI-TOF) |
|---|---|---|---|---|---|
| 5'-Lipo-compK3 | compK3 | (F) | 2.95 | $C_{195}H_{269}N_{71}O_{92}P_{16}S_6$ | Calcd 5764.2679, Found 5764.2680 |
| 3'-Lipo-compK3 | compK3 | (F) | 2.99 | $C_{198}H_{276}N_{71}O_{96}P_{17}S_7$ | Calcd 5934.2482, Found 5934.2234 |
| 5',3'-di-Lipo-compK3 | compK3 | (F) | 3.86 | $C_{236}N_{350}N_{74}O_{102}P_{18}S_8$ | Calcd 6665.7518, Found 6665.7147 |

(2) Formation of Double-Stranded Complexes with CpG DNA(S)-Peptide Conjugates

A PBS solution of CpG30(S)a-mTRP2pep9 was mixed with a PBS solution of each of the lipid-modified compK3 DNA derivatives synthesized above in (1) in a 1.5 mL tube to give a final concentration of 3.4 μM. The tubes were warmed by placing them into a hot water bath at 90° C., and then left to stand overnight to allow them to cool slowly back to room temperature (the double strands were formed during this cooling process). Administration of 50 μL of each of the resulting solutions to mice is equivalent to administration of 200 ng of the peptide to mice.

Five different double-stranded complexes consisting of each of the combinations listed below in Table 6 were formed. Formation of a double-stranded complex can be confirmed by a method such as electrophoresis with a polyacrylamide gel, etc., liquid chromatography (e.g., size exclusion chromatography), melt temperature measurement using ultraviolet spectroscopy, or measurement of aggregate molecular weight by static light-scattering measurement.

TABLE 6

| | CpG DNA(S)-peptide conjugate | Complementary stranded DNA derivative |
|---|---|---|
| 1 | CpG30 (S)a-mTRP2pep9 | 5'-Lipo-compK3 |
| 2 | CpG30 (S)a-mTRP2pep9 | 3'-Lipo-compK3 |

TABLE 6-continued

| | CpG DNA(S)-peptide conjugate | Complementary stranded DNA derivative |
|---|---|---|
| 3 | CpG30 (S)a-mTRP2pep9 | 5',3'-di-Lipo-compK3 |
| 4 | CpG20 (S)a-mTRP2pep9 | 5'-Lipo-compK3 |
| 5 | CpG20 (S)a-mTRP2pep9 | 3'-Lipo-compK3 |

Example 9: Synthesis of CpG DNA(S)-Peptide Conjugated Using MHC-2-Binding Peptides, and Evaluation of Activation of CD4$^+$ T Lymphocytes by Said Conjugates (1) Synthesis Procedure Two different conjugates, CpG30(S)a2-OVA2-15 and CpG30(S)a2-OVA2-17, having a CpG DNA(S) moiety derived from an MHC-2-binding peptide, were synthesized by following the procedure described below. The synthesized compounds are represented by the formulas given below, and shown in Table 7.

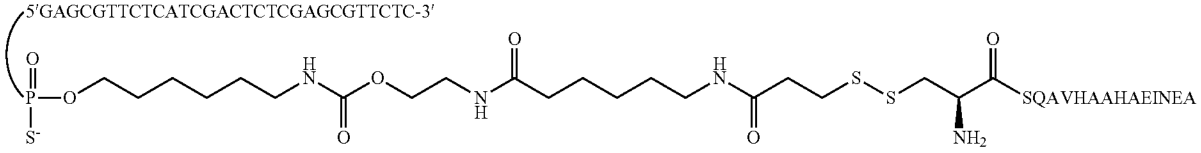

CpG30(S)a2-OVA2-15

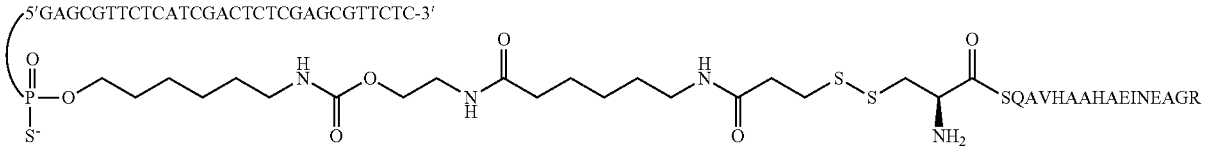

CpG30-(S)a2-OVA2-17

TABLE 7

| Name | CpG DNA (nucleotide sequence moiety of structure) | peptide (a moiety excl. N-terminal or C-terminal Cys in peptide) | HPLC condition | Retention time (min.) | Molecular formula | Mass spectrometry (ESI) |
|---|---|---|---|---|---|---|
| CpG30(S)a2-OVA2-15 | CpG30(S)a | C-OVA2-14 | (E) | 6.7 | $C_{371}H_{501}N_{127}O_{183}P_{30}S_{32}$ | $[M-11H]^{11-}$: Calcd 1055.51157 (most abundant mass), Found 1055.51068 |
| CpG30(S)a2-OVA2-17 | CpG30(S)a2 | C-OVA2-16 | (E) | 7.2 | $C_{379}H_{516}N_{132}O_{185}P_{30}S_{32}$ | $[M-12H]^{12-}$: Calcd 985.22856 (most abundant mass), Found 985.22872 |

(1-1) Synthesis of CpG DNA(S) Derivatives

By following the same procedure as in Example 6, CpG30(S)a2 and a SPDP-modified derivative thereof were synthesized.

(1-2) Synthesis of N-Terminal Modified Peptides

N-terminal cysteine-modified peptides were synthesized by a common Fmoc solid-phase peptide synthesis procedure. The amino acid sequences of the synthesized peptides are shown below.

The amino acid sequences of the synthesized peptides are shown below.

```
C-OVA2-14:
                              (SEQ ID NO: 48)
CSQAVHAAHAEINEA

C-OVA2-16:
                              (SEQ ID NO: 51)
CSQAVHAAHAEINEAGR
```

C-OVA2-14 is a peptide modified by adding cysteine to the N-terminus of a peptide consisting of amino acid residues 325 to 338 of ovalbumin (OVA; GenBank accession No. CAA23716.1). Also, C-OVA2-14 is a peptide modified by deleting one N-terminal residue and two C-terminal residues from OVA peptide 2 (a peptide consisting of the amino acid sequence of SEQ ID NO: 42 comprising a murine I-Ab/I-Ad binding sequence) and adding cysteine to the N-terminus.

C-OVA2-16 is a peptide modified by adding cysteine to the N-terminus of a peptide consisting of amino acid residues 325 to 340 of ovalbumin. Also, C-OVA2-16 is a peptide modified by deleting one N-terminal residue from OVA peptide 2 and adding cysteine to the N-terminus.

(1-3) Synthesis of CpG DNA(S)-Peptide Conjugates

By following the same procedure as described in (1-3) in Example 6, CpG DNA(S)-peptide conjugates were synthesized using SPDP-modified CpG DNA(S) synthesized above in (1-1) and the peptides synthesized above in (1-2).

(2) Test Procedure (Evaluation of $CD4^+$ T Lymphocyte Activation by Single Immunization with CpG-MHC2 Peptide Conjugates in an IFN-γ Secretion Activity Assay)

Each of the CpG DNA(S)-peptide conjugates as an antigen was intracutaneously administered to mice (C57BL/6 mice (♂, 7 weeks old)). The dose of the CpG DNA(S)-peptide conjugates administered was 1000 ng per mouse in terms of peptide. After one week of administration, splenocytes were isolated and seeded in a 96-well dish at $1.0\times10^6$ cells/100 μL (culture medium: RPM11640), and then, an OVA-derived MHC-2-binding antigenic peptide ($OVA_{324-340}$: ISQAVHAAHAEINEAGR (SEQ ID NO: 42)) was added to a concentration of 10 μg/mL. After 24 hours, interferon-γ (IFN-γ) in the culture medium was quantified using the IFN gamma mouse ELISA kit (Invitrogen; IFN gamma 'Femto-HS' High Sensitivity Mouse Uncoated ELISA Kit). In the case where a mouse is immunized by administering a CpG DNA(S)-peptide conjugate, antigen-specific $CD4^+$ T lymphocytes in splenocytes are activated to induce secretion of IFN-γ, upon stimulation by addition of an antigenic peptide to the culture medium.

Figure 15:
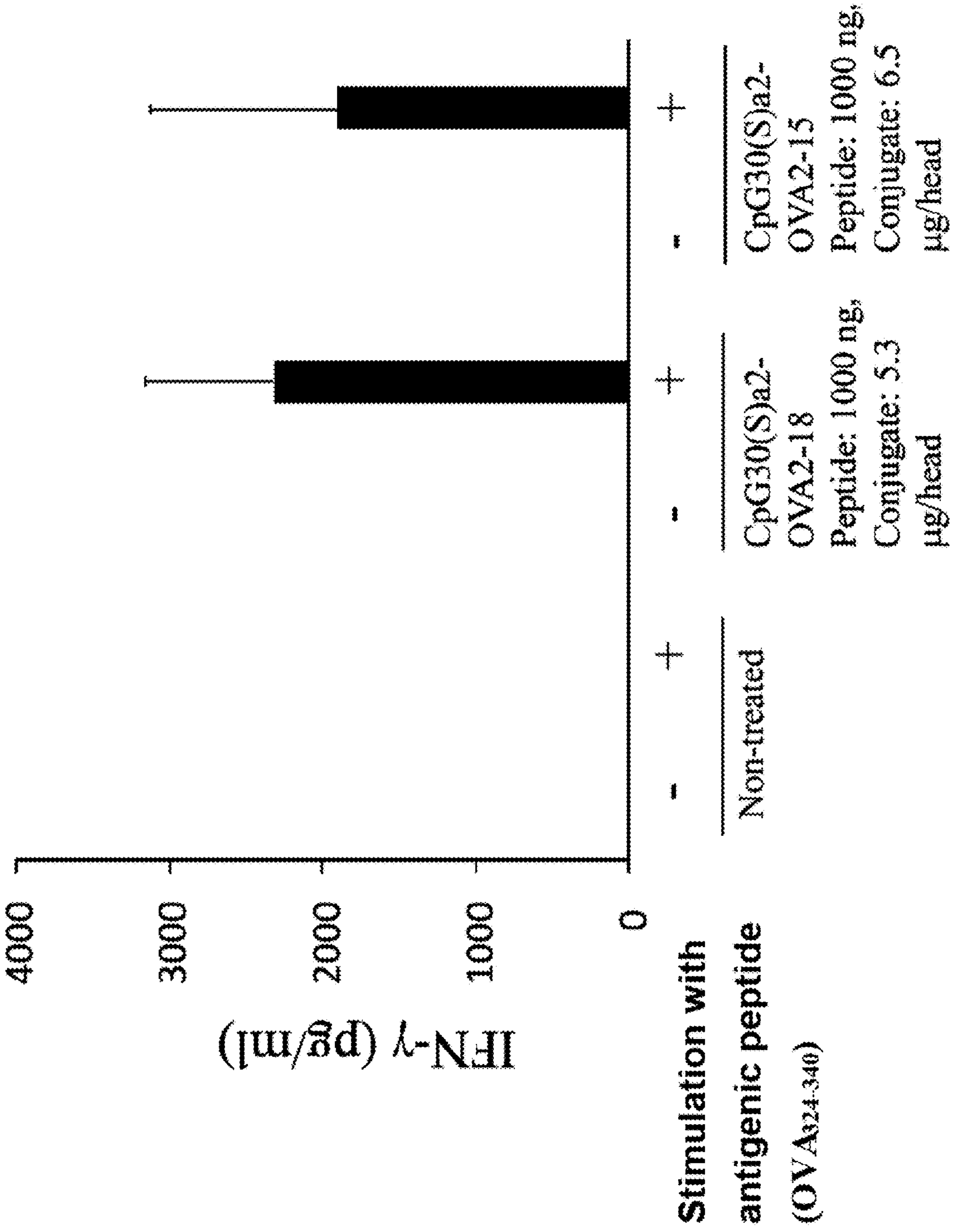
FIG. 15 depicts the results of the measurement of secretion of IFN-γ by $CD4^+$ T cells performed in Example 9 and Reference Example 3.
Figure 17:
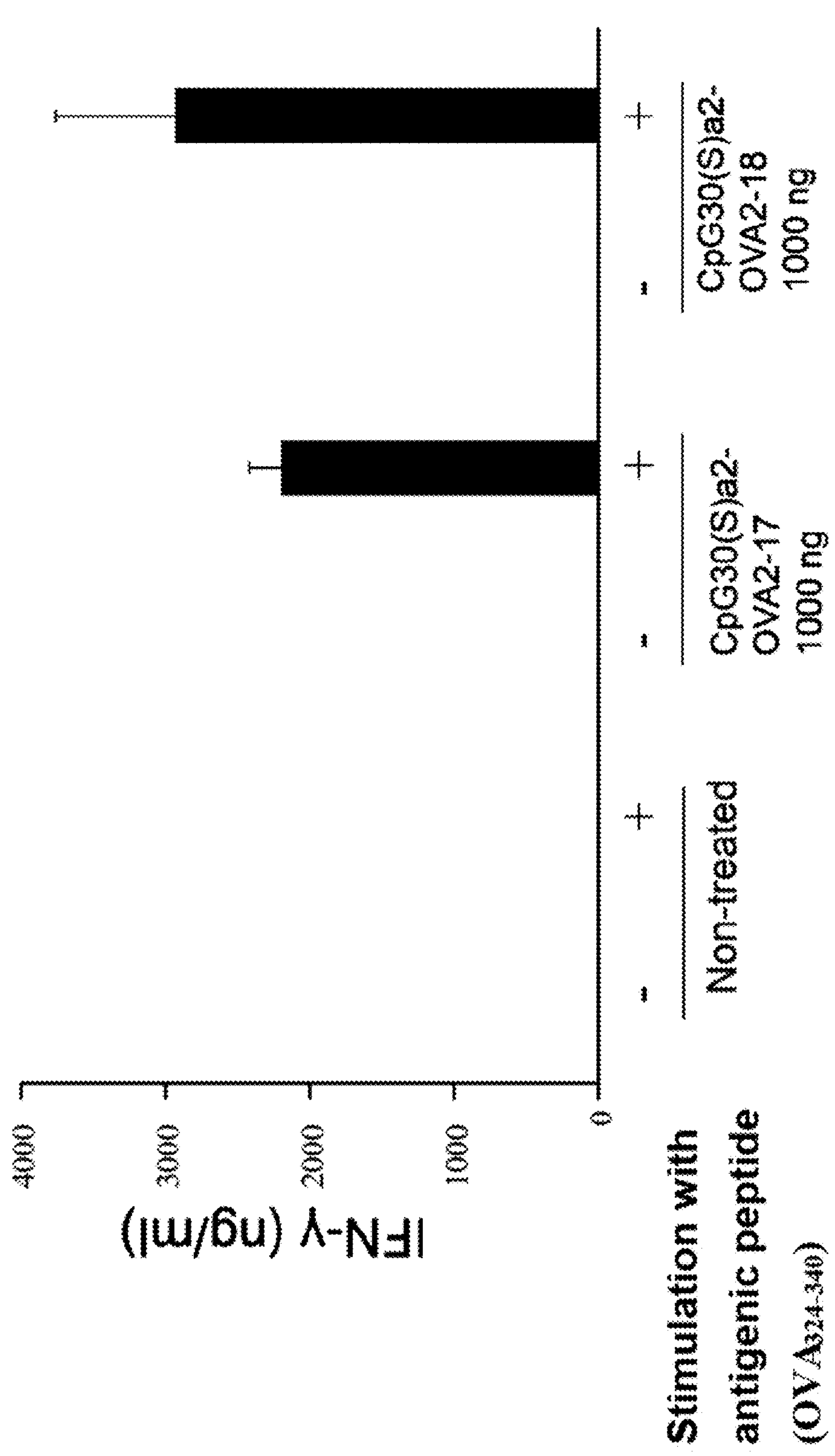
FIG. 17 depicts the results of the measurements of secretion of IFN-γ by $CD4^+$ T cells performed in Example 9 and Reference Example 3.
Figure 18A:
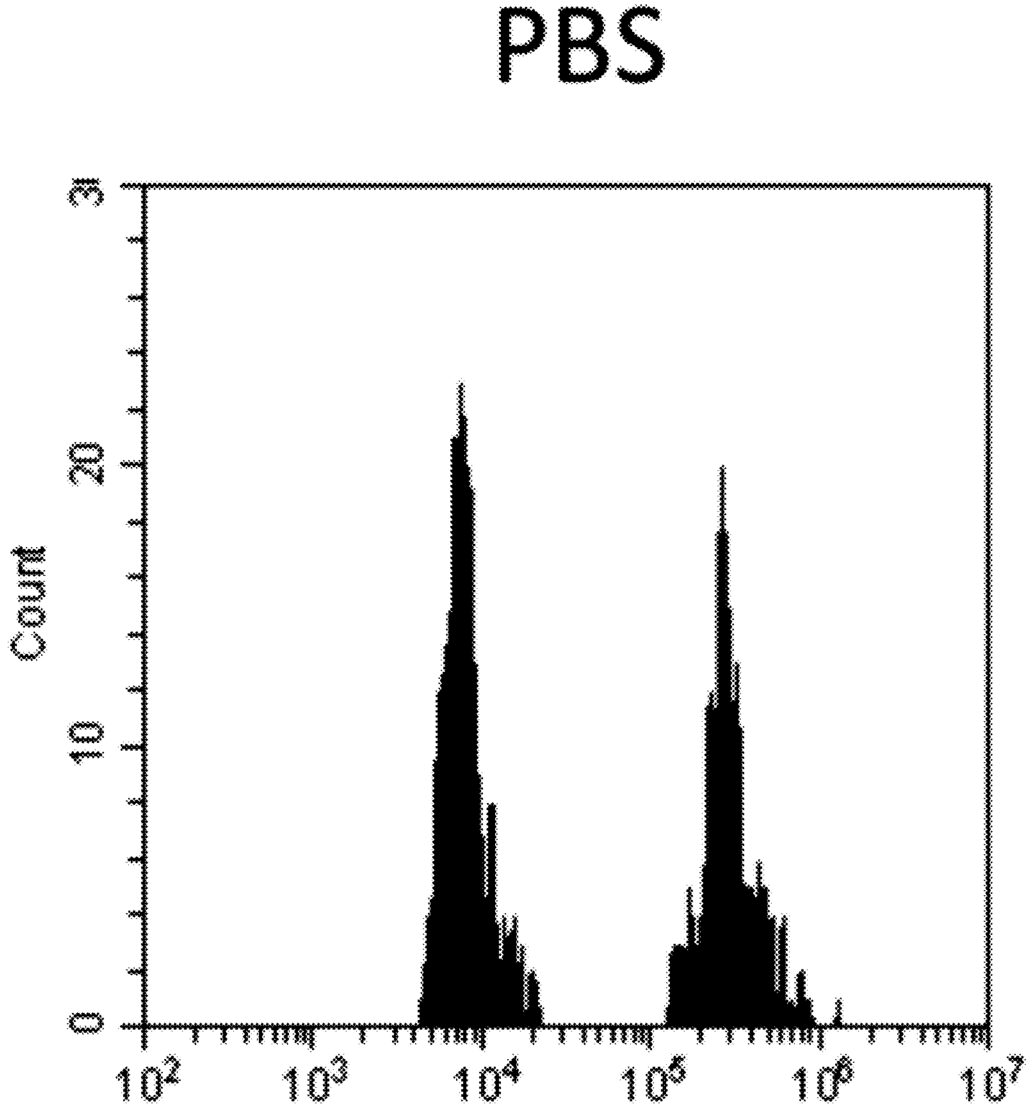
FIGS. 18A-18D depict the results of the flow cytometric analysis performed in Example 10.
Figure 18B:
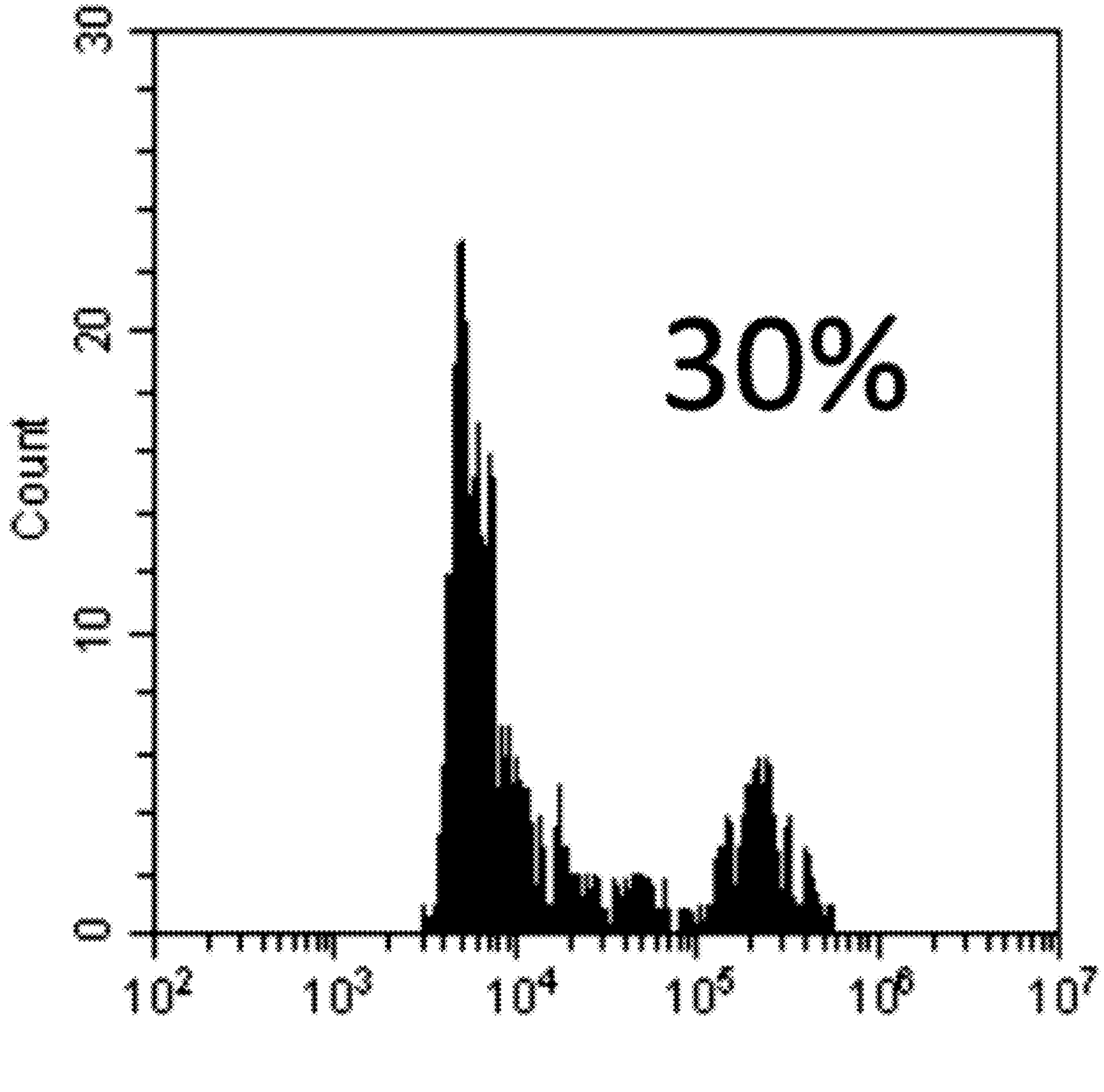
Figure 18C:
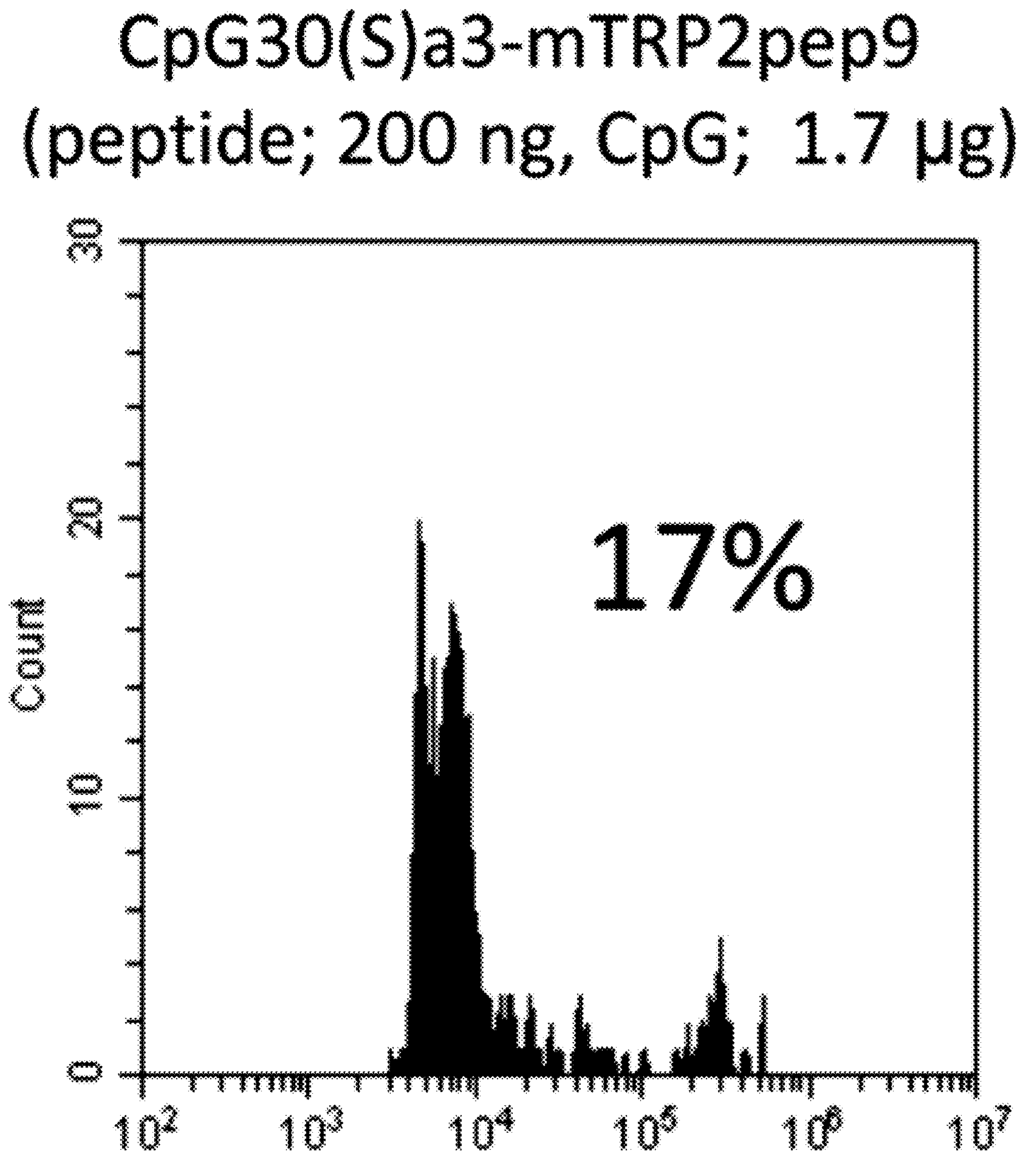
Figure 18D:
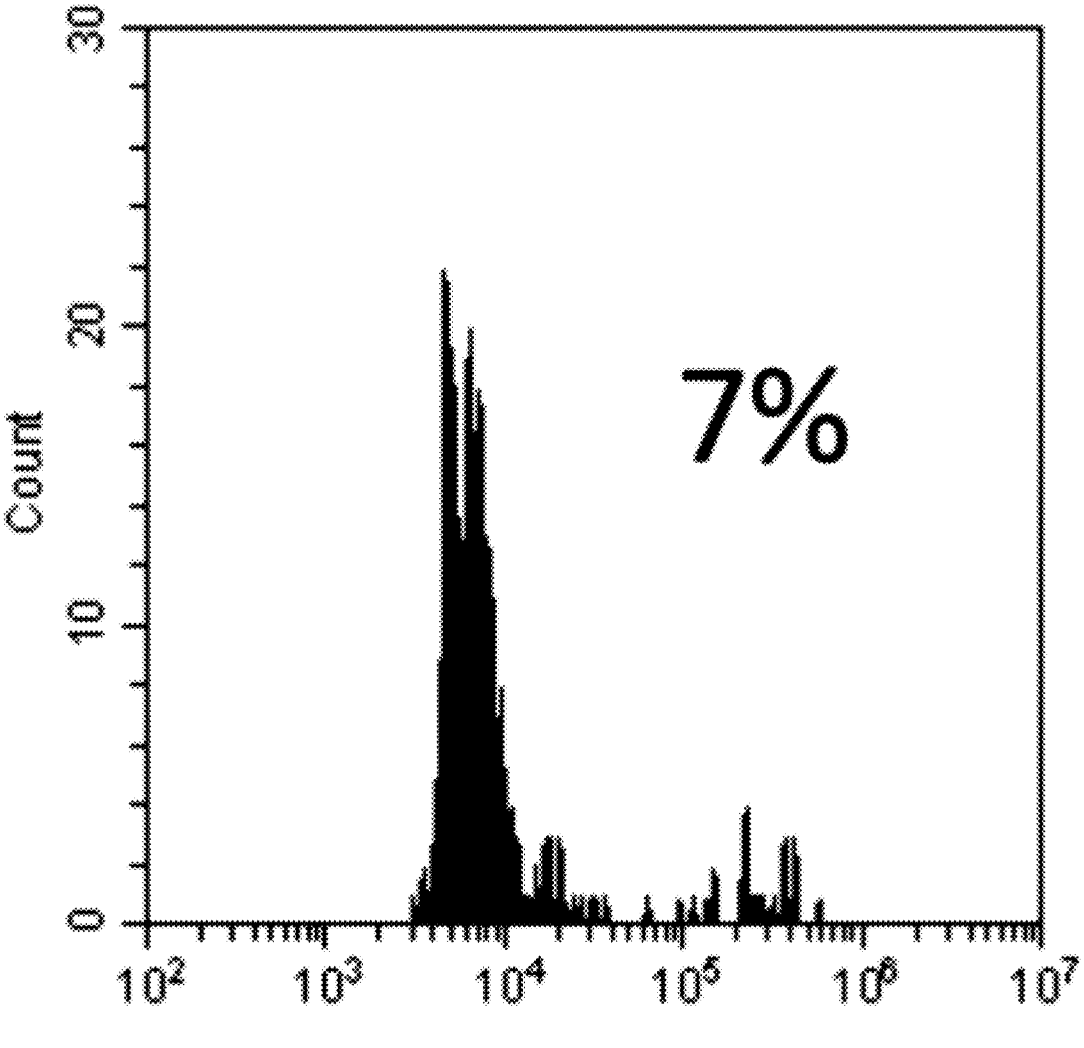

The results are shown in FIGS. 15 and 17.

High IFN-γ secretion activity was observed in splenocytes isolated from both of the mice administered each of CpG30(S)a2-OVA2-15 and CpG30(S)a2-OVA2-17 (FIGS. 15 and 17; refers to Reference Example 3 with regard to CpG30(S)a2-OVA2-18). It was shown that in the preparation of a conjugate using an MHC-2-binding peptide, a C-terminal peptide may be deleted.

Reference Example 3: Synthesis of CpG DNA(S)-Peptide Conjugates Using MHC-2-Binding Peptides, and Evaluation of Activation of CD4+T Lymphocytes by Said Conjugates (1) Synthesis Procedure Two different conjugates, CpG30(S)a2-OVA2-18 and CpG30(S)a2-OVA2-18c, having a CpG DNA(S) moiety derived from an MHC-2-binding peptide, were synthesized by following the procedure described below. The synthesized compounds are represented by the formulas given below, and shown in Table 8.

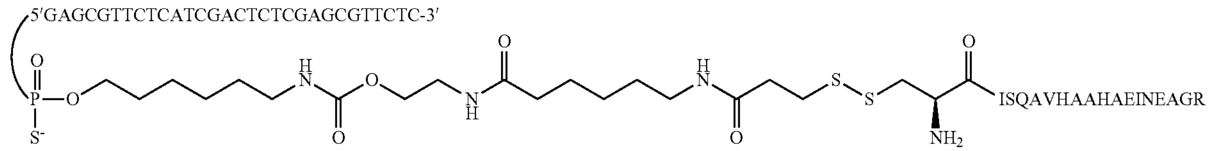

CpG30-(S)a2-OVA2-18

-continued

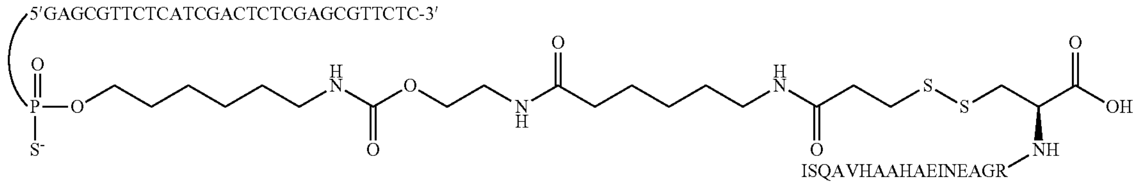

CpG30(S)a2-OVA28-18c

TABLE 8

| Name | CpG DNA (nucleotide sequence moiety of structure) | peptide (a moiety excl. N-terminal or C-terminal Cys in peptide) | HPLC condition | Retention time (min.) | Molecular formula | Mass spectrometry (ESI) |
|---|---|---|---|---|---|---|
| CpG30(S)a2-OVA2-18 | CpG30(S)a | C-OVA2-17 | (E) | 8.2 | $C_{385}H_{527}N_{133}O_{186}P_{30}S_{32}$ | $[M-12H]^{12-}$: Calcd 994.73570 (most abundant mass), Found 994.73459 |
| CpG30(S)a2-OVA2-18c | CpG30(S)a | OVA2-17-C | (E) | 7.6 | $C_{385}H_{527}N_{133}O_{186}P_{30}S_{32}$ | $[M-12H]^{14-}$: Calcd 852.48663 (most abundant mass), Found 852.48585 |

(1-1) Synthesis of CpG DNA(S) Derivatives

By following the same procedure as in Example 6, CpG30(S)a2 and a SPDP-modified derivative thereof were synthesized.

(1-2) Synthesis of a N-Terminal Modified Peptide and a C-Terminal Modified Peptide A N-terminal cysteine-modified peptide and a C-terminal cysteine-modified peptide were synthesized by a common Fmoc solid-phase peptide synthesis procedure.

The amino acid sequences of the synthesized peptides are shown below.

```
C-OVA2-17:
                                    (SEQ ID NO: 49)
CISQAVHAAHAEINEAGR

OVA2-17-C:
                                    (SEQ ID NO: 50)
ISQAVHAAHAEINEAGRC
```

C-OVA2-17 is a peptide modified by adding cysteine to the N-terminus of a peptide consisting of amino acid residues 324 to 340 of ovalbumin. Also, C-OVA2-17 is a peptide modified by adding cysteine to the N-terminus of OVA peptide 2.

OVA2-17-C is a peptide modified by adding cysteine to the C-terminus of a peptide consisting of amino acid residues 324 to 340 of ovalbumin. Also, C-OVA2-17-C is a peptide modified by adding cysteine to the C-terminus of OVA peptide 2.

(1-3) Synthesis of CpG DNA(S)-Peptide Conjugates

By following the same procedure as described in (1-3) in Example 6, CpG DNA(S)-peptide conjugates were synthesized using SPDP-modified CpG DNA(S) synthesized above in (1-1) and the peptides synthesized above in (1-2).

(2) Test Procedure (Evaluation of $CD4^+$ T Lymphocyte Activation by Single Immunization with CpG-MHC2 Peptide Conjugates in an IFN-γ Secretion Activity Assay)

Each of the CpG DNA(S)-peptide conjugates as an antigen was intracutaneously administered to mice (C57BL/6 mice (♂, 7 weeks old)). The dose of the CpG DNA(S)-peptide conjugates administered was 1000 ng per mouse in terms of peptide. After one week of administration, splenocytes were isolated and seeded in a 96-well dish at $1.0\times10^6$ cells/100 μL (culture medium: RPMI1640), and then, an OVA-derived antigenic peptide ($OVA_{324-340}$: ISQAVHAAHAEINEAGR (SEQ ID NO: 42)) was added to a concentration of 10 μg/mL. After 24 hours, interferon-γ (IFN-γ) in the culture medium was quantified using the IFN gamma mouse ELISA kit (Invitrogen; IFN gamma 'Femto-HS' High Sensitivity Mouse Uncoated ELISA Kit). In the case where a mouse is immunized by administering a CpG DNA(S)-peptide conjugate, antigen-specific $CD4^+$ T lymphocytes in splenocytes are activated to induce secretion of IFN-γ, upon stimulation by addition of an antigenic peptide to a culture medium.

Figure 16:
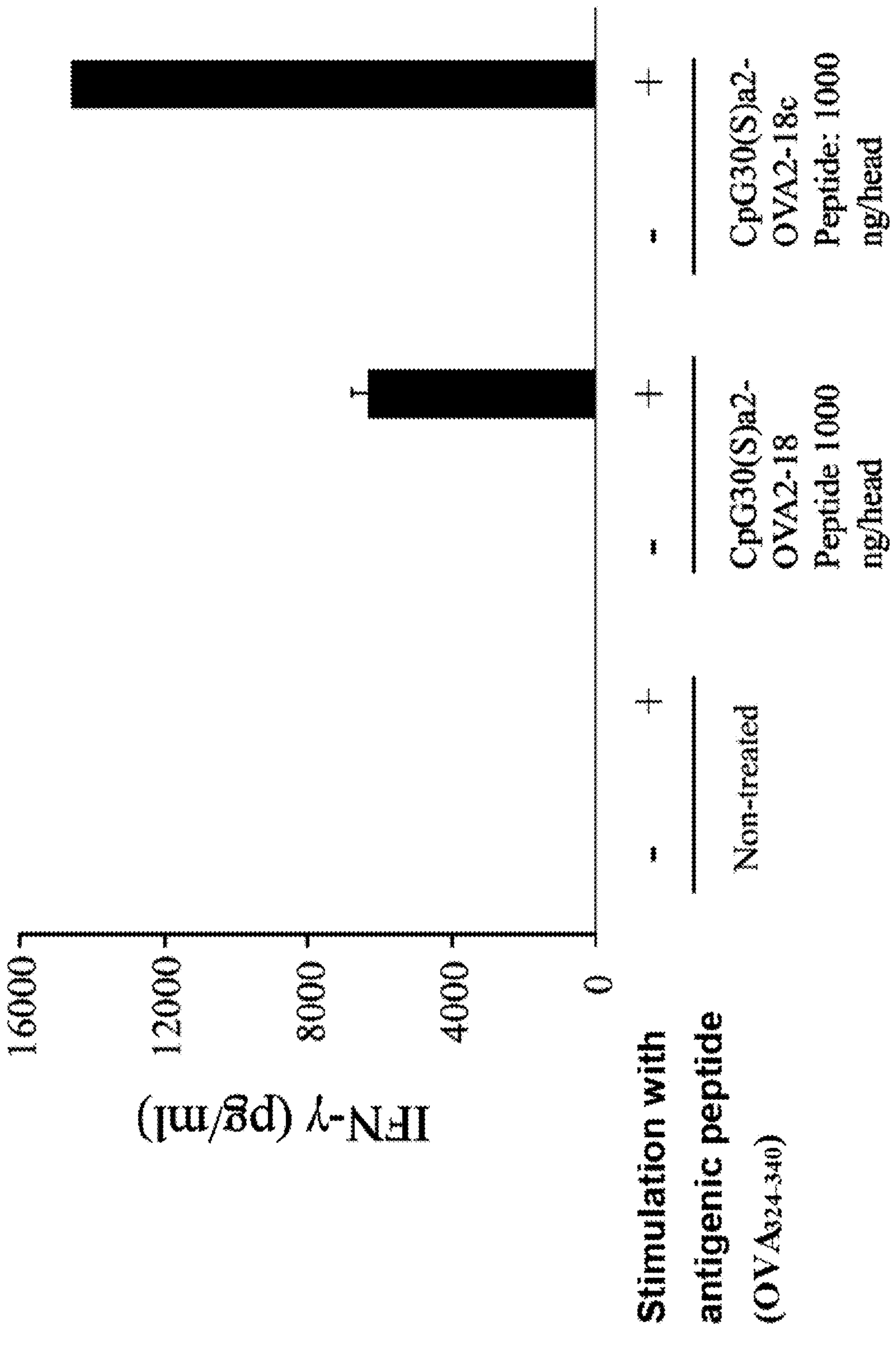
FIG. 16 depicts the results of the flow cytometric analysis performed in Reference Example 3.

The results are shown in FIGS. 15 and 16.

High IFN-γ secretion activity was observed in splenocytes isolated from the mice administered CpG30(S)a2-OVA2-18 (FIGS. 15 and 16).

Also, comparable or higher IFN-γ secretion activity, as compared to that observed after administration of CpG30 (S)a2-OVA2-18, was observed in splenocytes isolated from the mice administered CpG30(S)a2-OVA2-18c (FIG. 16). It was shown that in the preparation of a conjugate using an MHC-2-binding peptide, CpG DNA(S) may be conjugated to the C-terminus.

Example 10: Preparation of CpG DNA(S)-Peptide Conjugates (2), and Evaluation of the Cytotoxic T Lymphocyte-Inducing Ability of Said Conjugates (1) Synthesis Procedure (1-1) Synthesis of CpG DNA(S) Derivatives Synthesis of CpG DNA(S) having a 6-mercaptohexyl group at its 5' end was performed by synthesizing the sequence of CpG DNA(S) using the phosphoramidite method and reacting CpG DNA(S) with 5'-Thiol-Modifier C6 (S-trityl-6-mercaptohexyl-1-[(2-cyanoethyl)-(N,N-diisopropyl)]-phosphoramidite). This synthesis was contracted to a contract synthesis service (provided by GeneDesign Inc.).

The obtained 6-mercaptohexyl-modified CpG DNA(S) had at its 5' end the structure represented by the formula shown below. Hereinafter, the CpG DNA(S) derivative having at its 5' end the structure represented by the formula shown below and comprising the sequence of SEQ ID NO: 6 is referred to as "CpG30(S)a3".

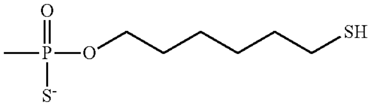

Also, synthesis of a CpG DNA(S) derivative having at its 5' end the structure represented by the formula shown below was performed by reacting amino group-modified CpG DNA(S) synthesized in (1-1) in Example 6 with PPC-NHS ester (2,5-dioxopyrrolidin-1-yl 3-(pyridin-2-yldisulfanyl) butanoate) at a molar ratio of 1:30 in a phosphate buffer (pH 8.0) at 40° C. for 3 hours and purifying the reaction mixture using a NAP-5 column.

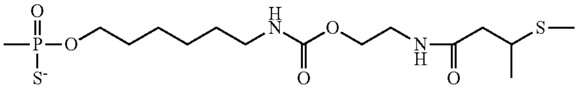

(1-2) Synthesis of an N-Terminal Modified Peptide

C-TRP2-8: CVYDFFVWL (SEQ ID NO: 32) was synthesized by following the same procedure as in Example 1.

(1-3) Synthesis of CpG DNA(S)-Peptide Conjugates

CpG30(S)a3 synthesized above in (1-1) was mixed with 30 mol equivalent of Npys-OMe (CAS: 68118-08-1) in an aqueous solution of 33% dimethylsulfoxide (DMSO), and the mixture was reacted overnight. Then, the mixture was mixed with 5 mol equivalent of the peptide synthesized above in (1-2) in an aqueous solution of 50% dimethylsulfoxide (DMSO), and the mixture was reacted at 40° C. for 2 hours. After the reaction, the mixture was fractionated by HPLC purification to afford CpG DNA(S)-peptide conjugate, CpG30(S)a3-mTRP2pep9.

Also, PPC-NHS ester-modified CpG DNA(S) synthesized above in (1-1) was mixed with 5 mol equivalent of the peptide synthesized above in (1-2) in an aqueous solution of 50% dimethylsulfoxide (DMSO), and the mixture was reacted at 40° C. for 2 hours. After the reaction, the mixture was fractionated by HPLC purification to afford CpG DNA (S)-peptide conjugate, CpG30(S)a2-MeS-mTRP2pep9.

The synthesized compounds are represented by the formulas given below, and shown in Table 9.

5'-GAGCGTTCTCATCGACTCTCGAGCGTTCTC-3'

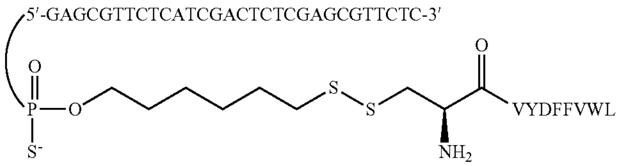

CpG30 (S) a3-mTRP2pep9

5'-GAGCGTTCTCATCGACTCTCGAGCGTTCTC-3'

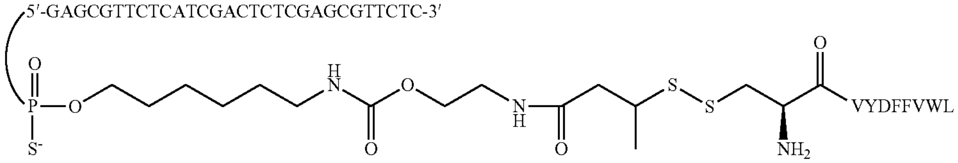

CpG30 (S) a2-MeS-mTRP2pep9

TABLE 9

| Name | CpG DNA (nucleotide sequence moiety of structure) | peptide (a moiety excl. N-terminal Cys in peptide) | HPLC condition | Retention time (min.) | Molecular formula | Mass spectrometry (ESI) |
|---|---|---|---|---|---|---|
| CpG30(S)a3-mTRP2pep9 | CpG30(S)a2 | C-TRP2-8 | (E) | 9.2 | $C_{357}H_{159}N_{113}O_{169}P_{30}S_{32}$ | $[M-10H]^{10-}$: Calcd 1098.13337 (most abundant mass), Found 1098.13178 |
| CpG30(S)a2-MeS-mTRP2pep9 | CpG30(S)a2 | C-TRP2-8 | (E) | 9.1 | $C_{361}H_{171}N_{115}O_{172}P_{30}S_{32}$ | $[M-10H]^{10-}$: Calcd 1115.34187 (most abundant mass), Found 1115.34148 |

(2) Test Procedure

CpG30(S)a3-mTRP2pep9 was evaluated for cytotoxic T lymphocyte-inducing ability by following the same procedure as in Example 2. The dose of CpG30(S)a3-mTRP2pep9 administered was 200 ng per mouse in terms of peptide. As a control, CpG30(S)a2-mTRP2pep9 (a conjugate containing K3-derived CpG motifs; vid., Example 6) was used.

The results are shown in FIGS. 18A-18D. It was shown that like CpG30(S)a2-mTRP2pep9 having a different spacer structure, CpG30(S)a3-mTRP2pep9 had cytotoxic T lymphocyte-inducing ability.

Example 11: Synthesis of CpG DNA(S)-Peptide Conjugates Containing a Cysteine Analogue (1) Synthesis Procedure By following the same procedure as in Example 1, CpG DNA(S)-peptide conjugates were synthesized using peptides modified at the N-terminus using not cysteine but each of different cysteine analogues. The synthesized compounds are represented by the formulas given below, and shown in Table 10. The N-terminal modified peptides used were the following synthetic peptides modified at the N-terminus with each of different non-natural amino acids.

```
dC-mTRP2pep8:
                                    (SEQ ID NO: 52)
D-cysteine-VYDFFVWL

homoC-mTRP2pep8:
                                    (SEQ ID NO: 53)
L-homocysteine-VYDFFVWL

Pen-mTRP2pep8:
                                    (SEQ ID NO: 54)
L-penicillamine-VYDFFVWL
```

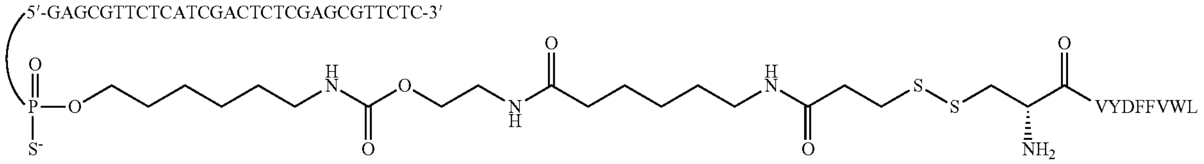

CpG30 (S) a2-dC-mTRP2pep8

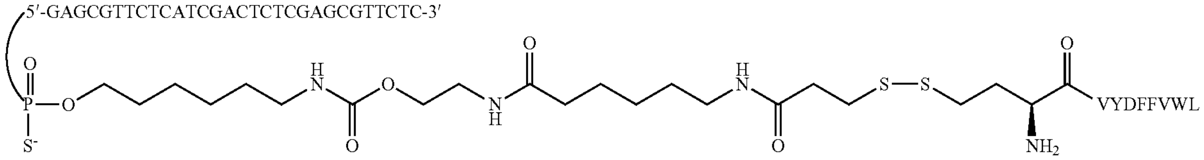

CpG30 (S) a2-homoC-mTRP2pep8

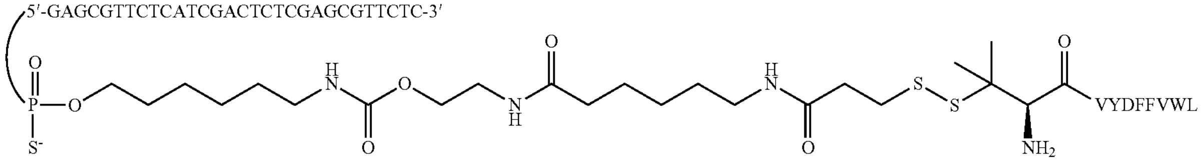

CpG30 (S) a2-dC-mTRP2pep8

TABLE 10

| Name | CpG DNA (nucleotide sequence moiety of structure) | peptide (a moiety excl. N-terminal Cys analogue in peptide) | HPLC condition | Retention time (min.) | Molecular formula | Mass spectrometry (ESI) |
|---|---|---|---|---|---|---|
| CpG30(S)a2-dC-mTRP2pep8 | CpG30(S)a2 | dC-mTRP2pep8 | (E) | 9.5 | $C_{369}H_{480}N_{116}O_{173}P_{30}S_{32}$ | $[M - 11H]^{11-}$: Calcd 1022.86182 (most abundant mass), Found 1022.86122 |
| CpG30(S)a2-homoC-mTRP2pep8 | CpG30(S)a2 | homoC-mTRP2pep8 | (E) | 9.1 | $C_{370}H_{482}N_{116}O_{173}P_{30}S_{32}$ | $[M - 11H]^{11-}$: Calcd 1024.13597 (most abundant mass), Found 1024.13461 |
| CpG30(S)a2-Pen-mTRP2pep8 | CpG30(S)a2 | Pen-mTRP2pep8 | (E) | 9.5 | $C_{371}H_{484}N_{116}O_{173}P_{30}S_{32}$ | $[M - 10H]^{10-}$: Calcd 1128.05186 (most abundant mass), Found 1128.05021 |

(2) Test Procedure

By following the same procedure as in Example 2, CpG30(S)a2-Pen-mTRP2pep8 was evaluated for cytotoxic T lymphocyte-inducing ability. The dose of CpG30(S)a2-Pen-mTRP2pep8 administered was 200 ng per mouse in terms of peptide. As a control, CpG30(S)a2-mTRP2pep9 (a conjugate containing K3-derived CpG motifs; vid., Example 6) was used.

The results are shown in FIGS. 18A-18D. It was shown that like CpG30(S)a2-mTRP2pep9, CpG30(S)a2-Pen-mTRP2pep8 which contained a cysteine analogue had cytotoxic T lymphocyte-inducing ability.

Example 12: Synthesis of a CpG DNA(S)-Peptide Conjugate Having Peptides at Both 5' and 3' Ends of CpG DNA (1) Synthesis Procedure By following the procedures described below in (1-1) to (1-3), a CpG DNA(S)-peptide conjugate having peptides at both ends of CpG DNA was synthesized. The synthesized compound is represented by the formula given below, and shown in Table 11. The N-terminal modified peptide used was C-TRP2-8 (vid., (2) in Example 1).

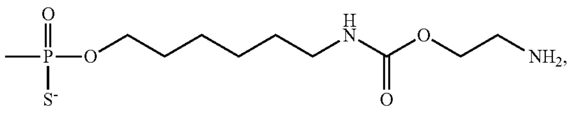 [SMILES: CP(=O)([S-])OCCCCCCNC(=O)OCCN]

and had the structure represented by the following formula at its 3' end:

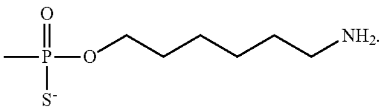

Hereinafter, the CpG DNA(S) derivative having the structures represented by the formulas shown above at its 3' and 5' ends and having the sequence of SEQ ID NO: 6 is referred to as "CpG30(S)a4".

Further, CpG30(S)a4 and succinimidyl 6-[3'-(2-pyridyldithio)-propionamido]hexanoate (LC-SPDP) were mixed at a molar ratio of 1:30 in a phosphate buffer (pH 8.0). After

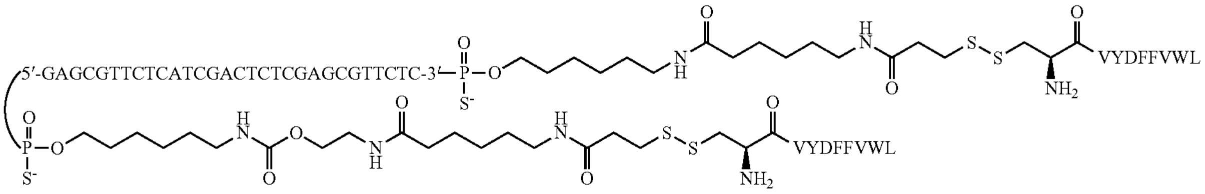

K3CpG30 (S) a4-bis (mTRP2pep9)

TABLE 11

| Name | CpG DNA (nucleotide sequence moiety of structure) | peptide (a moiety excl. N-terminal or C-terminal Cys in peptide) | HPLC condition | Retention time (min.) | Molecular formula | Mass spectrometry (ES1) |
|---|---|---|---|---|---|---|
| K3CpG30(S)a4-bis(SS-mTRP2pep9) | CpG30(S)a4 | C-TRP2-8 | (E) | 11.6 | $C_{445}H_{585}N_{128}O_{190}P_{31}S_{35}$ | $[M - 11H]^{11-}$: Calcd 1167.01309 (most abundant mass), Found 1167.01147 |

(1-1) Synthesis of a CpG DNA(S) Derivative

Synthesis of CpG DNA(S) having amino linkers attached to both 5' and 3' ends thereof was performed by synthesizing a CpG sequence by the phosphoramidite method using 3'-Amino-Modifier C6-dC CPG (Link Technologies Ltd.) and then reacting an ssH amino linker to the 5' end. This synthesis was contracted to a contract synthesis service (provided by GeneDesign Inc.).

The nucleotide sequence of the synthesized CpG DNA(S) was the same as that of CpG30a as described in (1) in Example 1.

The obtained amino group-modified CpG DNA(S) had the structure represented by the following formula at its 5' end:

being left to stand at 40° C. for 3 hours, the mixture was purified using a NAP-5 column to yield SPDP-modified CpG DNA(S)a4.

(1-2) Synthesis of an N-Terminal Modified Peptide

C-TRP2-8: CVYDFFVWL (SEQ ID NO: 32) was synthesized by following the same procedure as in Example 1.

(1-3) Synthesis of a CpG DNA(S)-Peptide Conjugate

SPDP-modified CpG DNA(S)a4 synthesized above in (1-1) was mixed with 5-10 mol equivalent of the peptide synthesized above in (1-2) in an aqueous solution of 50% dimethylsulfoxide (DMSO), and the mixture was reacted at 40° C. for 2 hours. After the reaction, the mixture was fractionated by HPLC purification to afford a CpG DNA (S)-peptide conjugate. The HPLC condition and retention time used for the fractionation are shown in Table 11.

INDUSTRIAL APPLICABILITY

According to the present invention, there can be provided immunity-inducing agents capable of inducing CTL activity, which can be prepared with a wide variety of antigenic peptides, and pharmaceutical compositions comprising said agents.

Sequence Listing Free Text

SEQ ID NO: 1: K3
SEQ ID NO: 2: K3-20(b)
SEQ ID NO: 3: K3-21
SEQ ID NO: 4: K3-24
SEQ ID NO: 5: K3-27
SEQ ID NO: 6: K3-30(a)
SEQ ID NO: 7: K3-30(b)
SEQ ID NO: 8: K3-40
SEQ ID NO: 9: K3-30(c)
SEQ ID NO: 10: K3-30(d)
SEQ ID NO: 11: K3-30(e)
SEQ ID NO: 12: K3-30(f)
SEQ ID NO: 13: K3-26(a)
SEQ ID NO: 14: K3-26(b)
SEQ ID NO: 15: ODN1668
SEQ ID NO: 16: ODN1668-30
SEQ ID NO: 17: ODN1668-40
SEQ ID NO: 18: ODN1826
SEQ ID NO: 19: ODN1826-30
SEQ ID NO: 20: ODN1826-40
SEQ ID NO: 21: ODN2006
SEQ ID NO: 22: ODN2006-30
SEQ ID NO: 23: ODN2006-40
SEQ ID NO: 24: ODN684
SEQ ID NO: 25: ODN684-30
SEQ ID NO: 26: ODN684-40
SEQ ID NO: 27: ODN D-SL01
SEQ ID NO: 28: ODN D-SL01-35
SEQ ID NO: 29: C-CpG #1
SEQ ID NO: 30: C-OVA8
SEQ ID NO: 31: C-TRP2-9
SEQ ID NO: 32: C-TRP2-8
SEQ ID NO: 33: C-gp100-9
SEQ ID NO: 34: C-gp100-8
SEQ ID NO: 35: CM-TRP2-9
SEQ ID NO: 36: C-TRP2-13
SEQ ID NO: 37: C-TRP2-11
SEQ ID NO: 38: C-OVA2-17
SEQ ID NO: 39: C-OVA2-14
SEQ ID NO: 40: C-OVA2-11
SEQ ID NO: 41: OVA peptide 1
SEQ ID NO: 42: OVA peptide 2
SEQ ID NO: 43: 1018ISS
SEQ ID NO: 44: 1018ISS #30
SEQ ID NO: 45: 1018ISS #40
SEQ ID NO: 46: C-OVA7
SEQ ID NO: 47: compK3
SEQ ID NO: 48: C-OVA2-14
SEQ ID NO: 49: C-OVA2-17
SEQ ID NO: 50: OVA2-17-C
SEQ ID NO: 51: C-OVA2-16
SEQ ID NO: 52: dC-mTRP2pep8; 1st amino acid=D-cysteine
SEQ ID NO: 53: homoC-mTRP2pep8; 1st amino acid=L-homocysteine
SEQ ID NO: 54: Pen-mTRP2pep8; 1st amino acid=L-penicillamine

The invention claimed is:

1. An immunity-inducing agent composition comprising a polynucleotide-peptide conjugate or a pharmaceutically acceptable salt thereof, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding, wherein the polynucleotide derivative is a polynucleotide comprising a modification for increasing nuclease resistance, and wherein the amino acid having a reactive functional group which allows for the formation of a covalent bond with the spacer is cysteine or an analogue thereof, wherein the analogue is an amino acid having a side chain containing thiol.

2. The immunity-inducing agent composition according to claim 1, wherein one or both of the covalent bond between the spacer and the polynucleotide or polynucleotide derivative, and the covalent bond between the spacer and the peptide are a covalent bond or bonds cleavable in biological environment.

3. The immunity-inducing agent composition according to claim 1, wherein the covalent bond between the spacer and the peptide is a disulfide bond.

4. The immunity-inducing agent composition according to claim 1, wherein the MHC-binding peptide is an MHC-1-binding peptide.

5. The immunity-inducing agent composition according to claim 4, wherein the MHC-1-binding peptide is an HLA-A-binding peptide or an HLA-B-binding peptide.

6. The immunity-inducing agent composition according to claim 4, wherein the MHC-1-binding peptide has an amino acid length of not less than 8 and not more than 11.

7. The immunity-inducing agent composition according to claim 1, wherein the MHC-binding peptide is an MHC-2-binding peptide.

8. The immunity-inducing agent composition according to claim 1, wherein the polynucleotide or polynucleotide derivative is a polydeoxyribonucleotide (DNA) or DNA derivative comprising two or more CpG motifs.

9. The immunity-inducing agent composition according to claim 1, wherein the polynucleotide or polynucleotide derivative has a nucleotide length of not less than 15 and not more than 40.

10. The immunity-inducing agent composition according to claim 9, wherein the polynucleotide or polynucleotide derivative has a nucleotide length of not less than 20 and not more than 30.

11. The immunity-inducing agent composition according to claim 1, wherein the polynucleotide or polynucleotide derivative is a polynucleotide derivative in which phosphodiester bonds are at least partially substituted with phosphorothioate bonds.

12. The immunity-inducing agent composition according to claim 11, wherein, in the polynucleotide derivative in which phosphodiester bonds are at least partially substituted with phosphorothioate bonds, not less than 50% of the phosphodiester bonds are substituted with phosphorothioate bonds.

13. The immunity-inducing agent composition according to claim 12, wherein, in the polynucleotide derivative in which phosphodiester bonds are at least partially substituted with phosphorothioate bonds, not less than 90% of the phosphodiester bonds are substituted with phosphorothioate bonds.

14. The immunity-inducing agent composition according to claim 1, wherein the spacer comprises repeating units represented by the following formula:

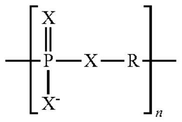

wherein

X represents an oxygen atom or a sulfur atom, wherein each X may be the same or different, R represents any of $(CH_2)_pO$, $(CH_2)_qNH$, and $(CH_2CH_2O)_m$ (wherein m, p and q each independently represent a natural number of not more than 10), and n represents a natural number of not more than 10.

15. The immunity-inducing agent composition according to claim 1, wherein the spacer has a structure represented by any of the following formulas:

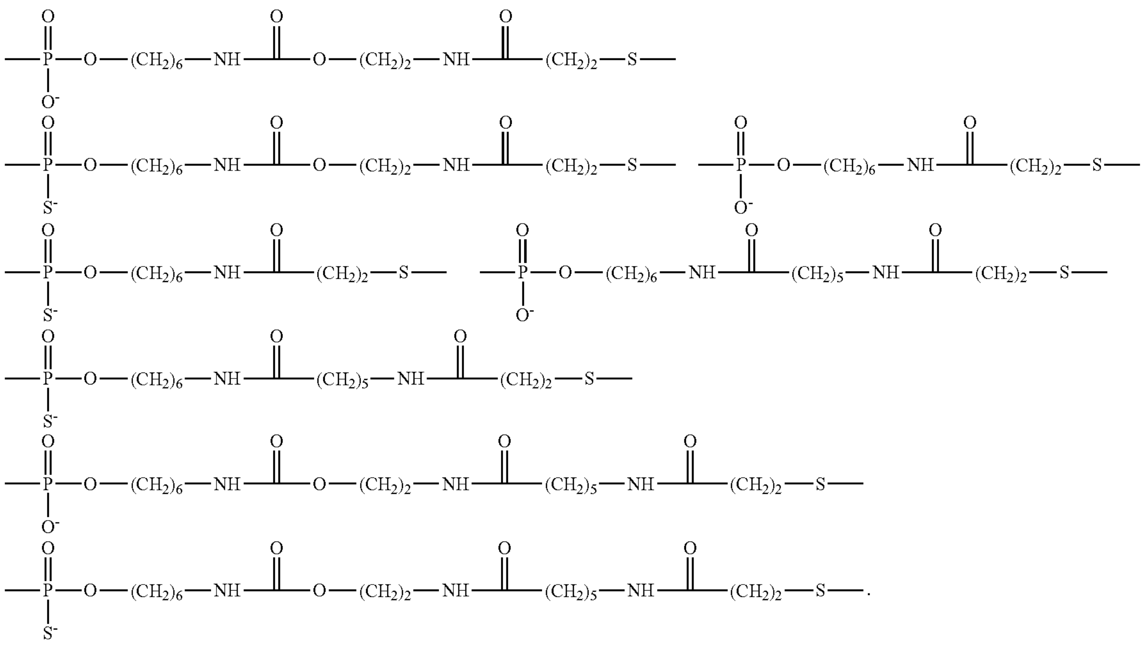

16. The immunity-inducing agent composition according to claim 1, wherein the spacer has a structure represented by any of the following formulas:

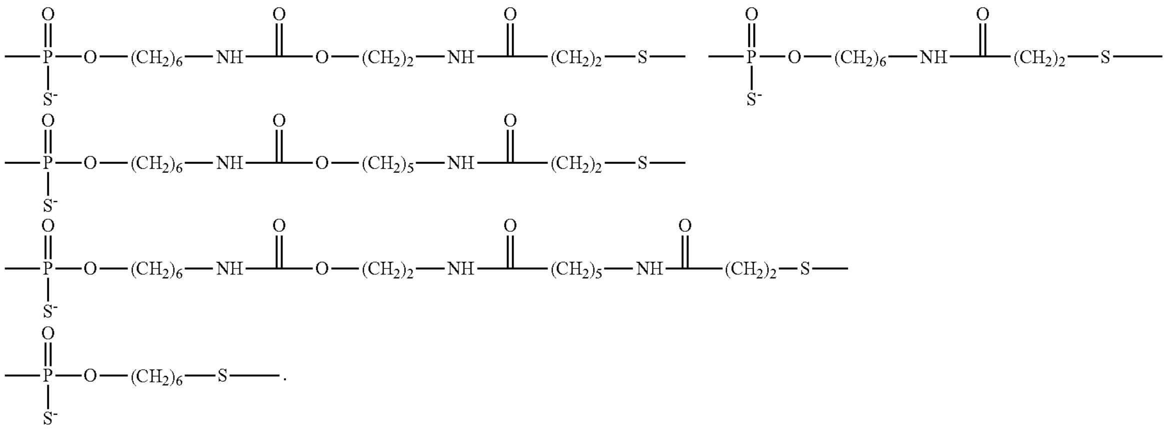

17. The immunity-inducing agent composition comprising a polynucleotide-peptide conjugate or a pharmaceutically acceptable salt thereof, according to claim 1, wherein one or both of the covalent bond between the spacer and the polynucleotide or polynucleotide derivative, and the covalent bond between the spacer and the peptide are a covalent bond or bonds cleavable in biological environment, wherein the polynucleotide or polynucleotide derivative is a polydeoxyribonucleotide (DNA) or DNA derivative comprising two or more CpG motifs, wherein the polynucleotide or polynucleotide derivative is a polynucleotide derivative in which phosphodiester bonds are at least partially substituted with phosphorothioate bonds.

18. The immunity-inducing agent composition comprising a polynucleotide-peptide conjugate or a pharmaceutically acceptable salt thereof, according to claim 1, wherein the amino acid having a reactive functional group which allows for the formation of a covalent bond with the spacer is cysteine or an analogue thereof, wherein the analogue is an amino acid having a side chain containing thiol, wherein the covalent bond between the spacer and the peptide is a disulfide bond, wherein the MHC-binding peptide is an MHC-1-binding peptide, wherein the MHC-1-binding peptide is an HLA-A-binding peptide or an HLA-B-binding peptide, wherein the MHC-1-binding peptide has an amino acid length of not less than 8 and not more than 11, wherein the polynucleotide or polynucleotide derivative is a polydeoxyribonucleotide (DNA) or DNA derivative comprising two or more CpG motifs, wherein the polynucleotide or polynucleotide derivative has a nucleotide length of not less than 20 and not more than 30, wherein, in the polynucleotide derivative in which phosphodiester bonds are at least partially substituted with phosphorothioate bonds, not less than 90% of the phosphodiester bonds are substituted with phosphorothioate bonds, wherein the spacer has a structure represented by any of the following formulas:

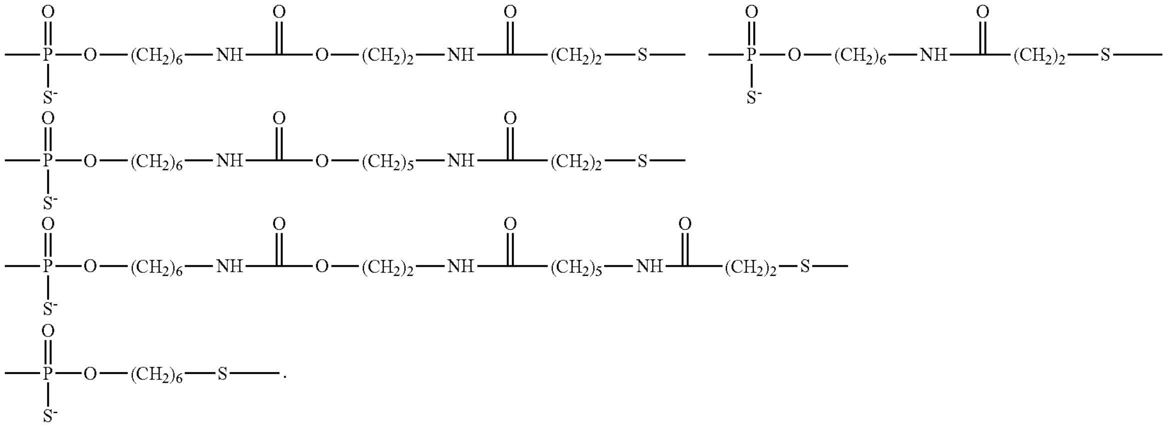

19. The immunity-inducing agent composition according to claim 1, further comprising a substance having immunostimulatory activity as an adjuvant.

20. A pharmaceutical composition comprising the immunity-inducing agent composition according to claim 1.

21. A method for treating or preventing infections, tumors, or allergic diseases, the method comprising administering the immunity-inducing agent composition according to claim 1 to a patient.

22. A method for treating or preventing tumors, the method comprising administering the immunity-inducing agent composition according to claim 1 to a patient.

23. A polynucleotide-peptide conjugate or a pharmaceutically acceptable salt thereof, wherein the polynucleotide-peptide conjugate consists of: a single-chain polynucleotide or polynucleotide derivative comprising a CpG motif; a peptide; and a spacer which is covalently bonded at one end thereof to the polynucleotide or polynucleotide derivative and covalently bonded at the other end thereof to the peptide, wherein the peptide is a peptide modified by substituting one or more contiguous amino acids at the N-terminus of an MHC-binding peptide with an amino acid having a reactive functional group which allows for the formation of a covalent bond with the spacer, wherein the one or more contiguous amino acids contain no anchor residues for MHC binding, and wherein the polynucleotide derivative is a polynucleotide comprising a modification for increasing nuclease resistance, and wherein the amino acid having a reactive functional group which allows for the formation of a covalent bond with the spacer is cysteine or an analogue thereof, wherein the analogue is an amino acid having a side chain containing thiol.

24. The polynucleotide-peptide conjugate or a pharmaceutically acceptable salt thereof according to claim 23, wherein one or both of the covalent bond between the spacer and the polynucleotide or polynucleotide derivative, and the covalent bond between the spacer and the peptide are a covalent bond or bonds cleavable in biological environment, wherein the polynucleotide or polynucleotide derivative is a polydeoxyribonucleotide (DNA) or DNA derivative comprising two or more CpG motifs, wherein the polynucleotide or polynucleotide derivative is a polynucleotide derivative in which phosphodiester bonds are at least partially substituted with phosphorothioate bonds.

25. The polynucleotide-peptide conjugate or a pharmaceutically acceptable salt thereof according to claim 23, wherein the amino acid having a reactive functional group which allows for the formation of a covalent bond with the spacer is cysteine or an analogue thereof, wherein the analogue is an amino acid having a side chain containing thiol, wherein the covalent bond between the spacer and the peptide is a disulfide bond, wherein the MHC-binding peptide is an MHC-1-binding peptide, wherein the MHC-1-binding peptide is an HLA-A-binding peptide or an HLA-B-binding peptide, wherein the MHC-1-binding peptide has an amino acid length of not less than 8 and not more than 11, wherein the polynucleotide or polynucleotide derivative is a polydeoxyribonucleotide (DNA) or DNA derivative comprising two or more CpG motifs, wherein the polynucleotide or polynucleotide derivative has a nucleotide length of not less than 20 and not more than 30, wherein, in the polynucleotide derivative in which phosphodiester bonds are at least partially substituted with phosphorothioate bonds, not less than 90% of the phosphodiester bonds are substituted with phosphorothioate bonds, wherein the spacer has a structure represented by any of the following formulas:

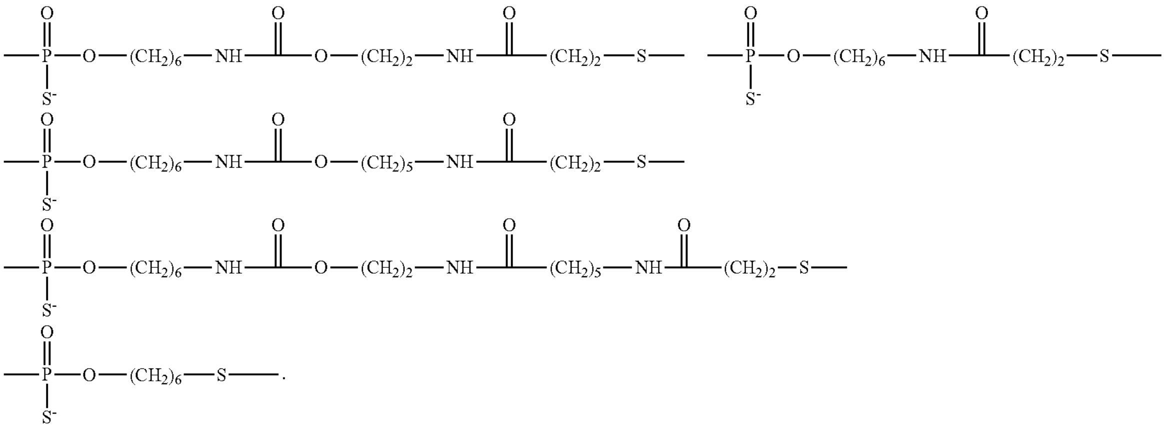
26. A method for inducing protective immune response, the method comprising administering the immunity-inducing agent composition according to claim 1 to a patient.
* * * * *

SEQUENCE LISTING

```
<160> NUMBER OF SEQ ID NOS: 54

<210> SEQ ID NO 1
<211> LENGTH: 20
<212> TYPE: DNA
<213> ORGANISM: Artificial Sequence
<220> FEATURE:
<223> OTHER INFORMATION: K3

<400> SEQUENCE: 1

atcgactctc gagcgttctc                                          20


<210> SEQ ID NO 2
<211> LENGTH: 20
<212> TYPE: DNA
<213> ORGANISM: Artificial Sequence
<220> FEATURE:
<223> OTHER INFORMATION: K3-20(b)

<400> SEQUENCE: 2

gagcgttctc gagcgttctc                                          20


<210> SEQ ID NO 3
<211> LENGTH: 21
<212> TYPE: DNA
<213> ORGANISM: Artificial Sequence
<220> FEATURE:
<223> OTHER INFORMATION: K3-21

<400> SEQUENCE: 3

cgagcgttct cgagcgttct c                                        21
```

<210> SEQ ID NO 4
<211> LENGTH: 24
<212> TYPE: DNA
<213> ORGANISM: Artificial Sequence
<220> FEATURE:
<223> OTHER INFORMATION: K3-24

<400> SEQUENCE: 4
tctcgagcgt tctcgagcgt tctc 24

<210> SEQ ID NO 5
<211> LENGTH: 27
<212> TYPE: DNA
<213> ORGANISM: Artificial Sequence
<220> FEATURE:
<223> OTHER INFORMATION: K3-27

<400> SEQUENCE: 5
gactctcgag cgttctcgag cgttctc 27

<210> SEQ ID NO 6
<211> LENGTH: 30
<212> TYPE: DNA
<213> ORGANISM: Artificial Sequence
<220> FEATURE:
<223> OTHER INFORMATION: K3-30(a)

<400> SEQUENCE: 6
gagcgttctc atcgactctc gagcgttctc 30

<210> SEQ ID NO 7
<211> LENGTH: 30
<212> TYPE: DNA
<213> ORGANISM: Artificial Sequence
<220> FEATURE:
<223> OTHER INFORMATION: K3-30(b)

<400> SEQUENCE: 7
atcgactctc gagcgttctc gagcgttctc 30

<210> SEQ ID NO 8
<211> LENGTH: 40
<212> TYPE: DNA
<213> ORGANISM: Artificial Sequence
<220> FEATURE:
<223> OTHER INFORMATION: K3-40

<400> SEQUENCE: 8
atcgactctc gagcgttctc atcgactctc gagcgttctc 40

<210> SEQ ID NO 9
<211> LENGTH: 30
<212> TYPE: DNA
<213> ORGANISM: Artificial Sequence
<220> FEATURE:
<223> OTHER INFORMATION: K3-30(c)

<400> SEQUENCE: 9
ctcagcgttc tcagcgttct cagcgttctc 30

<210> SEQ ID NO 10
<211> LENGTH: 30
<212> TYPE: DNA
<213> ORGANISM: Artificial Sequence
<220> FEATURE:

<223> OTHER INFORMATION: K3-30(d)

<400> SEQUENCE: 10
tttagcgttt ttagcgtttt tagcgttttt 30

<210> SEQ ID NO 11
<211> LENGTH: 30
<212> TYPE: DNA
<213> ORGANISM: Artificial Sequence
<220> FEATURE:
<223> OTHER INFORMATION: K3-30(e)

<400> SEQUENCE: 11
ttagcgttta gcgtttagcg tttagcgttt 30

<210> SEQ ID NO 12
<211> LENGTH: 30
<212> TYPE: DNA
<213> ORGANISM: Artificial Sequence
<220> FEATURE:
<223> OTHER INFORMATION: K3-30(f)

<400> SEQUENCE: 12
ttagcgttca gcgttcagcg ttcagcgttt 30

<210> SEQ ID NO 13
<211> LENGTH: 26
<212> TYPE: DNA
<213> ORGANISM: Artificial Sequence
<220> FEATURE:
<223> OTHER INFORMATION: K3-26(a)

<400> SEQUENCE: 13
tcagcgtttc agcgtttcag cgtttc 26

<210> SEQ ID NO 14
<211> LENGTH: 26
<212> TYPE: DNA
<213> ORGANISM: Artificial Sequence
<220> FEATURE:
<223> OTHER INFORMATION: K3-26(b)

<400> SEQUENCE: 14
ttagcgtttt agcgttttag cgtttt 26

<210> SEQ ID NO 15
<211> LENGTH: 20
<212> TYPE: DNA
<213> ORGANISM: Artificial Sequence
<220> FEATURE:
<223> OTHER INFORMATION: ODN1668

<400> SEQUENCE: 15
tccatgacgt tcctgatgct 20

<210> SEQ ID NO 16
<211> LENGTH: 30
<212> TYPE: DNA
<213> ORGANISM: Artificial Sequence
<220> FEATURE:
<223> OTHER INFORMATION: ODN1668-30

<400> SEQUENCE: 16
tgacgttcct tccatgacgt tcctgatgct 30

-continued

<210> SEQ ID NO 17
<211> LENGTH: 40
<212> TYPE: DNA
<213> ORGANISM: Artificial Sequence
<220> FEATURE:
<223> OTHER INFORMATION: ODN1668-40

<400> SEQUENCE: 17
tccatgacgt tcctgatgct tccatgacgt tcctgatgct 40

<210> SEQ ID NO 18
<211> LENGTH: 20
<212> TYPE: DNA
<213> ORGANISM: Artificial Sequence
<220> FEATURE:
<223> OTHER INFORMATION: ODN1826

<400> SEQUENCE: 18
tccatgacgt tcctgacgtt 20

<210> SEQ ID NO 19
<211> LENGTH: 30
<212> TYPE: DNA
<213> ORGANISM: Artificial Sequence
<220> FEATURE:
<223> OTHER INFORMATION: ODN1826-30

<400> SEQUENCE: 19
tgacgttcct tccatgacgt tcctgacgtt 30

<210> SEQ ID NO 20
<211> LENGTH: 40
<212> TYPE: DNA
<213> ORGANISM: Artificial Sequence
<220> FEATURE:
<223> OTHER INFORMATION: ODN1826-40

<400> SEQUENCE: 20
tccatgacgt tcctgacgtt tccatgacgt tcctgacgtt 40

<210> SEQ ID NO 21
<211> LENGTH: 24
<212> TYPE: DNA
<213> ORGANISM: Artificial Sequence
<220> FEATURE:
<223> OTHER INFORMATION: ODN2006

<400> SEQUENCE: 21
tcgtcgtttt gtcgttttgt cgtt 24

<210> SEQ ID NO 22
<211> LENGTH: 30
<212> TYPE: DNA
<213> ORGANISM: Artificial Sequence
<220> FEATURE:
<223> OTHER INFORMATION: ODN2006-30

<400> SEQUENCE: 22
gtcgtttcgt cgttttgtcg ttttgtcgtt 30

<210> SEQ ID NO 23
<211> LENGTH: 40
<212> TYPE: DNA
<213> ORGANISM: Artificial Sequence
<220> FEATURE:
<223> OTHER INFORMATION: ODN2006-40

-continued

<400> SEQUENCE: 23
tcgtcgtttt gtcgtttcgt cgttttgtcg ttttgtcgtt 40

<210> SEQ ID NO 24
<211> LENGTH: 23
<212> TYPE: DNA
<213> ORGANISM: Artificial Sequence
<220> FEATURE:
<223> OTHER INFORMATION: ODN684

<400> SEQUENCE: 24
tcgacgttcg tcgttcgtcg ttc 23

<210> SEQ ID NO 25
<211> LENGTH: 30
<212> TYPE: DNA
<213> ORGANISM: Artificial Sequence
<220> FEATURE:
<223> OTHER INFORMATION: ODN684-30

<400> SEQUENCE: 25
tcgtcgttcg acgttcgtcg ttcgtcgttc 30

<210> SEQ ID NO 26
<211> LENGTH: 40
<212> TYPE: DNA
<213> ORGANISM: Artificial Sequence
<220> FEATURE:
<223> OTHER INFORMATION: ODN684-40

<400> SEQUENCE: 26
gttcgtcgtt tcgtcgttcg acgttcgtcg ttcgtcgttc 40

<210> SEQ ID NO 27
<211> LENGTH: 26
<212> TYPE: DNA
<213> ORGANISM: Artificial Sequence
<220> FEATURE:
<223> OTHER INFORMATION: ODN D-SL01

<400> SEQUENCE: 27
tcgcgacgtt cgcccgacgt tcggta 26

<210> SEQ ID NO 28
<211> LENGTH: 35
<212> TYPE: DNA
<213> ORGANISM: Artificial Sequence
<220> FEATURE:
<223> OTHER INFORMATION: ODN D-SL01-35

<400> SEQUENCE: 28
tcgcgacgtt cgcgacgttc gcccgacgtt cggta 35

<210> SEQ ID NO 29
<211> LENGTH: 30
<212> TYPE: DNA
<213> ORGANISM: Artificial Sequence
<220> FEATURE:
<223> OTHER INFORMATION: C-CpG_1

<400> SEQUENCE: 29
tcgaacgttc gaacgttcga acgttcgaat 30

<210> SEQ ID NO 30
<211> LENGTH: 9

-continued

<212> TYPE: PRT
<213> ORGANISM: Artificial Sequence
<220> FEATURE:
<223> OTHER INFORMATION: C-OVA8

<400> SEQUENCE: 30

Cys Ser Ile Ile Asn Phe Glu Lys Leu
1 5

<210> SEQ ID NO 31
<211> LENGTH: 10
<212> TYPE: PRT
<213> ORGANISM: Artificial Sequence
<220> FEATURE:
<223> OTHER INFORMATION: C-TRP2-9

<400> SEQUENCE: 31

Cys Ser Val Tyr Asp Phe Phe Val Trp Leu
1 5 10

<210> SEQ ID NO 32
<211> LENGTH: 9
<212> TYPE: PRT
<213> ORGANISM: Artificial Sequence
<220> FEATURE:
<223> OTHER INFORMATION: C-TRP2-8

<400> SEQUENCE: 32

Cys Val Tyr Asp Phe Phe Val Trp Leu
1 5

<210> SEQ ID NO 33
<211> LENGTH: 10
<212> TYPE: PRT
<213> ORGANISM: Artificial Sequence
<220> FEATURE:
<223> OTHER INFORMATION: C-gp100-9

<400> SEQUENCE: 33

Cys Lys Val Pro Arg Asn Gln Asp Trp Leu
1 5 10

<210> SEQ ID NO 34
<211> LENGTH: 9
<212> TYPE: PRT
<213> ORGANISM: Artificial Sequence
<220> FEATURE:
<223> OTHER INFORMATION: C-gp100-8

<400> SEQUENCE: 34

Cys Val Pro Arg Asn Gln Asp Trp Leu
1 5

<210> SEQ ID NO 35
<211> LENGTH: 11
<212> TYPE: PRT
<213> ORGANISM: Artificial Sequence
<220> FEATURE:
<223> OTHER INFORMATION: CM-TRP2-9

<400> SEQUENCE: 35

Cys Met Ser Val Tyr Asp Phe Phe Val Trp Leu
1 5 10

<210> SEQ ID NO 36
<211> LENGTH: 14
<212> TYPE: PRT

<213> ORGANISM: Artificial Sequence
<220> FEATURE:
<223> OTHER INFORMATION: C-TRP2-13

<400> SEQUENCE: 36

Cys Phe Ala Asn Ala Ser Val Tyr Asp Phe Phe Val Trp Leu
1 5 10

<210> SEQ ID NO 37
<211> LENGTH: 12
<212> TYPE: PRT
<213> ORGANISM: Artificial Sequence
<220> FEATURE:
<223> OTHER INFORMATION: C-TRP2-11

<400> SEQUENCE: 37

Cys Asn Ala Ser Val Tyr Asp Phe Phe Val Trp Leu
1 5 10

<210> SEQ ID NO 38
<211> LENGTH: 18
<212> TYPE: PRT
<213> ORGANISM: Artificial Sequence
<220> FEATURE:
<223> OTHER INFORMATION: C-OVA2-17

<400> SEQUENCE: 38

Cys Ile Ser Gln Ala Val His Ala Ala His Ala Glu Ile Asn Glu Ala
1 5 10 15

Gly Arg

<210> SEQ ID NO 39
<211> LENGTH: 15
<212> TYPE: PRT
<213> ORGANISM: Artificial Sequence
<220> FEATURE:
<223> OTHER INFORMATION: C-OVA2-14

<400> SEQUENCE: 39

Cys Ser Gln Ala Val His Ala Ala His Ala Glu Ile Asn Glu Ala
1 5 10 15

<210> SEQ ID NO 40
<211> LENGTH: 12
<212> TYPE: PRT
<213> ORGANISM: Artificial Sequence
<220> FEATURE:
<223> OTHER INFORMATION: C-OVA2-11

<400> SEQUENCE: 40

Cys Ala Val His Ala Ala His Ala Glu Ile Asn Glu
1 5 10

<210> SEQ ID NO 41
<211> LENGTH: 8
<212> TYPE: PRT
<213> ORGANISM: Artificial Sequence
<220> FEATURE:
<223> OTHER INFORMATION: OVA peptide 1

<400> SEQUENCE: 41

Ser Ile Ile Asn Phe Glu Lys Leu
1 5

<210> SEQ ID NO 42
<211> LENGTH: 17

<212> TYPE: PRT
<213> ORGANISM: Artificial Sequence
<220> FEATURE:
<223> OTHER INFORMATION: OVA peptide 2

<400> SEQUENCE: 42

Ile Ser Gln Ala Val His Ala Ala His Ala Glu Ile Asn Glu Ala Gly
1 5 10 15

Arg

<210> SEQ ID NO 43
<211> LENGTH: 22
<212> TYPE: DNA
<213> ORGANISM: Artificial Sequence
<220> FEATURE:
<223> OTHER INFORMATION: 1018ISS

<400> SEQUENCE: 43
tgactgtgaa cgttcgagat ga 22

<210> SEQ ID NO 44
<211> LENGTH: 30
<212> TYPE: DNA
<213> ORGANISM: Artificial Sequence
<220> FEATURE:
<223> OTHER INFORMATION: 1018ISS_30

<400> SEQUENCE: 44
tgaacgttcg actgtgaacg ttcgagatga 30

<210> SEQ ID NO 45
<211> LENGTH: 40
<212> TYPE: DNA
<213> ORGANISM: Artificial Sequence
<220> FEATURE:
<223> OTHER INFORMATION: 1018ISS_40

<400> SEQUENCE: 45
tgaacgttcg tgaacgttcg actgtgaacg ttcgagatga 40

<210> SEQ ID NO 46
<211> LENGTH: 8
<212> TYPE: PRT
<213> ORGANISM: Artificial Sequence
<220> FEATURE:
<223> OTHER INFORMATION: C-OVA7

<400> SEQUENCE: 46

Cys Ile Ile Asn Phe Glu Lys Leu
1 5

<210> SEQ ID NO 47
<211> LENGTH: 16
<212> TYPE: DNA
<213> ORGANISM: Artificial Sequence
<220> FEATURE:
<223> OTHER INFORMATION: compK3

<400> SEQUENCE: 47
gagaacgctc gagagt 16

<210> SEQ ID NO 48
<211> LENGTH: 15
<212> TYPE: PRT
<213> ORGANISM: Artificial Sequence
<220> FEATURE:

<223> OTHER INFORMATION: C-OVA2-14

<400> SEQUENCE: 48

Cys Ser Gln Ala Val His Ala Ala His Ala Glu Ile Asn Glu Ala
1 5 10 15

<210> SEQ ID NO 49
<211> LENGTH: 18
<212> TYPE: PRT
<213> ORGANISM: Artificial Sequence
<220> FEATURE:
<223> OTHER INFORMATION: C-OVA2-17

<400> SEQUENCE: 49

Cys Ile Ser Gln Ala Val His Ala Ala His Ala Glu Ile Asn Glu Ala
1 5 10 15

Gly Arg

<210> SEQ ID NO 50
<211> LENGTH: 18
<212> TYPE: PRT
<213> ORGANISM: Artificial Sequence
<220> FEATURE:
<223> OTHER INFORMATION: OVA2-17-C

<400> SEQUENCE: 50

Ile Ser Gln Ala Val His Ala Ala His Ala Glu Ile Asn Glu Ala Gly
1 5 10 15

Arg Cys

<210> SEQ ID NO 51
<211> LENGTH: 17
<212> TYPE: PRT
<213> ORGANISM: Artificial Sequence
<220> FEATURE:
<223> OTHER INFORMATION: C-OVA2-16

<400> SEQUENCE: 51

Cys Ser Gln Ala Val His Ala Ala His Ala Glu Ile Asn Glu Ala Gly
1 5 10 15

Arg

<210> SEQ ID NO 52
<211> LENGTH: 9
<212> TYPE: PRT
<213> ORGANISM: Artificial Sequence
<220> FEATURE:
<223> OTHER INFORMATION: dC-mTRP2pep8
<220> FEATURE:
<221> NAME/KEY: X
<222> LOCATION: (1)..(1)
<223> OTHER INFORMATION: D-cysteine

<400> SEQUENCE: 52

Xaa Val Tyr Asp Phe Phe Val Trp Leu
1 5

<210> SEQ ID NO 53
<211> LENGTH: 9
<212> TYPE: PRT
<213> ORGANISM: Artificial Sequence
<220> FEATURE:
<223> OTHER INFORMATION: homoC-mTRP2pep8
<220> FEATURE:
<221> NAME/KEY: X
<222> LOCATION: (1)..(1)

-continued

<223> OTHER INFORMATION: L-homocysteine

<400> SEQUENCE: 53

Xaa Val Tyr Asp Phe Phe Val Trp Leu
1 5

<210> SEQ ID NO 54
<211> LENGTH: 9
<212> TYPE: PRT
<213> ORGANISM: Artificial Sequence
<220> FEATURE:
<223> OTHER INFORMATION: Pen-mTRP2pep8
<220> FEATURE:
<221> NAME/KEY: X
<222> LOCATION: (1)..(1)
<223> OTHER INFORMATION: L-penicillamine

<400> SEQUENCE: 54

Xaa Val Tyr Asp Phe Phe Val Trp Leu
1 5